(12) United States Patent
Selby et al.

(10) Patent No.: US 6,740,323 B1
(45) Date of Patent: May 25, 2004

(54) HBV/HCV VIRUS-LIKE PARTICLE

(75) Inventors: Mark Selby, San Francisco, CA (US);
Edward Glazer, Oakland, CA (US);
Michael Houghton, Berkeley, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/721,480

(22) Filed: Nov. 22, 2000

Related U.S. Application Data
(60) Provisional application No. 60/167,224, filed on Nov. 24, 1999.

(51) Int. Cl.$^7$ .................. A61K 39/29; A61K 39/295
(52) U.S. Cl. ................ 424/189.1; 435/236; 530/350; 424/186.1; 424/192.1
(58) Field of Search .................. 435/236; 530/350; 424/186.1

(56) References Cited

U.S. PATENT DOCUMENTS

| | | |
|---|---|---|
| 4,722,840 A | 2/1988 | Valenzuela et al. |
| 5,098,704 A | 3/1992 | Valenzuela et al. |
| 5,324,513 A | 6/1994 | Sobczak et al. |
| 5,792,463 A | 8/1998 | Valenzuela et al. |

FOREIGN PATENT DOCUMENTS

| | | | |
|---|---|---|---|
| EP | 0 201 416 A1 | | 11/1986 |
| WO | WO 96/04301 | * | 2/1996 |

OTHER PUBLICATIONS

Delpeyroux et al., Presentation and Immunogenicity of the Hepatitis B Surface Antigen and a Poliovirus Neutralization Antigen on Mixed Empty Envelope Particles. J. Virol. 62(5):1836–1839, 1988.*

Lee et al., Presentation of the Hydrophilic Domains of Hepatitis C Viral E2 Envelope Glycoprotein on Hepatitis B Surface Antigen Particles. Journal of Medical Virology 50:145–151, 1996.*

Major et al., " DNA–based immunization with chimeric vectors for the induction of immune responses against the hepatitis C virus nucleocapsid," *J. Virology* 69(9):5798–5805, 1995.

Delpeyroux et al., "Structural Factors Modulate the Activity of Antigenic Poliovirus Sequences Expressed on Hybrid Hepatitis B surface Antigen Particles," *J. Virol.* 64(12):6090–6100 (1990).

Edman et al., " Synthesis of Hepatitis B Surface and Core Antigens in *E. coli*," *Nature 291*:503–506 (1981).

Inchauspé et al., "DNA Vaccination for the Induction of Immune Responses Against Hepatitis C Virus Proteins," *Vaccine 15*(8):853–856 (1997).

Inchauspé et al., "Immune Responses Against Hepatitis C Virus Structural Proteins Following Genetic Immunization," *Dev. Biol. Stand. 92*:163–168 (1998).

Lee et al., "Characterization of a New Genotype II Hepatitis Delta Virus from Taiwan," *Journal of Medical Virology 49*:145–154 (1996).

Nakano et al., "Immunization with Plasmid DNA Encoding Hepatitis C Virus Envelope E2 Antigenic Domains Induces Antibodies Whose Immune Reactivity is Linked to the Injection Mode," *Journal of Virology 71*(9):7101–7109 (1997).

Valenzuela et al., "Antigen Engineering in Yeast: Synthesis and Assembly of Hybrid Hepatitis B Surface Antigen–Herpes Simplex 1 gD Particles," *Bio/Technology 3*:323–326 (1985).

* cited by examiner

*Primary Examiner*—Donna C. Wortman
(74) *Attorney, Agent, or Firm*—Roberta L. Robins; Alisa A. Harbin; Robert P. Blackburn

(57) ABSTRACT

Chimeric antigens derived from hepatitis B virus (HBV) and hepatitis C virus (HCV) are described which form virus-like particles when co-expressed with an excess of hepatitis B virus surface antigen (HBsAg). The chimeric antigens are fusion proteins containing an immunogenic peptide derived from an HCV protein coupled to the amino terminus of HBsAg. Also described are nucleic acid constructs and vectors for transfection of cells and expression of the chimeric antigens. The invention further provides methods for producing HBV/HCV virus-like particles containing the chimeric antigens, cell lines for producing the virus-like particles, combination vaccines containing the virus-like particles, and DNA vaccines that express the virus-like particles.

20 Claims, 43 Drawing Sheets

SEQ ID NO: 1     pCMV II

```
  1  TCGCGCGTTT CGGTGATGAC GGTGAAAACC TCTGACACAT GCAGCTCCCG
     AGCGCGCAAA GCCACTACTG CCACTTTTGG AGACTGTGTA CGTCGAGGGC

51  GAGACGGTCA CAGCTTGTCT GTAAGCGGAT GCCGGGAGCA GACAAGCCCG
     CTCTGCCAGT GTCGAACAGA CATTCGCCTA CGGCCCTCGT CTGTTCGGGC

101  TCAGGGCGCG TCAGCGGGTG TTGGCGGGTG TCGGGCTGG  CTTAACTATG
     AGTCCCGCGC AGTCGCCCAC AACCGCCCAC AGCCCGACC  GAATTGATAC

HindIII
                                              --------
151  CGGCATCAGA GCAGATTGTA CTGAGAGTGC ACCATATGAA GCTTTTTGCA
     GCCGTAGTCT CGTCTAACAT GACTCTCACG TGGTATACTT CGAAAAACGT 201  AAAGCCTAGG CCTCCAAAAA AGCCTCCTCA CTACTTCTGG AATAGCTCAG
     TTTCGGATCC GGAGGTTTTT TCGGAGGAGT GATGAAGACC TTATCGAGTC 251  AGGCCGAGGC GGCCTCGGCC TCTGCATAAA TAAAAAAAAT TAGTCAGCCA
     TCCGGCTCCG CCGGAGCCGG AGACGTATTT ATTTTTTTTA ATCAGTCGGT 301  TGGGGCGGAG AATGGGCGGA ACTGGGCGGG GAGGGAATTA TTGGCTATTG
     ACCCCGCCTC TTACCCGCCT TGACCCGCCC CTCCCTTAAT AACCGATAAC 351  GCCATTGCAT ACGTTGTATC TATATCATAA TATGTACATT TATATTGGCT
     CGGTAACGTA TGCAACATAG ATATAGTATT ATACATGTAA ATATAACCGA 401  CATGTCCAAT ATGACCGCCA TGTTGACATT GATTATTGAC TAGTTATTAA
     GTACAGGTTA TACTGGCGGT ACAACTGTAA CTAATAACTG ATCAATAATT 451  TAGTAATCAA TTACGGGGTC ATTAGTTCAT AGCCCATATA TGGAGTTCCG
     ATCATTAGTT AATGCCCCAG TAATCAAGTA TCGGGTATAT ACCTCAAGGC 501  CGTTACATAA CTTACGGTAA ATGGCCCGCC TGGCTGACCG CCCAACGACC
     GCAATGTATT GAATGCCATT TACCGGGCGG ACCGACTGGC GGGTTGCTGG 551  CCCGCCCATT GACGTCAATA ATGACGTATG TTCCCATAGT AACGCCAATA
     GGGCGGGTAA CTGCAGTTAT TACTGCATAC AAGGGTATCA TTGCGGTTAT 601  GGGACTTTCC ATTGACGTCA ATGGGTGGAG TATTTACGGT AAACTGCCCA
     CCCTGAAAGG TAACTGCAGT TACCCACCTC ATAAATGCCA TTTGACGGGT 651  CTTGGCAGTA CATCAAGTGT ATCATATGCC AAGTCCGCCC CCTATTGACG
     GAACCGTCAT GTAGTTCACA TAGTATACGG TTCAGGCGGG GGATAACTGC 701  TCAATGACGG TAAATGGCCC GCCTGGCATT ATGCCCAGTA CATGACCTTA
     AGTTACTGCC ATTTACCGGG CGGACCGTAA TACGGGTCAT GTACTGGAAT 751  CGGGACTTTC CTACTTGGCA GTACATCTAC GTATTAGTCA TCGCTATTAC
     GCCCTGAAAG GATGAACCGT CATGTAGATG CATAATCAGT AGCGATAATG 801  CATGGTGATG CGGTTTTGGC AGTACACCAA TGGGCGTGGA TAGCGGTTTG
     GTACCACTAC GCCAAAACCG TCATGTGGTT ACCCGCACCT ATCGCCAAAC 851  ACTCACGGGG ATTTCCAAGT CTCCACCCCA TTGACGTCAA TGGGAGTTTG
     TGAGTGCCCC TAAAGGTTCA GAGGTGGGGT AACTGCAGTT ACCCTCAAAC
```

FIG. 1B

```
 901  TTTTGGCACC  AAAATCAACG  GGACTTTCCA  AAATGTCGTA  ATAACCCCGC
      AAAACCGTGG  TTTTAGTTGC  CCTGAAAGGT  TTTACAGCAT  TATTGGGGCG

951  CCCGTTGACG  CAAATGGGCG  GTAGGCGTGT  ACGGTGGGAG  GTCTATATAA
      GGGCAACTGC  GTTTACCCGC  CATCCGCACA  TGCCACCCTC  CAGATATATT

1001  GCAGAGCTCG  TTTAGTGAAC  CGTCAGATCG  CCTGGAGACG  CCATCCACGC
      CGTCTCGAGC  AAATCACTTG  GCAGTCTAGC  GGACCTCTGC  GGTAGGTGCG

1051  TGTTTTGACC  TCCATAGAAG  ACACCGGGAC  CGATCCAGCC  TCCGCGGCCG
      ACAAAACTGG  AGGTATCTTC  TGTGGCCCTG  GCTAGGTCGG  AGGCGCCGGC

1101  GGAACGGTGC  ATTGGAACGC  GGATTCCCCG  TGCCAAGAGT  GACGTAAGTA
      CCTTGCCACG  TAACCTTGCG  CCTAAGGGGC  ACGGTTCTCA  CTGCATTCAT

1151  CCGCCTATAG  ACTCTATAGG  CACACCCCTT  TGGCTCTTAT  GCATGCTATA
      GGCGGATATC  TGAGATATCC  GTGTGGGGAA  ACCGAGAATA  CGTACGATAT

1201  CTGTTTTTGG  CTTGGGGCCT  ATACACCCCC  GCTCCTTATG  CTATAGGTGA
      GACAAAAACC  GAACCCCGGA  TATGTGGGGG  CGAGGAATAC  GATATCCACT

1251  TGGTATAGCT  TAGCCTATAG  GTGTGGGTTA  TTGACCATTA  TTGACCACTC
      ACCATATCGA  ATCGGATATC  CACACCCAAT  AACTGGTAAT  AACTGGTGAG

1301  CCCTATTGGT  GACGATACTT  TCCATTACTA  ATCCATAACA  TGGCTCTTTG
      GGGATAACCA  CTGCTATGAA  AGGTAATGAT  TAGGTATTGT  ACCGAGAAAC

1351  CCACAACTAT  CTCTATTGGC  TATATGCCAA  TACTCTGTCC  TTCAGAGACT
      GGTGTTGATA  GAGATAACCG  ATATACGGTT  ATGAGACAGG  AAGTCTCTGA

1401  GACACGGACT  CTGTATTTTT  ACAGGATGGG  GTCCATTTAT  TATTTACAAA
      CTGTGCCTGA  GACATAAAAA  TGTCCTACCC  CAGGTAAATA  ATAAATGTTT

1451  TTCACATATA  CAACAACGCC  GTCCCCCGTG  CCCGCAGTTT  TTATTAAACA
      AAGTGTATAT  GTTGTTGCGG  CAGGGGGCAC  GGGCGTCAAA  AATAATTTGT

1501  TAGCGTGGGA  TCTCCGACAT  CTCGGGTACG  TGTTCCGGAC  ATGGGCTCTT
      ATCGCACCCT  AGAGGCTGTA  GAGCCCATGC  ACAAGGCCTG  TACCCGAGAA

1551  CTCCGGTAGC  GGCGGAGCTT  CCACATCCGA  GCCCTGGTCC  CATCCGTCCA
      GAGGCCATCG  CCGCCTCGAA  GGTGTAGGCT  CGGGACCAGG  GTAGGCAGGT

1601  GCGGCTCATG  GTCGCTCGGC  AGCTCCTTGC  TCCTAACAGT  GGAGGCCAGA
      CGCCGAGTAC  CAGCGAGCCG  TCGAGGAACG  AGGATTGTCA  CCTCCGGTCT

1651  CTTAGGCACA  GCACAATGCC  CACCACCACC  AGTGTGCCGC  ACAAGGCCGT
      GAATCCGTGT  CGTGTTACGG  GTGGTGGTGG  TCACACGGCG  TGTTCCGGCA

1701  GGCGGTAGGG  TATGTGTCTG  AAAATGAGCT  CGGAGATTGG  GCTCGCACCT
      CCGCCATCCC  ATACACAGAC  TTTTACTCGA  GCCTCTAACC  CGAGCGTGGA

1751  GGACGCAGAT  GGAAGACTTA  AGGCAGCGGC  AGAAGAAGAT  GCAGGCAGCT
      CCTGCGTCTA  CCTTCTGAAT  TCCGTCGCCG  TCTTCTTCTA  CGTCCGTCGA

1801  GAGTTGTTGT  ATTCTGATAA  GAGTCAGAGG  TAACTCCCGT  TGCGGTGCTG
      CTCAACAACA  TAAGACTATT  CTCAGTCTCC  ATTGAGGGCA  ACGCCACGAC
```

FIG. 1C

```
1851  TTAACGGTGG AGGGCAGTGT AGTCTGAGCA CTACTCGTTG CTGCCGCGCG
      AATTGCCACC TCCCGTCACA TCAGACTCGT CATGAGCAAC GACGGCGCGC

1901  CGCCACCAGA CATAATAGCT GACAGACTAA CAGACTGTTC CTTTCCATGG
      GCGGTGGTCT GTATTATCGA CTGTCTGATT GTCTGACAAG GAAAGGTACC

SalI       EcoRI      XhoI
                           ------     ------     ------
1951  GTCTTTTCTG CAGTCACCGT CGTCGACCTA AGAATTCAGA CTCGAGCAAG
      CAGAAAAGAC GTCAGTGGCA GCAGCTGGAT TCTTAAGTCT GAGCTCGTTC

XbaI       AscI       EcoRV      BamHI      MluI
      ------     ----------  --------  --------  --------
2001  TCTAGAAAGG CGCGCCAAGA TATCAAGGAT CCACTACGCG TTAGAGCTCG
      AGATCTTTCC GCGCGGTTCT ATAGTTCCTA GGTGATGCGC AATCTCGAGC

2051  CTGATCAGCC TCGACTGTGC CTTCTAGTTG CCAGCCATCT GTTGTTTGCC
      GACTAGTCGG AGCTGACACG GAAGATCAAC GGTCGGTAGA CAACAAACGG

2101  CCTCCCCCGT GCCTTCCTTG ACCCTGGAAG GTGCCACTCC CACTGTCCTT
      GGAGGGGGCA CGGAAGGAAC TGGGACCTTC CACGGTGAGG GTGACAGGAA

2151  TCCTAATAAA ATGAGGAAAT TGCATCGCAT TGTCTGAGTA GGTGTCATTC
      AGGATTATTT TACTCCTTTA ACGTAGCGTA ACAGACTCAT CCACAGTAAG

2201  TATTCTGGGG GGTGGGGTGG GGCAGGACAG CAAGGGGGAG GATTGGGAAG
      ATAAGACCCC CCACCCCACC CCGTCCTGTC GTTCCCCCTC CTAACCCTTC

2251  ACAATAGCAG GCATGCTGGG GAGCTCTTCC GCTTCCTCGC TCACTGACTC
      TGTTATCGTC CGTACGACCC CTCGAGAAGG CGAAGGAGCG AGTGACTGAG

2301  GCTGCGCTCG GTCGTTCGGC TGCGGCGAGC GGTATCAGCT CACTCAAAGG
      CGACGCGAGC CAGCAAGCCG ACGCCGCTCG CCATAGTCGA GTGAGTTTCC

2351  CGGTAATACG GTTATCCACA GAATCAGGGG ATAACGCAGG AAAGAACATG
      GCCATTATGC CAATAGGTGT CTTAGTCCCC TATTGCGTCC TTTCTTGTAC

2401  TGAGCAAAAG GCCAGCAAAA GGCCAGGAAC CGTAAAAAGG CCGCGTTGCT
      ACTCGTTTTC CGGTCGTTTT CCGGTCCTTG GCATTTTTCC GGCGCAACGA

2451  GGCGTTTTTC CATAGGCTCC GCCCCCCTGA CGAGCATCAC AAAAATCGAC
      CCGCAAAAAG GTATCCGAGG CGGGGGGACT GCTCGTAGTG TTTTTAGCTG

2501  GCTCAAGTCA GAGGTGGCGA AACCCGACAG GACTATAAAG ATACCAGGCG
      CGAGTTCAGT CTCCACCGCT TTGGGCTGTC CTGATATTTC TATGGTCCGC

2551  TTTCCCCCTG GAAGCTCCCT CGTGCGCTCT CCTGTTCCGA CCCTGCCGCT
      AAAGGGGGAC CTTCGAGGGA GCACGCGAGA GGACAAGGCT GGGACGGCGA

2601  TACCGGATAC CTGTCCGCCT TTCTCCCTTC GGGAAGCGTG GCGCTTTCTC
      ATGGCCTATG GACAGGCGGA AAGAGGGAAG CCCTTCGCAC CGCGAAAGAG

2651  AATGCTCACG CTGTAGGTAT CTCAGTTCGG TGTAGGTCGT TCGCTCCAAG
      TTACGAGTGC GACATCCATA GAGTCAAGCC ACATCCAGCA AGCGAGGTTC

2701  CTGGGCTGTG TGCACGAACC CCCCGTTCAG CCCGACCGCT GCGCCTTATC
      GACCCGACAC ACGTGCTTGG GGGGCAAGTC GGGCTGGCGA CGCGGAATAG
```

FIG. 1D

```
2751  CGGTAACTAT CGTCTTGAGT CCAACCCGGT AAGACACGAC TTATCGCCAC
      GCCATTGATA GCAGAACTCA GGTTGGGCCA TTCTGTGCTG AATAGCGGTG

2801  TGGCAGCAGC CACTGGTAAC AGGATTAGCA GAGCGAGGTA TGTAGGCGGT
      ACCGTCGTCG GTGACCATTG TCCTAATCGT CTCGCTCCAT ACATCCGCCA

2851  GCTACAGAGT TCTTGAAGTG GTGGCCTAAC TACGGCTACA CTAGAAGGAC
      CGATGTCTCA AGAACTTCAC CACCGGATTG ATGCCGATGT GATCTTCCTG

2901  AGTATTTGGT ATCTGCGCTC TGCTGAAGCC AGTTACCTTC GGAAAAAGAG
      TCATAAACCA TAGACGCGAG ACGACTTCGG TCAATGGAAG CCTTTTTCTC

2951  TTGGTAGCTC TTGATCCGGC AAACAAACCA CCGCTGGTAG CGGTGGTTTT
      AACCATCGAG AACTAGGCCG TTTGTTTGGT GGCGACCATC GCCACCAAAA

3001  TTTGTTTGCA AGCAGCAGAT TACGCGCAGA AAAAAAGGAT CTCAAGAAGA
      AAACAAACGT TCGTCGTCTA ATGCGCGTCT TTTTTTCCTA GAGTTCTTCT

3051  TCCTTTGATC TTTTCTACGG GGTCTGACGC TCAGTGGAAC GAAAACTCAC
      AGGAAACTAG AAAAGATGCC CCAGACTGCG AGTCACCTTG CTTTTGAGTG

3101  GTTAAGGGAT TTTGGTCATG AGATTATCAA AAAGGATCTT CACCTAGATC
      CAATTCCCTA AAACCAGTAC TCTAATAGTT TTTCCTAGAA GTGGATCTAG

3151  CTTTTAAATT AAAAATGAAG TTTTAAATCA ATCTAAAGTA TATATGAGTA
      GAAAATTTAA TTTTTACTTC AAAATTTAGT TAGATTTCAT ATATACTCAT

3201  AACTTGGTCT GACAGTTACC AATGCTTAAT CAGTGAGGCA CCTATCTCAG
      TTGAACCAGA CTGTCAATGG TTACGAATTA GTCACTCCGT GGATAGAGTC

3251  CGATCTGTCT ATTTCGTTCA TCCATAGTTG CCTGACTCCC CGTCGTGTAG
      GCTAGACAGA TAAAGCAAGT AGGTATCAAC GGACTGAGGG GCAGCACATC

3301  ATAACTACGA TACGGGAGGG CTTACCATCT GGCCCCAGTG CTGCAATGAT
      TATTGATGCT ATGCCCTCCC GAATGGTAGA CCGGGGTCAC GACGTTACTA

3351  ACCGCGAGAC CCACGCTCAC CGGCTCCAGA TTTATCAGCA ATAAACCAGC
      TGGCGCTCTG GGTGCGAGTG GCCGAGGTCT AAATAGTCGT TATTTGGTCG

3401  CAGCCGGAAG GGCCGAGCGC AGAAGTGGTC CTGCAACTTT ATCCGCCTCC
      GTCGGCCTTC CCGGCTCGCG TCTTCACCAG GACGTTGAAA TAGGCGGAGG

3451  ATCCAGTCTA TTAATTGTTG CCGGGAAGCT AGAGTAAGTA GTTCGCCAGT
      TAGGTCAGAT AATTAACAAC GGCCCTTCGA TCTCATTCAT CAAGCGGTCA

3501  TAATAGTTTG CGCAACGTTG TTGCCATTGC TACAGGCATC GTGGTGTCAC
      ATTATCAAAC GCGTTGCAAC AACGGTAACG ATGTCCGTAG CACCACAGTG

3551  GCTCGTCGTT TGGTATGGCT TCATTCAGCT CCGGTTCCCA ACGATCAAGG
      CGAGCAGCAA ACCATACCGA AGTAAGTCGA GGCCAAGGGT TGCTAGTTCC

3601  CGAGTTACAT GATCCCCCAT GTTGTGCAAA AAAGCGGTTA GCTCCTTCGG
      GCTCAATGTA CTAGGGGGTA CAACACGTTT TTTCGCCAAT CGAGGAAGCC

3651  TCCTCCGATC GTTGTCAGAA GTAAGTTGGC CGCAGTGTTA TCACTCATGG
      AGGAGGCTAG CAACAGTCTT CATTCAACCG GCGTCACAAT AGTGAGTACC
```

FIG. 1E

```
3701  TTATGGCAGC ACTGCATAAT TCTCTTACTG TCATGCCATC CGTAAGATGC
      AATACCGTCG TGACGTATTA AGAGAATGAC AGTACGGTAG GCATTCTACG

3751  TTTTCTGTGA CTGGTGAGTA CTCAACCAAG TCATTCTGAG AATAGTGTAT
      AAAAGACACT GACCACTCAT GAGTTGGTTC AGTAAGACTC TTATCACATA

3801  GCGGCGACCG AGTTGCTCTT GCCCGGCGTC AATACGGGAT AATACCGCGC
      CGCCGCTGGC TCAACGAGAA CGGGCCGCAG TTATGCCCTA TTATGGCGCG

3851  CACATAGCAG AACTTTAAAA GTGCTCATCA TTGGAAAACG TTCTTCGGGG
      GTGTATCGTC TTGAAATTTT CACGAGTAGT AACCTTTTGC AAGAAGCCCC

3901  CGAAAACTCT CAAGGATCTT ACCGCTGTTG AGATCCAGTT CGATGTAACC
      GCTTTTGAGA GTTCCTAGAA TGGCGACAAC TCTAGGTCAA GCTACATTGG

3951  CACTCGTGCA CCCAACTGAT CTTCAGCATC TTTTACTTTC ACCAGCGTTT
      GTGAGCACGT GGGTTGACTA GAAGTCGTAG AAAATGAAAG TGGTCGCAAA

4001  CTGGGTGAGC AAAAACAGGA AGGCAAAATG CCGCAAAAAA GGGAATAAGG
      GACCCACTCG TTTTTGTCCT TCCGTTTTAC GGCGTTTTTT CCCTTATTCC

4051  GCGACACGGA AATGTTGAAT ACTCATACTC TTCCTTTTTC AATATTATTG
      CGCTGTGCCT TTACAACTTA TGAGTATGAG AAGGAAAAAG TTATAATAAC

4101  AAGCATTTAT CAGGGTTATT GTCTCATGAG CGGATACATA TTTGAATGTA
      TTCGTAAATA GTCCCAATAA CAGAGTACTC GCCTATGTAT AAACTTACAT

4151  TTTAGAAAAA TAAACAAATA GGGGTTCCGC GCACATTTCC CCGAAAAGTG
      AAATCTTTTT ATTTGTTTAT CCCCAAGGCG CGTGTAAAGG GGCTTTTCAC

4201  CCACCTGACG TCTAAGAAAC CATTATTATC ATGACATTAA CCTATAAAAA
      GGTGGACTGC AGATTCTTTG GTAATAATAG TACTGTAATT GGATATTTTT

4251  TAGGCGTATC ACGAGGCCCT TTCGTC
      ATCCGCATAG TGCTCCGGGA AAGCAG
```

FIG. 1F

```
SEQ ID NO:2  1  TCGCGCGTTT CGGTGATGAC GGTGAAAACC TCTGACACAT GCAGCTCCCG
                AGCGCGCAAA GCCACTACTG CCACTTTTGG AGACTGTGTA CGTCGAGGGC

51 GAGACGGTCA CAGCTTGTCT GTAAGCGGAT GCCGGGAGCA GACAAGCCCG
                CTCTGCCAGT GTCGAACAGA CATTCGCCTA CGGCCCTCGT CTGTTCGGGC

101 TCAGGGCGCG TCAGCGGGTG TTGGCGGGTG TCGGGCTGG  CTTAACTATG
                AGTCCCGCGC AGTCGCCCAC AACCGCCCAC AGCCCCGACC GAATTGATAC
```
                                                       HindIII
                                                       --------
```
            151 CGGCATCAGA GCAGATTGTA CTGAGAGTGC ACCATATGAA GCTTTTTGCA
                GCCGTAGTCT CGTCTAACAT GACTCTCACG TGGTATACTT CGAAAAACGT
```
                       StuI
                       -------
                       AatI
                       -------
```
            201 AAAGCCTAGG CCTCCAAAAA AGCCTCCTCA CTACTTCTGG AATAGCTCAG
                TTTCGGATCC GGAGGTTTTT TCGGAGGAGT GATGAAGACC TTATCGAGTC
```
                         SfiI
                         --------------
```
            251 AGGCCGAGGC GGCCTCGGCC TCTGCATAAA TAAAAAAAAT TAGTCAGCCA
                TCCGGCTCCG CCGGAGCCGG AGACGTATTT ATTTTTTTTA ATCAGTCGGT 301 TGGGGCGGAG AATGGGCGGA ACTGGGCGGG GAGGGAATTA TTGGCTATTG
                ACCCCGCCTC TTACCCGCCT TGACCCGCCC CTCCCTTAAT AACCGATAAC 351 GCCATTGCAT ACGTTGTATC TATATCATAA TATGTACATT TATATTGGCT
                CGGTAACGTA TGCAACATAG ATATAGTATT ATACATGTAA ATATAACCGA 401 CATGTCCAAT ATGACCGCCA TGTTGACATT GATTATTGAC TAGTTATTAA
                GTACAGGTTA TACTGGCGGT ACAACTGTAA CTAATAACTG ATCAATAATT 451 TAGTAATCAA TTACGGGGTC ATTAGTTCAT AGCCCATATA TGGAGTTCCG
                ATCATTAGTT AATGCCCCAG TAATCAAGTA TCGGGTATAT ACCTCAAGGC 501 CGTTACATAA CTTACGGTAA ATGGCCCGCC TGGCTGACCG CCCAACGACC
                GCAATGTATT GAATGCCATT TACCGGGCGG ACCGACTGGC GGGTTGCTGG 551 CCCGCCCATT GACGTCAATA ATGACGTATG TTCCCATAGT AACGCCAATA
                GGGCGGGTAA CTGCAGTTAT TACTGCATAC AAGGGTATCA TTGCGGTTAT 601 GGGACTTTCC ATTGACGTCA ATGGGTGGAG TATTTACGGT AAACTGCCCA
                CCCTGAAAGG TAACTGCAGT TACCCACCTC ATAAATGCCA TTTGACGGGT 651 CTTGGCAGTA CATCAAGTGT ATCATATGCC AAGTCCGCCC CCTATTGACG
                GAACCGTCAT GTAGTTCACA TAGTATACGG TTCAGGCGGG GGATAACTGC 701 TCAATGACGG TAAATGGCCC GCCTGGCATT ATGCCCAGTA CATGACCTTA
                AGTTACTGCC ATTTACCGGG CGGACCGTAA TACGGGTCAT GTACTGGAAT
```
                                                   SnaBI
                                                   --------
```
            751 CGGGACTTTC CTACTTGGCA GTACATCTAC GTATTAGTCA TCGCTATTAC
                GCCCTGAAAG GATGAACCGT CATGTAGATG CATAATCAGT AGCGATAATG
```

FIG. 2B

```
 801  CATGGTGATG CGGTTTTGGC AGTACACCAA TGGGCGTGGA TAGCGGTTTG
      GTACCACTAC GCCAAAACCG TCATGTGGTT ACCCGCACCT ATCGCCAAAC

851  ACTCACGGGG ATTTCCAAGT CTCCACCCCA TTGACGTCAA TGGGAGTTTG
      TGAGTGCCCC TAAAGGTTCA GAGGTGGGGT AACTGCAGTT ACCCTCAAAC

901  TTTTGGCACC AAAATCAACG GGACTTTCCA AAATGTCGTA ATAACCCCGC
      AAAACCGTGG TTTTAGTTGC CCTGAAAGGT TTTACAGCAT TATTGGGGCG

951  CCCGTTGACG CAAATGGGCG GTAGGCGTGT ACGGTGGGAG GTCTATATAA
      GGGCAACTGC GTTTACCCGC CATCCGCACA TGCCACCCTC CAGATATATT

1001  GCAGAGCTCG TTTAGTGAAC CGTCAGATCG CCTGGAGACG CCATCCACGC
      CGTCTCGAGC AAATCACTTG GCAGTCTAGC GGACCTCTGC GGTAGGTGCG
```

XmaIII
                                                    ------
                                                    SacII
                                                    ------
                                                    KspI
                                                    ------
                                                    EclXI
                                                    ------
                                                    EagI
                                                    ------

```
1051  TGTTTTGACC TCCATAGAAG ACACCGGGAC CGATCCAGCC TCCGCGGCCG
      ACAAAACTGG AGGTATCTTC TGTGGCCCTG GCTAGGTCGG AGGCGCCGGC

1101  GGAACGGTGC ATTGAACGC  GGATTCCCCG TGCCAAGAGT GACGTAAGTA
      CCTTGCCACG TAACCTTGCG CCTAAGGGGC ACGGTTCTCA CTGCATTCAT
```

Ppu10I
                                      ------
                                      NsiI
                                      ------

```
1151  CCGCCTATAG ACTCTATAGG CACACCCCTT TGGCTCTTAT GCATGCTATA
      GGCGGATATC TGAGATATCC GTGTGGGGAA ACCGAGAATA CGTACGATAT

1201  CTGTTTTTGG CTTGGGGCCT ATACACCCCC GCTCCTTATG CTATAGGTGA
      GACAAAAACC GAACCCCGGA TATGTGGGGG CGAGGAATAC GATATCCACT
```

EspI
             ---------
             CelII
             ---------
             Bpu1102I
             ---------

```
1251  TGGTATAGCT TAGCCTATAG GTGTGGGTTA TTGACCATTA TTGACCACTC
      ACCATATCGA ATCGGATATC CACACCCAAT AACTGGTAAT AACTGGTGAG

1301  CCCTATTGGT GACGATACTT TCCATTACTA ATCCATAACA TGGCTCTTTG
      GGGATAACCA CTGCTATGAA AGGTAATGAT TAGGTATTGT ACCGAGAAAC

1351  CCACAACTAT CTCTATTGGC TATATGCCAA TACTCTGTCC TTCAGAGACT
      GGTGTTGATA GAGATAACCG ATATACGGTT ATGAGACAGG AAGTCTCTGA

1401  GACACGGACT CTGTATTTTT ACAGGATGGG GTCCATTTAT TATTTACAAA
      CTGTGCCTGA GACATAAAAA TGTCCTACCC CAGGTAAATA ATAAATGTTT
```

FIG. 2C

```
1451  TTCACATATA CAACAACGCC GTCCCCCGTG CCCGCAGTTT TTATTAAACA
      AAGTGTATAT GTTGTTGCGG CAGGGGGCAC GGGCGTCAAA AATAATTTGT
```

MroI
                                              ~~~~~
                                              BspEI
                                              ------
                                              BseAI
                                              ~~~~~~
                                              AccIII
                                              ~~~~~

```
1501  TAGCGTGGGA TCTCCGACAT CTCGGGTACG TGTTCCGGAC ATGGGCTCTT
      ATCGCACCCT AGAGGCTGTA GAGCCCATGC ACAAGGCCTG TACCCGAGAA

1551  CTCCGGTAGC GGCGGAGCTT CCACATCCGA GCCCTGGTCC CATCCGTCCA
      GAGGCCATCG CCGCCTCGAA GGTGTAGGCT CGGGACCAGG GTAGGCAGGT

1601  GCGGCTCATG GTCGCTCGGC AGCTCCTTGC TCCTAACAGT GGAGGCCAGA
      CGCCGAGTAC CAGCGAGCCG TCGAGGAACG AGGATTGTCA CCTCCGGTCT

1651  CTTAGGCACA GCACAATGCC CACCACCACC AGTGTGCCGC ACAAGGCCGT
      GAATCCGTGT CGTGTTACGG GTGGTGGTGG TCACACGGCG TGTTCCGGCA

1701  GGCGGTAGGG TATGTGTCTG AAAATGAGCT CGGAGATTGG GCTCGCACCT
      CCGCCATCCC ATACACAGAC TTTTACTCGA GCCTCTAACC CGAGCGTGGA
```

BfrI
              -------
              AflII                                   PvuII
              ~~~~~~~                                 ~~~~~

```
1751  GGACGCAGAT GGAAGACTTA AGGCAGCGGC AGAAGAAGAT GCAGGCAGCT
      CCTGCGTCTA CCTTCTGAAT TCCGTCGCCG TCTTCTTCTA CGTCCGTCGA
```

PvuII                                             HpaI
      ~                                                 ~

```
1801  GAGTTGTTGT ATTCTGATAA GAGTCAGAGG TAACTCCCGT TGCGGTGCTG
      CTCAACAACA TAAGACTATT CTCAGTCTCC ATTGAGGGCA ACGCCACGAC
```

HpaI
      ~~~~~

```
1851  TTAACGGTGG AGGGCAGTGT AGTCTGAGCA GTACTCGTTG CTGCCGCGCG
      AATTGCCACC TCCCGTCACA TCAGACTCGT CATGAGCAAC GACGGCGCGC

1901  CGCCACCAGA CATAATAGCT GACAGACTAA CAGACTGTTC CTTTCCATGG
      GCGGTGGTCT GTATTATCGA CTGTCTGATT GTCTGACAAG GAAAGGTACC
```

+2                              SEQ ID NO:3   M   Q   W   N
                   SalI
                   ~~~~~

```
1951  GTCTTTTCTG CAGTCACCGT CGTCGACCTA AGAATTCATG CAGTGGAACT
      CAGAAAAGAC GTCAGTGGCA GCAGCTGGAT TCTTAAGTAC GTCACCTTGA
```

+2  S   T   A   F   H   Q   T   L   Q   D   P   R   V   R   G   L   Y
```
2001  CCACTGCCTT CCACCAAACT CTGCAGGATC CCAGAGTCAG GGGTCTGTAT
      GGTGACGGAA GGTGGTTTGA GACGTCCTAG GGTCTCAGTC CCCAGACATA
```

FIG. 2D

```
      +2   L  P  A  G    G  S  S     S  G  T     V  N  P     A  P  N  I
     2051  CTTCCTGCTG  GTGGCTCCAG  TTCAGGAACA  GTAAACCCTG  CTCCGAATAT
           GAAGGACGAC  CACCGAGGTC  AAGTCCTTGT  CATTTGGGAC  GAGGCTTATA

+2   A  S  H     I  S  S  I     S  A  R     T  G  D     P  V  T
     2101  TGCCTCTCAC  ATCTCGTCAA  TCTCCGCGAG  GACTGGGGAC  CCTGTGACGA
           ACGGAGAGTG  TAGAGCAGTT  AGAGGCGCTC  CTGACCCCTG  GGACACTGCT

+2   N  M  E  N     I  T  S     G  F  L  G     P  L  L  V  L  Q
     2151  ACATGGAGAA  CATCACATCA  GGATTCCTAG  GACCCCTGCT  CGTGTTACAG
           TGTACCTCTT  GTAGTGTAGT  CCTAAGGATC  CTGGGGACGA  GCACAATGTC

+2   A  G  F  F     L  L  T     R  I  L     T  I  P  Q     S  L  D
     2201  GCGGGGTTTT  TCTTGTTGAC  AAGAATCCTC  ACAATACCGC  AGAGTCTAGA
           CGCCCCAAAA  AGAACAACTG  TTCTTAGGAG  TGTTATGGCG  TCTCAGATCT

+2   S  W  W     T  S  L  N     F  L  G     G  S  P     V  C  L
     2251  CTCGTGGTGG  ACTTCTCTCA  ATTTTCTAGG  GGGATCTCCC  GTGTGTCTTG
           GAGCACCACC  TGAAGAGAGT  TAAAAGATCC  CCCTAGAGGG  CACACAGAAC

+2   G  Q  N  S     Q  S  P     T  S  N     H  S  P  T     S  C  P
     2301  GCCAAAATTC  GCAGTCCCCA  ACCTCCAATC  ACTCACCAAC  CTCCTGTCCT
           CGGTTTTAAG  CGTCAGGGGT  TGGAGGTTAG  TGAGTGGTTG  GAGGACAGGA

+2   P  I  C  P     G  Y  R     W  M  C     L  R  R  F     I  I  F
     2351  CCAATTTGTC  CTGGTTATCG  CTGGATGTGT  CTGCGGCGTT  TTATCATATT
           GGTTAAACAG  GACCAATAGC  GACCTACACA  GACGCCGCAA  AATAGTATAA

+2    L  F  I     L  L  C     L  I  F     L  L  V     L  L  D
     2401  CCTCTTCATC  CTGCTGCTAT  GCCTCATCTT  CTTATTGGTT  CTTCTGGATT
           GGAGAAGTAG  GACGACGATA  CGGAGTAGAA  GAATAACCAA  GAAGACCTAA

+2   Y  Q  G  M     L  P  V     C  P  L  I     P  G  S     T  T  T
     2451  ATCAAGGTAT  GTTGCCCGTT  TGTCCTCTAA  TTCCAGGATC  AACAACAACC
           TAGTTCCATA  CAACGGGCAA  ACAGGAGATT  AAGGTCCTAG  TTGTTGTTGG

+2   S  T  G  P    C  K  T     C  T  T     P  A  Q     G  N  S  M
                                      BstAP I
                                      ---------
                                      BspMI                EcoNI
                                      --------             ------------
     2501  AGTACGGGAC  CATGCAAAAC  CTGCACGACT  CCTGCTCAAG  GCAACTCTAT
           TCATGCCCTG  GTACGTTTTG  GACGTGCTGA  GGACGAGTTC  CGTTGAGATA
                                      BsgI
                                      ------

+2   F  P  S     C  C  C  T     K  P  T     D  G  N     C  T  C
     2551  GTTTCCCTCA  TGTTGCTGTA  CAAAACCTAC  GGATGGAAAT  TGCACCTGTA
           CAAAGGGAGT  ACAACGACAT  GTTTTGGATG  CCTACCTTTA  ACGTGGACAT

+2    I  P  I  P     S  S  W     A  F  A  K     Y  L  W     E  W  A
                               BstXI
                               --------------
     2601  TTCCCATCCC  ATCGTCCTGG  GCTTTCGCAA  AATACCTATG  GGAGTGGGCC
           AAGGGTAGGG  TAGCAGGACC  CGAAAGCGTT  TTATGGATAC  CCTCACCCGG
```

FIG. 2E

```
       +2  S   V   R   F   S   W   L   S   L   L   V   P   F   V   Q   W   F
     2651 TCAGTCCGTT TCTCTTGGCT CAGTTTACTA GTGCCATTTG TTCAGTGGTT
          AGTCAGGCAA AGAGAACCGA GTCAAATGAT CACGGTAAAC AAGTCACCAA

+2  V   G   L   S   P   T   V   W   L   S   A   I   W   M   M   W
     2701 CGTAGGGCTT TCCCCCACTG TTTGGCTTTC AGCTATATGG ATGATGTGGT
          GCATCCCGAA AGGGGGTGAC AAACCGAAAG TCGATATACC TACTACACCA

+2  Y   W   G   P   S   L   Y   S   I   V   S   P   F   I   P   L   L
     2751 ATTGGGGGCC AAGTCTGTAC AGCATCGTGA GTCCCTTTAT ACCGCTGTTA
          TAACCCCCGG TTCAGACATG TCGTAGCACT CAGGGAAATA TGGCGACAAT

+2  P   I   F   F   C   L   W   V   Y   I   *
                                     BstZ17 I                      XhoI
                                     -------                       ------
                                     Bst1107I                      PaeR7I
                                     --------                      ------
     2801 CCAATTTTCT TTTGTCTCTG GGTATACATT TAAGAATTCA GACTCGAGCA
          GGTTAAAAGA AAACAGAGAC CCATATGTAA ATTCTTAAGT CTGAGCTCGT

AscI       EcoRV              MluI
                    --------   ------             --------
     2851 AGTCTAGAAA GGCGCGCCAA GATATCAAGG ATCCACTACG CGTTAGAGCT
          TCAGATCTTT CCGCGCGGTT CTATAGTTCC TAGGTGATGC GCAATCTCGA

BclI
          ------
     2901 CGCTGATCAG CCTCGACTGT GCCTTCTAGT TGCCAGCCAT CTGTTGTTTG
          GCGACTAGTC GGAGCTGACA CGGAAGATCA ACGGTCGGTA GACAACAAAC

2951 CCCCTCCCCC GTGCCTTCCT TGACCCTGGA AGGTGCCACT CCCACTGTCC
          GGGGAGGGGG CACGGAAGGA ACTGGGACCT TCCACGGTGA GGGTGACAGG

3001 TTTCCTAATA AAATGAGGAA ATTGCATCGC ATTGTCTGAG TAGGTGTCAT
          AAAGGATTAT TTTACTCCTT TAACGTAGCG TAACAGACTC ATCCACAGTA

3051 TCTATTCTGG GGGGTGGGGT GGGGCAGGAC AGCAAGGGGG AGGATTGGGA
          AGATAAGACC CCCCACCCCA CCCCGTCCTG TCGTTCCCCC TCCTAACCCT

3101 AGACAATAGC AGGCATGCTG GGGAGCTCTT CCGCTTCCTC GCTCACTGAC
          TCTGTTATCG TCCGTACGAC CCCTCGAGAA GGCGAAGGAG CGAGTGACTG

3151 TCGCTGCGCT CGGTCGTTCG GCTGCGGCGA GCGGTATCAG CTCACTCAAA
          AGCGACGCGA GCCAGCAAGC CGACGCCGCT CGCCATAGTC GAGTGAGTTT

Pci I
                                                                  ---
     3201 GGCGGTAATA CGGTTATCCA CAGAATCAGG GGATAACGCA GGAAAGAACA
          CCGCCATTAT GCCAATAGGT GTCTTAGTCC CCTATTGCGT CCTTTCTTGT

Pci I
          ---
     3251 TGTGAGCAAA AGGCCAGCAA AAGGCCAGGA ACCGTAAAAA GGCCGCGTTG
          ACACTCGTTT TCCGGTCGTT TTCCGGTCCT TGGCATTTTT CCGGCGCAAC

3301 CTGGCGTTTT TCCATAGGCT CCGCCCCCCT GACGAGCATC ACAAAAATCG
          GACCGCAAAA AGGTATCCGA GGCGGGGGGA CTGCTCGTAG TGTTTTTAGC
```

FIG. 2F

```
3351  ACGCTCAAGT CAGAGGTGGC GAAACCCGAC AGGACTATAA AGATACCAGG
      TGCGAGTTCA GTCTCCACCG CTTTGGGCTG TCCTGATATT TCTATGGTCC

3401  CGTTTCCCCC TGGAAGCTCC CTCGTGCGCT CTCCTGTTCC GACCCTGCCG
      GCAAAGGGGG ACCTTCGAGG GAGCACGCGA GAGGACAAGG CTGGGACGGC

HaeII
                                                          ~~~~~~
3451  CTTACCGGAT ACCTGTCCGC CTTTCTCCCT TCGGGAAGCG TGGCGCTTTC
      GAATGGCCTA TGGACAGGCG GAAAGAGGGA AGCCCTTCGC ACCGCGAAAG

3501  TCAATGCTCA CGCTGTAGGT ATCTCAGTTC GGTGTAGGTC GTTCGCTCCA
      AGTTACGAGT GCGACATCCA TAGAGTCAAG CCACATCCAG CAAGCGAGGT

3551  AGCTGGGCTG TGTGCACGAA CCCCCCGTTC AGCCCGACCG CTGCGCCTTA
      TCGACCCGAC ACACGTGCTT GGGGGGCAAG TCGGGCTGGC GACGCGGAAT

3601  TCCGGTAACT ATCGTCTTGA GTCCAACCCG GTAAGACACG ACTTATCGCC
      AGGCCATTGA TAGCAGAACT CAGGTTGGGC CATTCTGTGC TGAATAGCGG

3651  ACTGGCAGCA GCCACTGGTA ACAGGATTAG CAGAGCGAGG TATGTAGGCG
      TGACCGTCGT CGGTGACCAT TGTCCTAATC GTCTCGCTCC ATACATCCGC

3701  GTGCTACAGA GTTCTTGAAG TGGTGGCCTA ACTACGGCTA CACTAGAAGG
      CACGATGTCT CAAGAACTTC ACCACCGGAT TGATGCCGAT GTGATCTTCC

3751  ACAGTATTTG GTATCTGCGC TCTGCTGAAG CCAGTTACCT TCGGAAAAAG
      TGTCATAAAC CATAGACGCG AGACGACTTC GGTCAATGGA AGCCTTTTTC

3801  AGTTGGTAGC TCTTGATCCG GCAAACAAAC CACCGCTGGT AGCGGTGGTT
      TCAACCATCG AGAACTAGGC CGTTTGTTTG GTGGCGACCA TCGCCACCAA

3851  TTTTTGTTTG CAAGCAGCAG ATTACGCGCA GAAAAAAAGG ATCTCAAGAA
      AAAAACAAAC GTTCGTCGTC TAATGCGCGT CTTTTTTTCC TAGAGTTCTT

3901  GATCCTTTGA TCTTTTCTAC GGGGTCTGAC GCTCAGTGGA ACGAAAACTC
      CTAGGAAACT AGAAAAGATG CCCCAGACTG CGAGTCACCT TGCTTTTGAG

3951  ACGTTAAGGG ATTTTGGTCA TGAGATTATC AAAAAGGATC TTCACCTAGA
      TGCAATTCCC TAAAACCAGT ACTCTAATAG TTTTTCCTAG AAGTGGATCT

4001  TCCTTTTAAA TTAAAAATGA AGTTTTAAAT CAATCTAAAG TATATATGAG
      AGGAAAATTT AATTTTTACT TCAAAATTTA GTTAGATTTC ATATATACTC

4051  TAAACTTGGT CTGACAGTTA CCAATGCTTA ATCAGTGAGG CACCTATCTC
      ATTTGAACCA GACTGTCAAT GGTTACGAAT TAGTCACTCC GTGGATAGAG

Eam1105I
                                                     --------------
                                                     AspEI
                                                     --------------
4101  AGCGATCTGT CTATTTCGTT CATCCATAGT TGCCTGACTC CCCGTCGTGT
      TCGCTAGACA GATAAAGCAA GTAGGTATCA ACGGACTGAG GGGCAGCACA

4151  AGATAACTAC GATACGGGAG GGCTTACCAT CTGGCCCCAG TGCTGCAATG
      TCTATTGATG CTATGCCCTC CCGAATGGTA GACCGGGGTC ACGACGTTAC
```

FIG. 2G

```
                              Cfr10I
                              ------
                                BsrFI
                                ------
    4201  ATACCGCGAG ACCCACGCTC ACCGGCTCCA GATTTATCAG CAATAAACCA
          TATGGCGCTC TGGGTGCGAG TGGCCGAGGT CTAAATAGTC GTTATTTGGT
                 BsaI
                 -------

4251  GCCAGCCGGA AGGGCCGAGC GCAGAAGTGG TCCTGCAACT TTATCCGCCT
          CGGTCGGCCT TCCCGGCTCG CGTCTTCACC AGGACGTTGA AATAGGCGGA

4301  CCATCCAGTC TATTAATTGT TGCCGGGAAG CTAGAGTAAG TAGTTCGCCA
          GGTAGGTCAG ATAATTAACA ACGGCCCTTC GATCTCATTC ATCAAGCGGT

FspI
                    ------
                     AviII
                     ------
                      AosI
                      ------
    4351  GTTAATAGTT TGCGCAACGT TGTTGCCATT GCTACAGGCA TCGTGGTGTC
          CAATTATCAA ACGCGTTGCA ACAACGGTAA CGATGTCCGT AGCACCACAG

4401  ACGCTCGTCG TTTGGTATGG CTTCATTCAG CTCCGGTTCC CAACGATCAA
          TGCGAGCAGC AAACCATACC GAAGTAAGTC GAGGCCAAGG GTTGCTAGTT

4451  GGCGAGTTAC ATGATCCCCC ATGTTGTGCA AAAAAGCGGT TAGCTCCTTC
          CCGCTCAATG TACTAGGGGG TACAACACGT TTTTTCGCCA ATCGAGGAAG

PvuI
             --------
    4501  GGTCCTCCGA TCGTTGTCAG AAGTAAGTTG GCCGCAGTGT TATCACTCAT
          CCAGGAGGCT AGCAACAGTC TTCATTCAAC CGGCGTCACA ATAGTGAGTA

4551  GGTTATGGCA GCACTGCATA ATTCTCTTAC TGTCATGCCA TCCGTAAGAT
          CCAATACCGT CGTGACGTAT TAAGAGAATG ACAGTACGGT AGGCATTCTA

4601  GCTTTTCTGT GACTGGTGAG TACTCAACCA AGTCATTCTG AGAATAGTGT
          CGAAAAGACA CTGACCACTC ATGAGTTGGT TCAGTAAGAC TCTTATCACA

BcgI
            ~~~~~~~~~~~~~~
    4651  ATGCGGCGAC CGAGTTGCTC TTGCCCGGCG TCAATACGGG ATAATACCGC
          TACGCCGCTG GCTCAACGAG AACGGGCCGC AGTTATGCCC TATTATGGCG

XmnI
                                                   ~~~~~~~~~~~
                                                   Asp700
                                                   ~~~~~~~~~~~
    4701  GCCACATAGC AGAACTTTAA AAGTGCTCAT CATTGGAAAA CGTTCTTCGG
          CGGTGTATCG TCTTGAAATT TTCACGAGTA GTAACCTTTT GCAAGAAGCC

4751  GGCGAAAACT CTCAAGGATC TTACCGCTGT TGAGATCCAG TTCGATGTAA
          CCGCTTTTGA GAGTTCCTAG AATGGCGACA ACTCTAGGTC AAGCTACATT

4801  CCCACTCGTG CACCCAACTG ATCTTCAGCA TCTTTTACTT TCACCAGCGT
          GGGTGAGCAC GTGGGTTGAC TAGAAGTCGT AGAAAATGAA AGTGGTCGCA
```

FIG. 2H

| | | | | | |
|---|---|---|---|---|---|
| 4851 | TTCTGGGTGA | GCAAAAACAG | GAAGGCAAAA | TGCCGCAAAA | AAGGGAATAA |
| | AAGACCCACT | CGTTTTTGTC | CTTCCGTTTT | ACGGCGTTTT | TTCCCTTATT |
| 4901 | GGGCGACACG | GAAATGTTGA | ATACTCATAC | TCTTCCTTTT | TCAATATTAT |
| | CCCGCTGTGC | CTTTACAACT | TATGAGTATG | AGAAGGAAAA | AGTTATAATA |
| 4951 | TGAAGCATTT | ATCAGGGTTA | TTGTCTCATG | AGCGGATACA | TATTTGAATG |
| | ACTTCGTAAA | TAGTCCCAAT | AACAGAGTAC | TCGCCTATGT | ATAAACTTAC |
| 5001 | TATTTAGAAA | AATAAACAAA | TAGGGGTTCC | GCGCACATTT | CCCCGAAAAG |
| | ATAAATCTTT | TTATTTGTTT | ATCCCCAAGG | CGCGTGTAAA | GGGGCTTTTC |
| 5051 | TGCCACCTGA | CGTCTAAGAA | ACCATTATTA | TCATGACATT | AACCTATAAA |
| | ACGGTGGACT | GCAGATTCTT | TGGTAATAAT | AGTACTGTAA | TTGGATATTT |
| 5101 | AATAGGCGTA | TCACGAGGCC | CTTTCGTC | | |
| | TTATCCGCAT | AGTGCTCCGG | GAAAGCAG | | |

FIG. 2I

```
SEQ ID NO:4  1  TCGCGCGTTT CGGTGATGAC GGTGAAAACC TCTGACACAT GCAGCTCCCG
                AGCGCGCAAA GCCACTACTG CCACTTTTGG AGACTGTGTA CGTCGAGGGC

51  GAGACGGTCA CAGCTTGTCT GTAAGCGGAT GCCGGGAGCA GACAAGCCCG
                CTCTGCCAGT GTCGAACAGA CATTCGCCTA CGGCCCTCGT CTGTTCGGGC

101  TCAGGGCGCG TCAGCGGGTG TTGGCGGGTG TCGGGGCTGG CTTAACTATG
                AGTCCCGCGC AGTCGCCCAC AACCGCCCAC AGCCCCGACC GAATTGATAC

HindIII
                                                            ~~~~~~~
           151  CGGCATCAGA GCAGATTGTA CTGAGAGTGC ACCATATGAA GCTTTTTGCA
                GCCGTAGTCT CGTCTAACAT GACTCTCACG TGGTATACTT CGAAAAACGT StuI
                    ~~~~~~~
                    AatI
                    ~~~~~~~
           201  AAAGCCTAGG CCTCCAAAAA AGCCTCCTCA CTACTTCTGG AATAGCTCAG
                TTTCGGATCC GGAGGTTTTT TCGGAGGAGT GATGAAGACC TTATCGAGTC SfII
                ---------------
           251  AGGCCGAGGC GGCCTCGGCC TCTGCATAAA TAAAAAAAAT TAGTCAGCCA
                TCCGGCTCCG CCGGAGCCGG AGACGTATTT ATTTTTTTTA ATCAGTCGGT 301  TGGGGCGGAG AATGGGCGGA ACTGGGCGGG GAGGGAATTA TTGGCTATTG
                ACCCCGCCTC TTACCCGCCT TGACCCGCCC CTCCCTTAAT AACCGATAAC 351  GCCATTGCAT ACGTTGTATC TATATCATAA TATGTACATT TATATTGGCT
                CGGTAACGTA TGCAACATAG ATATAGTATT ATACATGTAA ATATAACCGA 401  CATGTCCAAT ATGACCGCCA TGTTGACATT GATTATTGAC TAGTTATTAA
                GTACAGGTTA TACTGGCGGT ACAACTGTAA CTAATAACTG ATCAATAATT 451  TAGTAATCAA TTACGGGGTC ATTAGTTCAT AGCCCATATA TGGAGTTCCG
                ATCATTAGTT AATGCCCCAG TAATCAAGTA TCGGGTATAT ACCTCAAGGC 501  CGTTACATAA CTTACGGTAA ATGGCCCGCC TGGCTGACCG CCCAACGACC
                GCAATGTATT GAATGCCATT TACCGGGCGG ACCGACTGGC GGGTTGCTGG 551  CCCGCCCATT GACGTCAATA ATGACGTATG TTCCCATAGT AACGCCAATA
                GGGCGGGTAA CTGCAGTTAT TACTGCATAC AAGGGTATCA TTGCGGTTAT 601  GGGACTTTCC ATTGACGTCA ATGGGTGGAG TATTTACGGT AAACTGCCCA
                CCCTGAAAGG TAACTGCAGT TACCCACCTC ATAAATGCCA TTTGACGGGT 651  CTTGGCAGTA CATCAAGTGT ATCATATGCC AAGTCCGCCC CCTATTGACG
                GAACCGTCAT GTAGTTCACA TAGTATACGG TTCAGGCGGG GGATAACTGC 701  TCAATGACGG TAAATGGCCC GCCTGGCATT ATGCCCAGTA CATGACCTTA
                AGTTACTGCC ATTTACCGGG CGGACCGTAA TACGGGTCAT GTACTGGAAT SnaBI
                                                      ~~~~~~~
           751  CGGGACTTTC CTACTTGGCA GTACATCTAC GTATTAGTCA TCGCTATTAC
                GCCCTGAAAG GATGAACCGT CATGTAGATG CATAATCAGT AGCGATAATG
```

FIG. 3B

```
 801  CATGGTGATC CGGTTTTGGC AGTACACCAA TGGGCGTGGA TAGCGGTTTG
      GTACCACTAC GCCAAAACCG TCATGTGGTT ACCCGCACCT ATCGCCAAAC

851  ACTCACGGGG ATTTCCAAGT CTCCACCCCA TTGACGTCAA TGGGAGTTTG
      TGAGTGCCCC TAAAGGTTCA GAGGTGGGGT AACTGCAGTT ACCCTCAAAC

901  TTTTGGCACC AAAATCAACG GGACTTTCCA AAATGTCGTA ATAACCCCGC
      AAAACCGTGG TTTTAGTTGC CCTGAAAGGT TTTACAGCAT TATTGGGGCG

951  CCCGTTGACG CAAATGGGCG GTAGGCGTGT ACGGTGGGAG GTCTATATAA
      GGGCAACTGC GTTTACCCGC CATCCGCACA TGCCACCCTC CAGATATATT

1001  GCAGAGCTCG TTTAGTGAAC CGTCAGATCG CCTGGAGACG CCATCCACGC
      CGTCTCGAGC AAATCACTTG GCAGTCTAGC GGACCTCTGC GGTAGGTGCG
```

```
                                                    XmaIII
                                                    ------
                                                    SacII
                                                    ------
                                                    KspI
                                                    ------
                                                    EclXI
                                                    ------
                                                    EagI
                                                    ------
```

```
1051  TGTTTTGACC TCCATAGAAG ACACCGGGAC CGATCCAGCC TCCGCGGCCG
      ACAAAACTGG AGGTATCTTC TGTGGCCCTG GCTAGGTCGG AGGCGCCGGC

1101  GGAACGGTGC ATTGAACGC GGATTCCCCG TGCCAAGAGT GACGTAAGTA
      CCTTGCCACG TAACCTTGCG CCTAAGGGGC ACGGTTCTCA CTGCATTCAT
```

```
                                      Ppu10I
                                      -------
                                      NsiI
                                      -------
```

```
1151  CCGCCTATAG ACTCTATAGG CACACCCCTT TGGCTCTTAT GCATGCTATA
      GGCGGATATC TGAGATATCC GTGTGGGGAA ACCGAGAATA CGTACGATAT

1201  CTGTTTTTGG CTTGGGGCCT ATACACCCCC GCTCCTTATG CTATAGGTGA
      GACAAAAACC GAACCCCGGA TATGTGGGGG CGAGGAATAC GATATCCACT
```

```
        EspI
        ---------
        CelII
        ---------
        Bpu1102I
        ---------
```

```
1251  TGGTATAGCT TAGCCTATAG GTGTGGGTTA TTGACCATTA TTGACCACTC
      ACCATATCGA ATCGGATATC CACACCCAAT AACTGGTAAT AACTGGTGAG

1301  CCCTATTGGT GACGATACTT TCCATTACTA ATCCATAACA TGGCTCTTTG
      GGGATAACCA CTGCTATGAA AGGTAATGAT TAGGTATTGT ACCGAGAAAC

1351  CCACAACTAT CTCTATTGGC TATATGCCAA TACTCTGTCC TTCAGAGACT
      GGTGTTGATA GAGATAACCG ATATACGGTT ATGAGACAGG AAGTCTCTGA

1401  GACACGGACT CTGTATTTTT ACAGGATGGG GTCCATTTAT TATTTACAAA
      CTGTGCCTGA GACATAAAAA TGTCCTACCC CAGGTAAATA ATAAATGTTT
```

FIG. 3C

```
1451  TTCACATATA CAACAACGCC GTCCCCCGTG CCCGCAGTTT TTATTAAACA
      AAGTGTATAT GTTGTTGCGG CAGGGGGCAC GGGCGTCAAA AATAATTTGT
```

MroI
                                              ------
                                              BspEI
                                              ------
                                              BseAI
                                              ------
                                              AccIII
                                              ------
```
1501  TAGCGTGGGA TCTCCGACAT CTCGGGTACG TGTTCCGGAC ATGGGCTCTT
      ATCGCACCCT AGAGGCTGTA GAGCCCATGC ACAAGGCCTG TACCCGAGAA

1551  CTCCGGTAGC GGCGGAGCTT CCACATCCGA GCCCTGGTCC CATCCGTCCA
      GAGGCCATCG CCGCCTCGAA GGTGTAGGCT CGGGACCAGG GTAGGCAGGT

1601  GCGGCTCATG GTCGCTCGGC AGCTCCTTGC TCCTAACAGT GGAGGCCAGA
      CGCCGAGTAC CAGCGAGCCG TCGAGGAACG AGGATTGTCA CCTCCGGTCT

1651  CTTAGGCACA GCACAATGCC CACCACCACC AGTGTGCCGC ACAAGGCCGT
      GAATCCGTGT CGTGTTACGG GTGGTGGTGG TCACACGGCG TGTTCCGGCA

1701  GGCGGTAGGG TATGTGTCTG AAAATGAGCT CGGAGATTGG GCTCGCACCT
      CCGCCATCCC ATACACAGAC TTTTACTCGA GCCTCTAACC CGAGCGTGGA
```

BfrI
            -------
            AflII
            -------
```
1751  GGACGCAGAT GGAAGACTTA AGGCAGCGGC AGAAGAAGAT GCAGGCAGCT
      CCTGCGTCTA CCTTCTGAAT TCCGTCGCCG TCTTCTTCTA CGTCCGTCGA
```

HpaI
                                                   -
```
1801  GAGTTGTTGT ATTCTGATAA GAGTCAGAGG TAACTCCCGT TGCGGTGCTG
      CTCAACAACA TAAGACTATT CTCAGTCTCC ATTGAGGGCA ACGCCACGAC
```

HpaI
      -----
```
1851  TTAACGGTGG AGGGCAGTGT AGTCTGAGCA GTACTCGTTG CTGCCGCGCG
      AATTGCCACC TCCCGTCACA TCAGACTCGT CATGAGCAAC GACGGCGCGC

1901  CGCCACCAGA CATAATAGCT GACAGACTAA CAGACTGTTC CTTTCCATGG
      GCGGTGGTCT GTATTATCGA CTGTCTGATT GTCTGACAAG GAAAGGTACC
```

+3                                 SEQ ID NO:5    M  D  A
                            SalI
                            ~~~~
```
1951  GTCTTTTCTG CAGTCACCGT CGTCGACGAA TTCAAGCAAT CATGGATGCA
      CAGAAAAGAC GTCAGTGGCA GCAGCTGCTT AAGTTCGTTA GTACCTACGT
```

+3   M  K  R   G  L  C  C   V  L  L   L  C  G  A   V  F  V
```
2001  ATGAAGAGAG GGCTCTGCTG TGTGCTGCTG CTGTGTGGAG CAGTCTTCGT
      TACTTCTCTC CCGAGACGAC ACACGACGAC GACACACCTC GTCAGAAGCA
```

FIG. 3D

```
      +3   S    P    S    A    S    Y    Q    V    R    N    S    T    G    L    Y    H
                          NheI                                                      PmlI
                          ------                                                    ----
                     Eco47III                                                       PmaCI
                     --------                                                       ----
                      Afe I        SexAI                                            EbrPI
                      -------      --------                                         ----
      2051 TTCGCCCAGC GCTAGCTACC AGGTGCGCAA CAGCACCGGC CTGTACCACG
           AAGCGGGTCG CGATCGATGG TCCACGCGTT GTCGTGGCCG GACATGGTGC
_____

+3   V    T    N    D    C    P    N    S    S    I    V    Y    E    A    A    D    A
           PmlI
           --
           PmaCI
           --
           BbrPI
           --
      2101 TGACCAACGA CTGCCCCAAC AGCAGCATCG TGTACGAGGC CGCCGACGCC
           ACTGGTTGCT GACGGGGTTG TCGTCGTAGC ACATGCTCCG GCGGCTGCGG
_____

+3   I    L    H    T    P    G    C    V    P    C    V    R    E    G    N    A    S
      2151 ATCCTGCACA CCCCCGGCTG CGTGCCCTGC GTGCGCGAGG GCAACGCCAG
           TAGGACGTGT GGGGGCCGAC GCACGGGACG CACGCGCTCC CGTTGCGGTC
_____

+3   R    C    W    V    A    M    T    P    T    V    A    T    R    D    G    K
      2201 CCGCTGCTGG GTGGCCATGA CCCCCACCGT GGCCACCCGC GACGGCAAGC
           GGCGACGACC CACCGGTACT GGGGGTGGCA CCGGTGGGCG CTGCCGTTCG
_____

+3   L    P    A    T    Q    L    R    R    H    I    D    L    L    V    G    S    A
                                                                                         DraIII
                                                                                         -
      2251 TGCCCGCCAC CCAGCTGCGC CGCCACATCG ACCTGCTGGT GGGCAGCGCC
           ACGGGCGGTG GGTCGACGCG GCGGTGTAGC TGGACGACCA CCCGTCGCGG
_____

+3   T    L    C    S    A    L    Y    V    G    D    L    C    G    S    V    F    L
           DraIII
           --------
      2301 ACCCTGTGCA GCGCCCTGTA CGTGGGCGAC CTGTGCGGCA GCGTGTTCCT
           TGGGACACGT CGCGGGACAT GCACCCGCTG GACACGCCGT CGCACAAGGA
_____

+3   V    G    Q    L    F    T    F    S    P    R    R    H    W    T    T    Q
      2351 GGTGGGCCAG CTGTTCACCT TCAGCCCCCG CCGCCACTGG ACCACCCAGG
           CCACCCGGTC GACAAGTGGA AGTCGGGGGC GGCGGTGACC TGGTGGGTCC
_____

+3   G    C    N    C    S    I    Y    P    G    H    I    T    G    H    R    M    A
      2401 GCTGCAACTG CAGCATCTAC CCCGGCCACA TCACCGGCCA CCGCATGGCC
           CGACGTTGAC GTCGTAGATG GGGCCGGTGT AGTGGCCGGT GGCGTACCGG
_____

340 ─┬─SAg
      +3   W    D    M    M    M    N    W    S    P    T    T    M    E    N    I    T    S
      2451 TGGGACATGA TGATGAACTG GAGCCCCACC ACCATGGAGA ACATCACATC
           ACCCTGTACT ACTACTTGAC CTCGGGGTGG TGGTACCTCT TGTAGTGTAG
_____

+3   G    F    L    G    P    L    L    V    L    Q    A    G    F    F    L    L
                     PpuMI
                     --------
      2501 AGGATTCCTA GGACCCCTGC TCGTGTTACA GGCGGGGTTT TCTTGTTGA
           TCCTAAGGAT CCTGGGGACG AGCACAATGT CCGCCCCAAA AGAACAACT
_____
```

FIG. 3E

```
     +3  T   R   I   L   T   l   P    Q   S   L   D   S   W   W    T   S   L
2551     CAAGAATCCT CACAATACCG CAGAGTCTAG ACTCGTGGTG GACTTCTCTC
         GTTCTTAGGA GTGTTATGGC GTCTCAGATC TGAGCACCAC CTGAAGAGAG
```

```
     +3  N   F   L   G    G   S   P    V   C   L    G   Q   N   S    Q   S   P
2601     AATTTTCTAG GGGGATCTCC CGTGTGTCTT GGCCAAAATT CGCAGTCCCC
         TTAAAAGATC CCCCTAGAGG GCACACAGAA CCGGTTTTAA GCGTCAGGGG
```

```
     +3  T   S    N    H   S   P    T    S   C   P    P   I   C    P   G   Y
2651     AACCTCCAAT CACTCACCAA CCTCCTGTCC TCCAATTTGT CCTGGTTATC
         TTGGAGGTTA GTGAGTGGTT GGAGGACAGG AGGTTAAACA GGACCAATAG
```

```
     +3 R   W   M   C   L   R   R    F   I   I   F   L   F   I    L   L   L
2701     GCTGGATGTG TCTGCGGCGT TTTATCATAT TCCTCTTCAT CCTGCTGCTA
         CGACCTACAC AGACGCCGCA AAATAGTATA AGGAGAAGTA GGACGACGAT
```

```
     +3  C   L   I   F    L   L   V    L   L   D   Y   Q   G   M    L   P   V
2751     TGCCTCATCT TCTTATTGGT TCTTCTGGAT TATCAAGGTA TGTTGCCCGT
         ACGGAGTAGA AGAATAACCA AGAAGACCTA ATAGTTCCAT ACAACGGGCA
```

```
     +3    C   P   L    I   P   G    S   T   T   T    S   T   G    P   C   K
                                                                BstAP I
                                                                ~ ~ ~ ~ ~
2801     TTGTCCTCTA ATTCCAGGAT CAACAACAAC CAGTACGGGA CCATGCAAAA
         AACAGGAGAT TAAGGTCCTA GTTGTTGTTG GTCATGCCCT GGTACGTTTT
```

```
     +3 T   C   T   T     P   A   Q    G   N   S   M    F   P   S    C   C   C
        BstAP I           EcoNI
        ~ ~ ~ ~ ~         - - - - - - - - - -
2851     CCTGCACGAC TCCTGCTCAA GGCAACTCTA TGTTTCCCTC ATGTTGCTGT
         GGACGTGCTG AGGACGAGTT CCGTTGAGAT ACAAAGGGAG TACAACGACA
```

```
     +3  T   K   P   T    D   G   N    C   T   C    I   P   I   P    S   S   W
2901     ACAAAACCTA CGGATGGAAA TTGCACCTGT ATTCCCATCC CATCGTCCTG
         TGTTTTGGAT GCCTACCTTT AACGTGGACA TAAGGGTAGG GTAGCAGGAC
```

```
     +3  A   F   A    K   Y   L    W   D   W   A    S   V   R    F   S   W
2951    GGCTTTCGCA AAATACCTAT GGGAGTGGGC CTCAGTCCGT TTCTCTTGGC
         CCGAAAGCGT TTTATGGATA CCCTCACCCG GAGTCAGGCA AAGAGAACCG
```

```
     +3 L   S   L    L   V   P   F   V   Q   W   F    V   G   L    S   P   T
3001     TCAGTTTACT AGTGCCATTT GTTCAGTGGT TCGTAGGGCT TTCCCCCACT
         AGTCAAATGA TCACGGTAAA CAAGTCACCA AGCATCCCGA AAGGGGGTGA
```

```
     +3  V   W   L   S   A   I   W   M   M   W   Y   W   G   P    S   L   Y
3051     GTTTGGCTTT CAGCTATATG GATGATGTGG TATTGGGGGC CAAGTCTGTA
         CAAACCGAAA GTCGATATAC CTACTACACC ATAACCCCCG GTTCAGACAT
```

```
     +3  S   I   V    S   P   F   I    P   L   L    P   I   F    F   C   L
3101     CAGCATCGTG AGTCCCTTTA TACCGCTGTT ACCAATTTTC TTTTGTCTCT
         GTCGTAGCAC TCAGGGAAAT ATGGCGACAA TGGTTAAAAG AAAACAGAGA
```

FIG. 3F

```
      +3  W   V   Y   I   *
           BstZ17 I                    XhoI
           ------                      ------
            Bst1107I                    PaeR7I                      AscI
            ------                      ------                   --------
    3151  GGGTATACAT TTAAGAATTC AGACTCGAGC AAGTCTAGAA AGGCGCGCCA
          CCCATATGTA AATTCTTAAG TCTGAGCTCG TTCAGATCTT TCCGCGCGGT

EcoRV     BamHI    MluI                  BclI
              -----   -------  -------               ------
    3201  AGATATCAAG GATCCACTAC GCGTTAGAGC TCGCTGATCA GCCTCGACTG
          TCTATAGTTC CTAGGTGATG CGCAATCTCG AGCGACTAGT CGGAGCTGAC

3251  TGCCTTCTAG TTGCCAGCCA TCTGTTGTTT GCCCCTCCCC CGTGCCTTCC
          ACGGAAGATC AACGGTCGGT AGACAACAAA CGGGGAGGGG GCACGGAAGG

3301  TTGACCCTGG AAGGTGCCAC TCCCACTGTC CTTTCCTAAT AAAATGAGGA
          AACTGGGACC TTCCACGGTG AGGGTGACAG GAAAGGATTA TTTTACTCCT

3351  AATTGCATCG CATTGTCTGA GTAGGTGTCA TTCTATTCTG GGGGGTGGGG
          TTAACGTAGC GTAACAGACT CATCCACAGT AAGATAAGAC CCCCCACCCC

3401  TGGGGCAGGA CAGCAAGGGG GAGGATTGGG AAGACAATAG CAGGCATGCT
          ACCCCGTCCT GTCGTTCCCC CTCCTAACCC TTCTGTTATC GTCCGTACGA

3451  GGGGAGCTCT TCCGCTTCCT CGCTCACTGA CTCGCTGCGC TCGGTCGTTC
          CCCCTCGAGA AGGCGAAGGA GCGAGTGACT GAGCGACGCG AGCCAGCAAG

3501  GGCTGCGGCG AGCGGTATCA GCTCACTCAA AGGCGGTAAT ACGGTTATCC
          CCGACGCCGC TCGCCATAGT CGAGTGAGTT TCCGCCATTA TGCCAATAGG

Pci I
                                       --------
    3551  ACAGAATCAG GGGATAACGC AGGAAAGAAC ATGTGAGCAA AAGGCCAGCA
          TGTCTTAGTC CCCTATTGCG TCCTTTCTTG TACACTCGTT TTCCGGTCGT

3601  AAAGGCCAGG AACCGTAAAA AGGCCGCGTT GCTGGCGTTT TTCCATAGGC
          TTTCCGGTCC TTGGCATTTT TCCGGCGCAA CGACCGCAAA AAGGTATCCG

3651  TCCGCCCCCC TGACGAGCAT CACAAAAATC GACGCTCAAG TCAGAGGTGG
          AGGCGGGGGG ACTGCTCGTA GTGTTTTTAG CTGCGAGTTC AGTCTCCACC

3701  CGAAACCCGA CAGGACTATA AAGATACCAG GCGTTTCCCC CTGGAAGCTC
          GCTTTGGGCT GTCCTGATAT TTCTATGGTC CGCAAAGGGG GACCTTCGAG

3751  CCTCGTGCGC TCTCCTGTTC CGACCCTGCC GCTTACCGGA TACCTGTCCG
          GGAGCACGCG AGAGGACAAG GCTGGGACGG CGAATGGCCT ATGGACAGGC

3801  CCTTTCTCCC TTCGGGAAGC GTGGCGCTTT CTCAATGCTC ACGCTGTAGG
          GGAAAGAGGG AAGCCCTTCG CACCGCGAAA GAGTTACGAG TGCGACATCC

3851  TATCTCAGTT CGGTGTAGGT CGTTCGCTCC AAGCTGGGCT GTGTGCACGA
          ATAGAGTCAA GCCACATCCA GCAAGCGAGG TTCGACCCGA CACACGTGCT

3901  ACCCCCCGTT CAGCCCGACC GCTGCGCCTT ATCCGGTAAC TATCGTCTTG
          TGGGGGGCAA GTCGGGCTGG CGACGCGGAA TAGGCCATTG ATAGCAGAAC
```

FIG. 3G

```
3951  AGTCCAACCC GGTAAGACAC GACTTATCGC CACTGGCAGC AGCCACTGGT
      TCAGGTTGGG CCATTCTGTG CTGAATAGCG GTGACCGTCG TCGGTGACCA

4001  AACAGGATTA GCAGAGCGAG GTATGTAGGC GGTGCTACAG AGTTCTTGAA
      TTGTCCTAAT CGTCTCGCTC CATACATCCG CCACGATGTC TCAAGAACTT

4051  GTGGTGGCCT AACTACGGCT ACACTAGAAG GACAGTATTT GGTATCTGCG
      CACCACCGGA TTGATGCCGA TGTGATCTTC CTGTCATAAA CCATAGACGC

4101  CTCTGCTGAA GCCAGTTACC TTCGGAAAAA GAGTTGGTAG CTCTTGATCC
      GAGACGACTT CGGTCAATGG AAGCCTTTTT CTCAACCATC GAGAACTAGG

4151  GGCAAACAAA CCACCGCTGG TAGCGGTGGT TTTTTTGTTT GCAAGCAGCA
      CCGTTTGTTT GGTGGCGACC ATCGCCACCA AAAAACAAA CGTTCGTCGT

4201  GATTACGCGC AGAAAAAAAG GATCTCAAGA AGATCCTTTG ATCTTTTCTA
      CTAATGCGCG TCTTTTTTTC CTAGAGTTCT TCTAGGAAAC TAGAAAAGAT

4251  CGGGGTCTGA CGCTCAGTGG AACGAAAACT CACGTTAAGG GATTTTGGTC
      GCCCCAGACT GCGAGTCACC TTGCTTTTGA GTGCAATTCC CTAAAACCAG

4301  ATGAGATTAT CAAAAAGGAT CTTCACCTAG ATCCTTTTAA ATTAAAAATG
      TACTCTAATA GTTTTTCCTA GAAGTGGATC TAGGAAAATT TAATTTTTAC

4351  AAGTTTTAAA TCAATCTAAA GTATATATGA GTAAACTTGG TCTGACAGTT
      TTCAAAATTT AGTTAGATTT CATATATACT CATTTGAACC AGACTGTCAA

4401  ACCAATGCTT AATCAGTGAG GCACCTATCT CAGCGATCTG TCTATTTCGT
      TGGTTACGAA TTAGTCACTC CGTGGATAGA GTCGCTAGAC AGATAAAGCA
```

Eam1105I
                    -------------
                    AspEI
                    -------------

```
4451  TCATCCATAG TTGCCTGACT CCCCGTCGTG TAGATAACTA CGATACGGGA
      AGTAGGTATC AACGGACTGA GGGGCAGCAC ATCTATTGAT GCTATGCCCT

4501  GGGCTTACCA TCTGGCCCCA GTGCTGCAAT GATACCGCGA GACCCACGCT
      CCCGAATGGT AGACCGGGGT CACGACGTTA CTATGGCGCT CTGGGTGCGA
                                                    BsaI
                                                    --------

4551  CACCGGCTCC AGATTTATCA GCAATAAACC AGCCAGCCGG AAGGGCCGAG
      GTGGCCGAGG TCTAAATAGT CGTTATTTGG TCGGTCGGCC TTCCCGGCTC

4601  CGCAGAAGTG GTCCTGCAAC TTTATCCGCC TCCATCCAGT CTATTAATTG
      GCGTCTTCAC CAGGACGTTG AAATAGGCGG AGGTAGGTCA GATAATTAAC

4651  TTGCCGGGAA GCTAGAGTAA GTAGTTCGCC AGTTAATAGT TTGCGCAACG
      AACGGCCCTT CGATCTCATT CATCAAGCGG TCAATTATCA AACGCGTTGC

4701  TTGTTGCCAT TGCTACAGGC ATCGTGGTGT CACGCTCGTC GTTTGGTATG
      AACAACGGTA ACGATGTCCG TAGCACCACA GTGCGAGCAG CAAACCATAC

4751  GCTTCATTCA GCTCCGGTTC CCAACGATCA AGGCGAGTTA CATGATCCCC
      CGAAGTAAGT CGAGGCCAAG GGTTGCTAGT TCCGCTCAAT GTACTAGGGG
```

FIG. 3H

```
                                                          PvuI
                                                        -------
4801   CATGTTGTGC AAAAAAGCGG TTAGCTCCTT CGGTCCTCCG ATCGTTGTCA
       GTACAACACG TTTTTTCGCC AATCGAGGAA GCCAGGAGGC TAGCAACAGT

4851   GAAGTAAGTT GGCCGCAGTG TTATCACTCA TGGTTATGGC AGCACTGCAT
       CTTCATTCAA CCGGCGTCAC AATAGTGAGT ACCAATACCG TCGTGACGTA

4901   AATTCTCTTA CTGTCATGCC ATCCGTAAGA TGCTTTTCTG TGACTGGTGA
       TTAAGAGAAT GACAGTACGG TAGGCATTCT ACGAAAAGAC ACTGACCACT

BcgI
                                                     ---------------
4951   GTACTCAACC AAGTCATTCT GAGAATAGTG TATGCGGCGA CCGAGTTGCT
       CATGAGTTGG TTCAGTAAGA CTCTTATCAC ATACGCCGCT GGCTCAACGA

5001   CTTGCCCGGC GTCAATACGG GATAATACCG CGCCACATAG CAGAACTTTA
       GAACGGGCCG CAGTTATGCC CTATTATGGC GCGGTGTATC GTCTTGAAAT

XmnI
               ----------
                Asp700
               ----------
5051   AAAGTGCTCA TCATTGGAAA ACGTTCTTCG GGGCGAAAAC TCTCAAGGAT
       TTTCACGAGT AGTAACCTTT TGCAAGAAGC CCCGCTTTTG AGAGTTCCTA

5101   CTTACCGCTG TTGAGATCCA GTTCGATGTA ACCCACTCGT GCACCCAACT
       GAATGGCGAC AACTCTAGGT CAAGCTACAT TGGGTGAGCA CGTGGGTTGA

5151   GATCTTCAGC ATCTTTTACT TTCACCAGCG TTTCTGGGTG AGCAAAAACA
       CTAGAAGTCG TAGAAAATGA AAGTGGTCGC AAAGACCCAC TCGTTTTTGT

5201   GGAAGGCAAA ATGCCGCAAA AAAGGGAATA AGGGCGACAC GGAAATGTTG
       CCTTCCGTTT TACGGCGTTT TTTCCCTTAT TCCCGCTGTG CCTTTACAAC

SepI
                                -------
5251   AATACTCATA CTCTTCCTTT TCAATATTA TTGAAGCATT TATCAGGGTT
       TTATGAGTAT GAGAAGGAAA AAGTTATAAT AACTTCGTAA ATAGTCCCAA

5301   ATTGTCTCAT GAGCGGATAC ATATTTGAAT GTATTTAGAA AAATAAACAA
       TAACAGAGTA CTCGCCTATG TATAAACTTA CATAAATCTT TTTATTTGTT

5351   ATAGGGGTTC CGCGCACATT TCCCCGAAAA GTGCCACCTG ACGTCTAAGA
       TATCCCCAAG GCGCGTGTAA AGGGGCTTTT CACGGTGGAC TGCAGATTCT

5401   AACCATTATT ATCATGACAT TAACCTATAA AAATAGGCGT ATCACGAGGC
       TTGGTAATAA TAGTACTGTA ATTGGATATT TTTATCCGCA TAGTGCTCCG

5451   CCTTTCGTC
       GGAAAGCAG
```

SEQ ID NO:6

```
  1 TCGCGCGTTT CGGTGATGAC GGTGAAAACC TCTGACACAT GCAGCTCCCG GAGACGGTCA CAGCTTGTCT GTAAGCGGAT
    AGCGCGCAAA GCCACTACTG CCACTTTTGG AGACTGTGTA CGTCGAGGGC CTCTGCCAGT GTCGAACAGA CATTCGCCTA

81 GCCGGGAGCA GACAAGCCCG TCAGGGCGCG TCAGCGGGTG TTGGCGGGTG TCGGGCGGTG CTTAACTATG CGGCATCAGA
    CGGCCCTCGT CTGTTCGGGC AGTCGCCCGC AGTCGCCCAC AACCGCCCAC AGCCCGACC GAATTGATAC GCCGTAGTCT

161 GCAGATTGTA CTGAGAGTGC ACCATATGAA GCTTTTTGCA AAAGCCTAGG CCTCCAAAAA AGCCTCCTCA CTACTTCTGG
    CGTCTAACAT GACTCTCACG TGGTATACTT CGAAAAACGT TTTCGGATCC GGAGGTTTTT TCGGAGGAGT GATGAAGACC

241 AATAGCTCAG AGGCCGAGGC GGCCTCGGCC TCTGCATAAA TAAAAAAAAT TAGTCAGCCA TGGGGCGGAG AATGGGCGGA
    TTATCGAGTC TCCGGCTCCG CCGGAGCCGG AGACGTATTT ATTTTTTTTA ATCAGTCGGT ACCCCGCCTC TTACCCGCCT

321 ACTGGGCGGG GAGGGAATTA TTGGCTATTG GCCATTGCAT ACGTTGTATC TATATCATAA TATGTACATT TATATATTGGCT
    TGACCCGCCC CTCCCTTAAT AACCGATAAC CGGTAACGTA TGCAACATAG ATATAGTATT ATACATGTAA ATATAACCGA

401 CATGTCCAAT ATGACCGCCA TGTTGACATT GATTATTGAC TAGTTATTAA TAGTAATCAA TTACGGGGTC ATTAGTTCAT
    GTACAGGTTA TACTGGCGGT ACAACTGTAA CTAATAACTG ATCAATAATT ATCATTAGTT AATGCCCCAG TAATCAAGTA

481 AGCCCATATA TGGAGTTCCG CGTTACATAA CTTACGGTAA ATGGCCCGCC TGGCTGACCG CCCAACGACC CCCGCCCATT
    TCGGGTATAT ACCTCAAGGC GCAATGTATT GAATGCCATT TACCGGGCGG ACCGACTGGC GGTTGCTGG GGGCGGGTAA

561 GACGTCAATA ATGACGTATG TTCCCATAGT AACGCCAATA GGGACTTTCC ATTGACGTCA ATGGGTGGAG TATTTACGGT
    CTGCAGTTAT TACTGCATAC AAGGGTATCA TTGCGGTTAT CCCTGAAAGG TAACTGCAGT TACCCACCTC ATAAATGCCA

641 AAACTGCCCA CTTGGCAGTA CATCAAGTGT ATCATATGCC AAGTCCGCCC CCTATTGACG TCAATGACGG TAAATGGCCC
    TTTGACGGGT GAACCGTCAT GTAGTTCACA TAGTATACGG TTCAGGCGGG GGATAACTGC AGTTACTGCC ATTTACCGGG

721 GCCTGGCATT ATGCCCAGTA CATGACCTTA CGGGACTTTC CTACTTGGCA GTACATCTAC GTATTAGTCA TCGCTATTAC
    CGGACCGTAA TACGGGTCAT GTACTGGAAT GCCCTGAAAG GATGAACCGT CATGTAGATG CATAATCAGT AGCGATAATG

801 CATGGTGATG CGGTTTTGGC AGTACACCAA TGGGCGTGGA TAGCGGTTTG ACTCACGGGG ATTTCCAAGT CTCCACCCCA
    GTACCACTAC GCCAAAACCG TCATGTGGTT ACCCGCACCT ATCGCCAAAC TGAGTGCCCC TAAAGGTTCA GAGGTGGGGT

881 TTGACGTCAA TGGGAGTTTG TTTTGGCACC AAAATCAACG GGACTTTCCA AAATGTCGTA ATAACCCCGC CCCGTTGACG
    AACTGCAGTT ACCCTCAAAC AAAACCGTGG TTTTAGTTGC CCTGAAAGGT TTTACAGCAT TATTGGGGCG GGGCAACTGC

961 CAAATGGGCG GTAGGCGTGT ACGGTGGGAG GTCTATATAA GCAGAGCTCG TTTAGTGAAC CGTCAGATCG CCTGGAGACG
    GTTTACCCGC CATCCGCACA TGCCACCCTC CAGATATATT CGTCTCGAGC AATCACTTG GCAGTCTAGC GGACCTCTGC
```

FIG. 4B

```
1041  CCATCCACGC TGTTTTGACC TCCATAGAAG ACACCGGGAC CGATCCAGCC TCCGCGGCCG GGAACGGTGC ATTGGAACGC
      GGTAGGTGCG ACAAAACTGG AGGTATCTTC TGTGGCCCTG GCTAGGTCGG AGGCGCCGGC CCTTGCCACG TAACCTTGCG

1121  GGATTCCCCG TGCCAAGAGT GACGTAAGTA CCGCCTATAG ACTCTATAGG CACACCCCTT TGGCTCTTAT GCATGCTATA
      CCTAAGGGGC ACGTTCTCA CTGCATTCAT GGCGGATATC TGAGATATCC GTGTGGGGAA ACCGAGAATA CGTACGATAT

1201  CTGTTTTTGG CTTGGGGCCT ATACACCCCC GCTCCTTATG CTATAGGTGA TGGTATAGCT TAGCCTATAG GTGTGGGTTA
      GACAAAAACC GAACCCCGGA TATGTGGGGG CGAGGAATAC GATATCCACT ACCATATCGA ATCGGATATC CACACCCAAT

1281  TTGACCATTA TTGACCACTC CCCTATTGGT GACGATACTT TCCATTACTA ATCCATATAACA TGGCTCTTTG CCACAACTAT
      AACTGGTAAT AACTGGTGAG GGGATAACCA CTGCTATGAA AGGTAATGAT TAGGTATTGT ACCGAGAAAC GGTGTTGATA

1361  CTCTATTGGC TATATGCCAA TACTCTGTCC TTCAGAGACT GACACGGACT CTGTATTTTT ACAGGATGGG GTCCATTTAT
      GAGATAACCG ATATACGGTT ATGAGACAGG AAGTCTCTGA CTGTGCCTGA GACATAAAAA TGTCCTACCC CAGGTAAATA

1441  TATTTACAAA TTCACATATA CAACAACGCC GTCCCCCGTG CCCGCAGTTT TTATTAAACA TAGCGTGGGA TCTCCGACAT
      ATAAATGTTT AAGTGTATAT GTTGTTGCGG CAGGGGGCAC GGGCGTCAAA AATAATTTGT ATCGCACCCT AGAGGCTGTA

1521  CTCGGGTACG ATGGGCTCTT CTCCGGTAGC GGCGGAGCTT CCACATCCGA GCCCTGGTCC CATCCGTCCA
      GAGCCCATGC ACAAGGCCTG TACCCGAGAA GAGGCCATCG CCGCCTCGAA GGTGTAGGCT CGGGACCAGG GTAGGCAGT

1601  GCGGCTCATG GTCGCTCGGC AGCTCCTTGC TCCTAACAGT GGAGGCCAGA CTTAGGCACA GCACAATGCC CACCACCACC
      CGCCGAGTAC CAGCGAGCCG TCGAGGAACG AGGATTGTCA CCTCCGGTCT GAATCCGGT CGTGTTACGG GTGGTGGTGG

1681  AGTGTGCCGC ACAAGGCCCT GGCGGTAGGG TATGTGTCTG AAAATGAGCT CGGAGATTGG GCTCGCACCT GGACGCAGAT
      TCACACGGCG TGTTCCGGCA CCGCCATCCC ATACACAGAC TTTTACTCGA GCCTCTAACC CGAGCGTGGA CCTGCGTCTA

1761  GGAAGACTTA AGGCAGCGGC AGAAGAAGAT GCAGGCAGCT GAGTTGTTGT ATTCTGATAA GAGTCAGAGG TAACTCCCGT
      CCTTCTGAAT TCCGTCGCCG TCTTCTTCTA CGTCCGTCGA CTCAACAACA TAAGACTATT CTCAGTCTCC ATTGAGGGCA

1841  TGCGGTGCTG TTAACGGTGG AGGGCAGTGT AGTCTGAGCA GTACTCGTTG CTGCCGGCGC CGCCACCAGA CATAATAGCT
      ACGCCACGAC AATTGCCACC TCCCGTCACA TCAGACTCGT CATGAGCAAC GACGGCCGCG GCGGTGGTCT GTATTATCGA
```

FIG. 4C

```
                                             SEQ ID NO:7      M  D  A
                     PstI                            EcoRI
                   ---------                        ---------
+3
1921  GACAGACTAA CAGACTGTTC CTTTCCATGG GTCTTTTCTG CAGTCACCGT CGTCGACGAA TTCAAGCAAT CATGGATGCA
      CTGTCTGATT GTCTGACAAG GAAAGGTACC CAGAAAAGAC GTCAGTGGCA GCAGCTGCTT AAGTTCGTTA GTACCTACGT

+3    M  K  R  G   L  C  C   V  L  L    L  C  G  A   V  F  V   S  P  S   A  S  E  T   H  V  T
2001  ATGAAGAGAG GGCTCTGCTG TGTGCTGCTG CTGTGTGGAG CAGTCTTCGT TTCGCCCAGC GCTAGCGAAA CCCACGTCAC
      TACTTCTCTC CCGAGACGAC ACACGACGAC GACACACCTC GTCAGAAGCA AAGCGGGTCG CGATCGCTTT GGGTGCAGTG

+3    G  G  S   A  G  H  T   V  S  G   F  V  S   L  L  A  P   G  A  K   Q  N  V   Q  L  I
2081  CGGGGAAGT GCCGGCCACA CTGTGTCTGG ATTTGTTAGC CTCCTCGCAC CAGGCGCCAA GCAGAACGTC CAGCTGATCA
      GCCCCTTCA CGGCCGGTGT GACACAGACC TAAACAATCG GAGGAGCGTG GTCCGCGGTT CGTCTTGCAG GTCGACTAGT

+3    N  T  N  G   S  W  H   L  N  S   T  A  L  N   C  N  D   S  L  N  T   G  W  L   A  G  L
2161  ACACCAACGG CAGTTGGCAC CTCAATAGCA CGGCCCTGAA CTGCAATGAT AGCCTCAACA CCGGCTGGTT GGCAGGGCTT
      TGTGGTTGCC GTCAACCGTG GAGTTATCGT GCCGGGACTT GACGTTACTA TCGGAGTTGT GGCCGACCAA CCGTCCCGAA

+3    F  Y  H  H   K  F  N   S  S  G   C  P  E  R   L  A  S   C  R  P    L  T  D  P   D  Q  G
2241  TTCTATCACC ACAAGTTCAA CTCTTCAGGC TGTCCTGAGA GGCTAGCCAG CTGCCGACCC CTTACCGATT TGACCAGGG
      AAGATAGTGG TGTTCAAGTT GAGAAGTCCG ACAGGACTCT CCGATCGGTC GACGGCTGGG GAATGGCTAA AACTGGTCCC

+3    W  G  P   I  S  Y  A   N  G  S   G  P  D   Q  R  P  Y   C  W  H   Y  P  P   K  P  C
2321  CTGGGGCCCT ATCAGTTATG CCAACGGAAG CGGCCCCGAC CAGCGCCCCT ACTGCTGGCA CTACCCCCCA AAACCTTGCG
      GACCCCGGGA TAGTCAATAC GGTTGCCTTC GCCGGGGCTG GTCGCGGGGA TGACGACCGT GATGGGGGGT TTTGGAACGC

+3    G  I  V  P   A  K  S   V  C  G  P   V  Y  C   F  T  P   S  P  V  V   G  T   T  D  R
2401  GTATTGTGCC CGCGAAGAGT GTGTGTGGTC CGGTATATTG CTTCACTCCC AGCCCCGTGG TGGTGGGAAC GACCGACAGG
      CATAACACGG GCGCTTCTCA CACACACCAG GCCATATAAC GAAGTGAGGG TCGGGGCACC ACCACCCTTG CTGGCTGTCC

+3    S  G  A  P   T  Y  S   W  G  E   N  D  T  D   V  F  V   L  N  N   T  R  P  P   L  G  N
2481  TCGGGCGCGC CCACTACAGC TGGGGTGAA AATGATACGG AGTCTTCGT CCTTAACAAT ACCAGGCCAC CGCTGGGCAA
      AGCCCGCGCG GGTGGATGTC GACCCCACTT TTACTATGCC TGCAGAAGCA GGAATTGTTA TGGTCCGGTG GCGACCCGTT

+3    W  F  G   C  T  W  M   N  S  T   G  F  T   K  V  C  G   A  P  P   C  V  I   G  G  A
2561  TTGGTTCGGT TGTACCTGGA TGAACTCAAC TGGATTCACC AAAGTGTGCG GAGGCCTCC TGTGTCATC GGAGGGGCGG
      AACCAAGCCA ACATGGACCT ACTTGAGTTG ACCTAAGTGG TTTCACACGC CTCGGAGG AACACAGTAG CCTCCCCGCC
```

FIG. 4D

```
     +3  G  N  N  T    L  H  C    P  T  D  C    F  R  K    H  P  D    A  T  Y  S    R  C  G    S  G  P
   2641  GCAACAACAC CCTGCACTGC CCCACTGATT GCTTCCGCAA GCATCCGGAC GCCACATACT CTCGGTGCGG CTCCGGTCCC
         CGTTGTTGTG GGACGTGACG GGGTGACTAA CGAAGGCGTT CGTAGGCCTG CGGTGTATGA GAGCCACGCC GAGGCCAGGG

+3  W  I  T  P    R  C  L    V  D  Y    P  Y  R  L    W  H  Y    P  C  T    I  N  Y  T    I  F  K
   2721  TGGATCACAC CCAGGTGCCT GGTCGACTAC CCGTATAGGC TTTGGCATTA TCCTTGTACC ATCAACTACA CCATATTAA
         ACCTAGTGTG GGTCCACGGA CCAGCTGATG GGCATATCCG AAACCGTAAT AGGAACATGG TAGTTGATGT GGTATAAATT

+3  I  R  M    Y  V  V  G    V  E  H    R  L  E    A  A  C  N    W  T  R    G  E  R    C  D  L
   2801  AATCAGGATG TACGTGGGAG GGTCGAACA CAGGCTGGAA GCTGCCTGCA ACTGGACGCG GGGCGAACGT TGCGATCTGG
         TTAGTCCTAC ATGCACCCTC CCCAGCTTGT GTCCGACCTT CGACGGACGT TGACCTGCGC CCCGCTTGCA ACGCTAGACC

+3  E  D  R  D    R  S  E    I  D  M  E    N  I  T    S  G  F    L  G  P  L    L  V  L    Q  A  G
   2881  AAGATAGGGA CAGGTCCGAG ATCGATATGG AGAACATCAC ATCAGGATTC CTAGGACCCC TGCTCGTGTT ACAGGCGGGG
         TTCTATCCCT GTCCAGGCTC TAGCTATACC TCTTGTAGTG TAGTCCTAAG GATCCTGGGG ACGAGCACAA TGTCCGCCCC
                                        ClaI
                                        ------

+3  F  F  L  L    T  R  I    L  T  I    P  Q  S  L    D  S  W    T  S    L  N  F  L    G  G  S
   2961  TTTTTCTTGT TGACAAGAAT CCTCACAATA CCGCAGAGTC TAGACTCGTG GTGGACTTCT CTCAATTTTC TAGGGGGATC
         AAAAAGAACA ACTGTTCTTA GGAGTGTTAT GGCGTCTCAG ATCGAGCAC CACCTGAAGA GAGTTAAAAG ATCCCCCTAG

+3  P  V  C    L  G  Q  N    S  Q  S    P  T  S    N  H  S  P    T  S  C    P  P  I    C  P  G
   3041  TCCCGTGTGT CTTGGCCAAA ATTCGCAGTC CCCAACCTCC AATCACTCAC CAACCTCCTG TCCTCCAATT TGTCCTGGTT
         AGGGCACACA GAACCGGTTT TAAGCGTCAG GGGTTGGAGG TTAGTGAGTG GTTGGAGGAC AGGAGGTTAA ACAGGACCAA

+3  Y  R  W  M    C  L  R    R  F  I  I    F  L  F    I  L  L    L  C  L  I    F  L  L    V  L  L
   3121  ATCGCTGGAT GTGTCTGCGG CGTTTTATCA TATTCCTCTT CATCCTGCTG CTATGCCTCA TCTTCTTATT GGTTCTTCTG
         TAGCGACCTA CACAGACGCC GCAAAATAGT ATAAGGAGAA GTAGGACGAC GATACGGAGT AGAAGAATAA CCAAGAAGAC

+3  D  Y  Q  G    M  L  P    V  C  P    L  I  P  G    S  T  T    T  S  T    G  P  C  K    T  C  T
   3201  GATTATCAAG GTATGTTGCC CGTTTGTCCT CTAATTCCAG GATCAACAAC AACCAGTACG GGACCATGCA AAACCTGCAC
         CTAATAGTTC CATACAACGG GCAAACAGGA GATTAAGGTC CTAGTTGTTG TTGGTCATGC CCTGGTACGT TTTGGACGTG

+3  T  P  A    Q  G  N  S    M  F  P    S  C  C    C  T  K  P    T  D  G    N  C  T    C  I  P
   3281  GACTCCTGCT CAAGGCAACT CTATGTTTCC CTCATGTTGC TGTACAAAAC CTACGGATGG AAATTGCACC TGTATTCCCA
         CTGAGGACGA GTTCCGTTGA GATACAAAGG GAGTACAACG GAGTGCAACG GATGCCTACC TTTAACGTGG ACATAAGGGT
```

FIG. 4E

```
      I  P  S  S    W  A  F    A  K  Y  L    W  E  W    A  S  V    R  F  S  W    L  S  L    L  V  P
  +3  TCCCATCGTC CTGGGCTTTC GCAAATACC TATGGGAGTG GGCCTCAGTC CGTTTCTCTT GGCTCAGTTT ACTAGTGCCA
3361  AGGGTAGCAG GACCCGAAAG CGTTTATGG ATACCCTCAC CCGGAGTCAG GCAAAGAGAA CCGAGTCAAA TGATCACGGT

F  V  Q  W    G  F  V  G    L  S  P    T  V  W  L    S  A  I    M  M    W  Y  W  G    P  S  L
  +3  TTTGTTCAGT GGTTCGTAGG GCTTTCCCCC ACTGTTTGGC TTTCAGCTAT ATGGATGATG TGGTATTGGG GGCCAAGTCT
3441  AAACAAGTCA CCAAGCATCC CGAAAGGGGG TGACAAACCG AAGTCGATA TACCTACTAC ACCATAACCC CCGGTTCAGA

Y  S  I    V  S  P    F  I  P  L    L  P  I    F  F  C  L    W  V  Y    I  *                         EcoRI
  +3  GTACAGCATC GTGAGTCCCT TTATACCGCT GTTACCAATT AAGGATCCAC TTCTTTTGTC CTTGGGTATA CATTTAAGAA TTCAGACTCG
3521  CATGTCGTAG CACTCAGGGA AATATGGCGA CAATGGTTAA TTCCTAGGTG AAGAAAACAG GAACCCATAT GTAAATTCTT AAGTCTGAGC
                                                             BamHI

3601  AGCAAGTCTA GAAAGGCGCG CCAAGATATC AAGGATCCAC TACGCGTTAG AGCTCGCTGA TCAGCCTCGA CTGTGCCTTC
      TCGTTCAGAT CTTTCCGCGC GGTTCTATAG TTCCTAGGTG ATGCGCAATC TCGAGCGACT AGTCGGAGCT GACACGGAAG

3681  TAGTTGCCAG CCATCTGTTG TTTGCCCCTC CCCCGTGCCT TCCTTGACCC TGGAAGGTGC CACTCCCACT GTCCTTTCCT
      ATCAACGGTC GGTAGACAAC AAACGGGGAG GGGGCACGGA AGGAACTGGG ACCTTCCACG GTGAGGGTGA CAGGAAAGGA

3761  AATAAAATGA GGAAATTGCA TCGCATTGTC TGAGTAGGTG TCATTCTATT AGTAAGATAA TCTTCCGCTT CTGGGGGTG CTGGGGGCA GGACAGCAAG
      TTATTTTACT CCTTTAACGT AGCGTAACAG ACTCATCCAC AGTAAGATAA TCATTCTATT AGAAGGCGAA GACCCCCAC CCTGTCGTTC

3841  GGGGAGGATT GGGAAGACAA TAGCAGGCAT GCTGGGGAGC TCTTCCGCTT AATACGGTTA TCCACAGAAT CAGGGGATAA CGCAGGAAAG
      CCCCTCCTAA CCCTTCTGTT ATCGTCCGTA CGACCCCTCG AGAAGGCGAA TTATGCCAAT AGGTGTCTTA GTCCCCTATT GCGTCCTTTC

3921  TTCGGCTGCG GCGAGCGGTA TCAGCTCACT CAAAGGCGGT CAAAGGCGCC AGGAACCGTA AAAAGGCCGC GTTGCTGGCG TTTTTTCCATA GGCTCCGCCC
      AAGCCGACGC CGCTCGCCAT AGTCGAGTGA GTTTCCGCCA GTTTCCGCGG TCCTTGGCAT TTTTCCGGCG CAACGACCGC AAAAGGTAT CCGAGGCGGG

4001  AACATGTGAG CAAAAGGCCA GCAAAAGGCC AGGAACCGTA AAAAGGCCGC GTTGCTGGCG TTTTTTCCATA GGCTCCGCCC
      TTGTACACTC GTTTTCCGGT CGTTTTCCGG TCCTTGGCAT TTTTCCGGCG CAACGACCGC AAAAGGTAT CCGAGGCGGG

4081  CCCTGACGAG CATCACAAAA ATCGACGCTC AAGTCAGAGG TGGCGAAACC CGACAGGACT ATAAAGATAC CAGGGCGTTTC
      GGGACTGCTC GTAGTGTTTT TAGCTGCGAG TTCAGTCTCC ACCGCTTTGG GCTGTCCTGA TATTTCTATG GTCCGCAAAG
```

FIG. 4F

```
4161  CCCCTGGAAG  CTCCCTCGTG  CGCTCTCCTG  TTCCGACCCT  GCCGCTTACC  GGATACCTGT  CCGCCTTTCT  CCCTTCGGA
      GGGGACCTTC  GAGGGAGCAC  GCGAGAGGAC  AAGGCTGGGA  CGGCGAATGG  CCTATGGACA  GGCGAAAGA   GGGAAGCCCT

4241  AGCGTGGCGC  TTTCTCAATG  CTCACGCTGT  AGTATCTCA   GTTCGGTGTA  GTTCGTTCGC  TCCAAGCTGG  GCTGTGTGCA
      TCGCACCGCG  AAAGAGTTAC  GAGTGCGACA  TCCATAGAGT  CAAGCCACAT  CCAGCAAGCG  AGGTTCGACC  CGACACACGT

4321  CGAACCCCCC  GTTCAGCCCG  ACCGCTGCGC  CTTATCCGGT  AACTATCGTC  TTGAGTCCAA  CCCGGTAAGA  CACGACTTAT
      GCTTGGGGGG  CAAGTCGGGC  TGGCGACGCG  GAATAGGCCA  TTGATAGCAG  AACTCAGGTT  GGGCCATTCT  GTGCTGAATA

4401  CGCCACTGGC  AGCAGCCACT  GGTAACAGGA  TTAGCAGAGC  GAGGTATGTA  GGCGGTGCTA  CAGAGTTCTT  GAAGTGGTGG
      GCGGTGACCG  TCGTCGGTGA  CCATTGTCCT  AATCGTCTCG  CTCCATACAT  CCGCCACGAT  GTCTCAAGAA  CTTCACCACC

4481  CCTAACTACG  GCTACACTAG  AAGGACAGTA  TTTGGTATCT  GCGCTCTGCT  GAAGCCAGTT  ACCTTCGGAA  AAAGAGTTGG
      GGATTGATGC  CGATGTGATC  TTCCTGTCAT  AAACCATAGA  CGCGAGACGA  CTTCGGTCAA  TGGAAGCCTT  TTTCTCAACC

4561  TAGCTCTTGA  TCCGGCAAAC  AAACCACCGC  TGGTAGCGGT  TTTGCAAGCA  GCAGATTACG  CGCAGAAAAA  CGCAGAAAAA
      ATCGAGAACT  AGGCCGTTTG  TTTGGTGGCG  ACCATCGCCA  AAACGTTCGT  CGTCTAATGC  GCGTCTTTTT  GCGTCTTTTT

4641  AAGGATCTCA  AGAAGATCCT  TTGATCTTTT  CTACGGGGTC  TGACGCTCAG  TGGAACGAAA  ACTCACGTTA  AGGGATTTTG
      TTCCTAGAGT  TCTTCTAGGA  AACTAGAAAA  GATGCCCCAG  ACTGCGAGTC  ACCTTGCTTT  TGAGTGCAAT  TCCCTAAAAC

4721  GTCATGAGAT  TATCAAAAAG  GATCTTCACC  TAGATCCTTT  TAAATTAAAA  ATGAAGTTTT  AAATCAATCT  AAAGTATATA
      CAGTACTCTA  ATAGTTTTTC  CTAGAAGTGG  ATCTAGGAAA  ATTTAATTTT  TACTTCAAAA  TTTAGTTAGA  TTTCATATAT

4801  TGAGTAAACT  TGGTCTGACA  GTTACCAATG  CTTAATCAGT  GAGGCACCTA  TCTCAGCGAT  CTGTCTATTT  CGTTCATCCA
      ACTCATTTGA  ACCAGACTGT  CAATGGTTAC  GAATTAGTCA  CTCCGTGGAT  AGAGTCGCTA  GACAGATAAA  GCAAGTAGGT

4881  TAGTTGCCTG  ACTCCCCGTC  GTGTAGATAA  CTACGATACG  GGAGGGCTTA  CCATCTGGCC  CCAGTGCTGC  AATGATACCG
      ATCAACGGAC  TGAGGGGCAG  CACATCTATT  GATGCTATGC  CCTCCCGAAT  GGTAGACCGG  GGTCACGACG  TTACTATGGC

4961  CGAGACCCAC  GCTCACCGGC  TCCAGATTTA  TCAGCAATAA  ACCAGCCAGC  CGGAAGGGCC  GAGCGCAGAA  GTGGTCTGC
      GCTCTGGGTG  CGAGTGGCCG  AGGTCTAAAT  AGTCGTTATT  TGGTCGGTCG  GCCTTCCCGG  CTCGCGTCTT  CACCAGACG

5041  AACTTTATCC  GCCTCCATCC  AGTCTATTAA  TTGTTGCCGG  GAAGCTAGAG  TAAGTAGTTC  GCCAGTTAAT  AGTTTGCGCA
      TTGAAATAGG  CGGAGGTAGG  TCAGATAATT  AACAACGGCC  CTTCGATCTC  ATTCATCAAG  CGGTCAATTA  TCAAACGCGT

5121  ACGTTGTTGC  CATTGCTACA  GGCATCGTGG  TGTCACGCTC  GTCGTTTGGT  ATGGCTTCAT  TCAGCTCCGG  TTCCCAACGA
      TGCAACAACG  GTAACGATGT  CCGTAGCACC  ACAGTGCGAG  CAGCAAACCA  TACCGAAGTA  AGTCGAGGCC  AAGGGTTGCT
```

FIG. 4G

```
5201  TCAAGGCGAG TTACATGATC CCCATGTTTG TGCAAAAAAG CGGTTAGCTC CTTCGGTCCT CCGATCGTTG TCAGAAGTAA
      AGTTCCGCTC AATGTACTAG GGGTACAAAC ACGTTTTTTC GCCAATCGAG GAAGCCAGGA GGCTAGCAAC AGTCTTCATT

5281  GTTGGCCGCA GTGTTATCAC TCATGGTTAT GGCAGCACTG CATAATTCTC TTACTGTCAT GCCATCCGTA AGATGCTTTT
      CAACCGGCGT CACAATAGTG AGTACCAATA CCGTCGTGAC GTATTAAGAG AATGACAGTA CGGTAGGCAT TCTACGAAAA

5361  CTGTGACTGG TGAGTACTCA ACCAAGTCAT TCTGAGAATA GTGTATGCGG CGACCGAGTT GCTCTTGCCC GGCGTCAATA
      GACACTGACC ACTCATGAGT TGGTTCAGTA AGACTCTTAT CACATACGCC GCTGGCTCAA CGAGAACGGG CCGCAGTTAT

5441  CGGGATAATA CCGCGCCACA TAGCAGAACT TTAAAAGTGC TCATCATTGG AAAACGTTCT TCGGGGCGAA AACTCTCAAG
      GCCCTATTAT GGCGCGGTGT ATCGTCTTGA AATTTTCACG AGTAGTAACC TTTTGCAAGA AGCCCCGCTT TTGAGAGTTC

5521  GATCTTACCG CTGTTGAGAT CCAGTTCGAT GTAACCCACT CGTGCACCCA ACTGATCTTC AGCATCTTTT ACTTTCACCA
      CTAGAATGGC GACAACTCTA GGTCAAGCTA CATTGGGTGA GCACGTGGGT TGACTAGAAG TCGTAGAAAA TGAAAGTGGT

5601  GCGTTTCTGG GTGAGCAAAA ACAGGAAGGC AAAAAAGGGA ATAAGGGCGA CACGGAAATG TTGAATACTC
      CGCAAAGACC CACTCGTTTT TGTCCTTCCG TTTTTTCCCT TATTCCCGCT GTGCCTTTAC AACTTATGAG

5681  ATACTCTTCC TTTTTCAATA TTATTGAAGC ATTTATCAGG GTTATTGTCT CATGAGCGGA TACATATTTG AATGTATTTA
      TATGAGAAGG AAAAAGTTAT AATAACTTCG TAAATAGTCC CAATAACAGA GTACTCGCCT ATGTATAAAC TTACATAAAT

5761  GAAAAATAAA CAAATAGGGG TTCCGCGCAC ATTTCCCCGA AAAGTGCCAC CTGACGTCTA AGAAACCATT ATTATCATGA
      CTTTTTATTT GTTTATCCCC AAGGCGCGTG TAAAGGGGCT TTTCACGGTG GACTGCAGAT TCTTTGGTAA TAATAGTACT

5841  CATTAACCTA TAAAAATAGG CGTATCACGA GGCCCTTTCG TC
      GTAATTGGAT ATTTTTATCC GCATAGTGCT CCGGGAAAGC AG
```

FIG. 4H

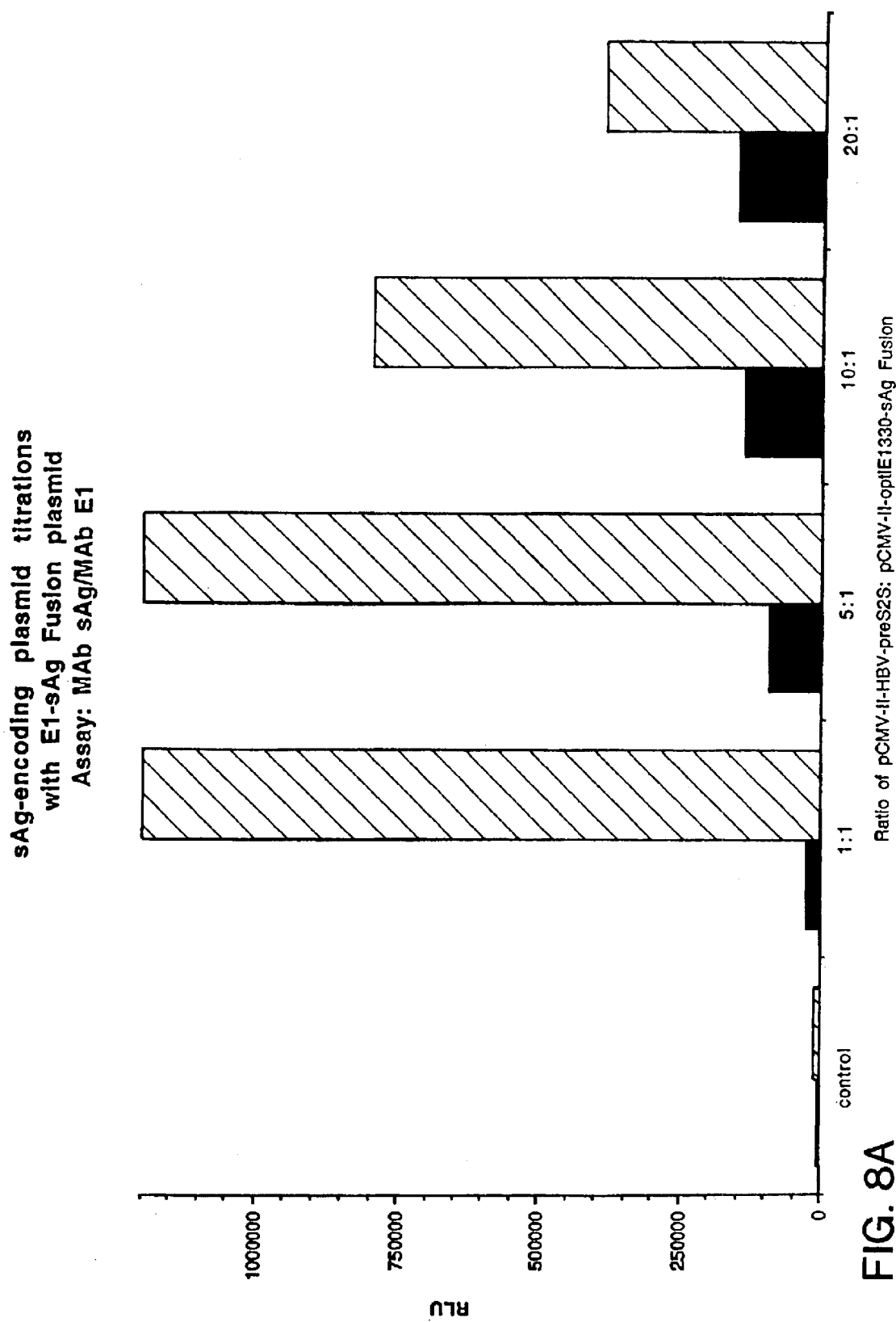

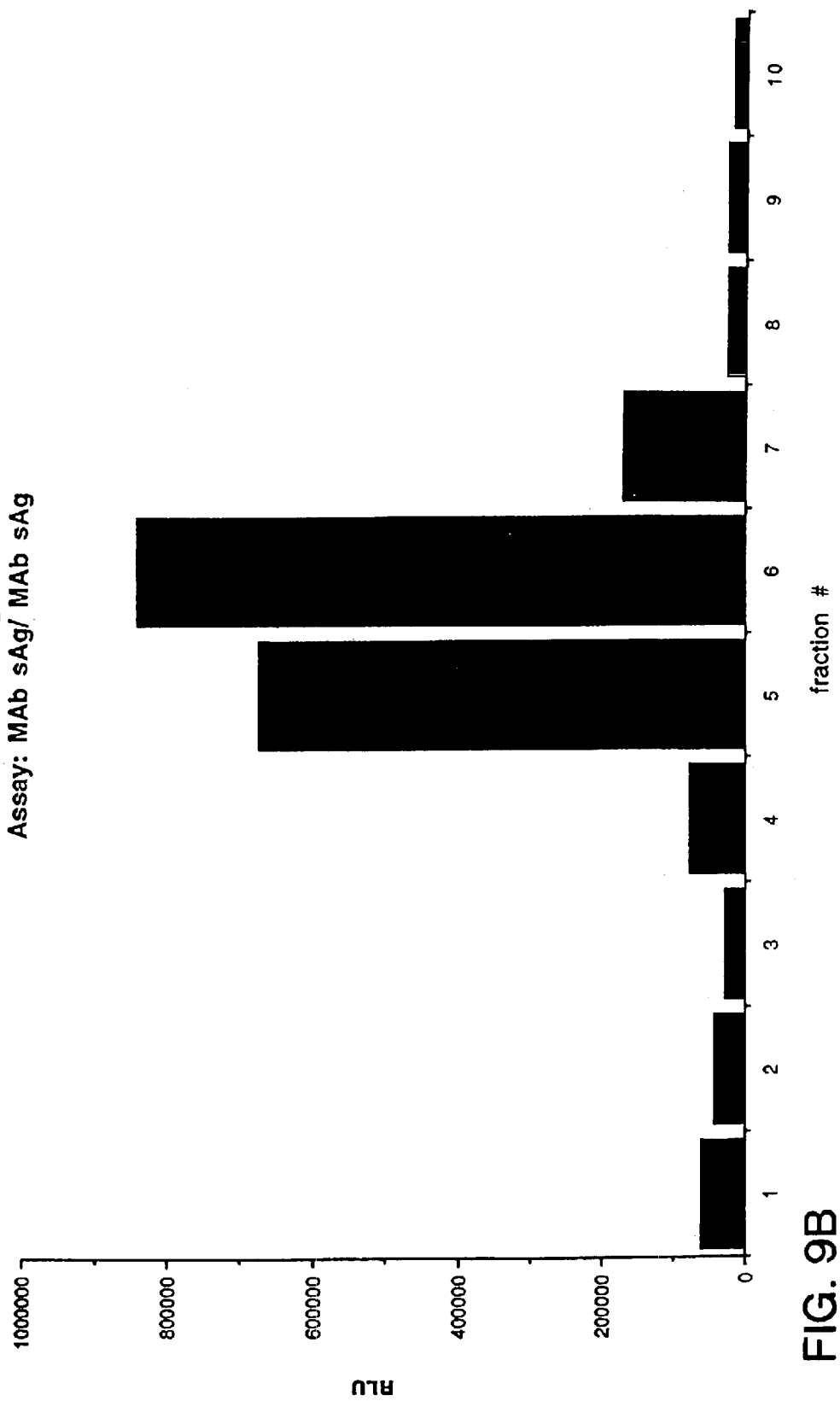

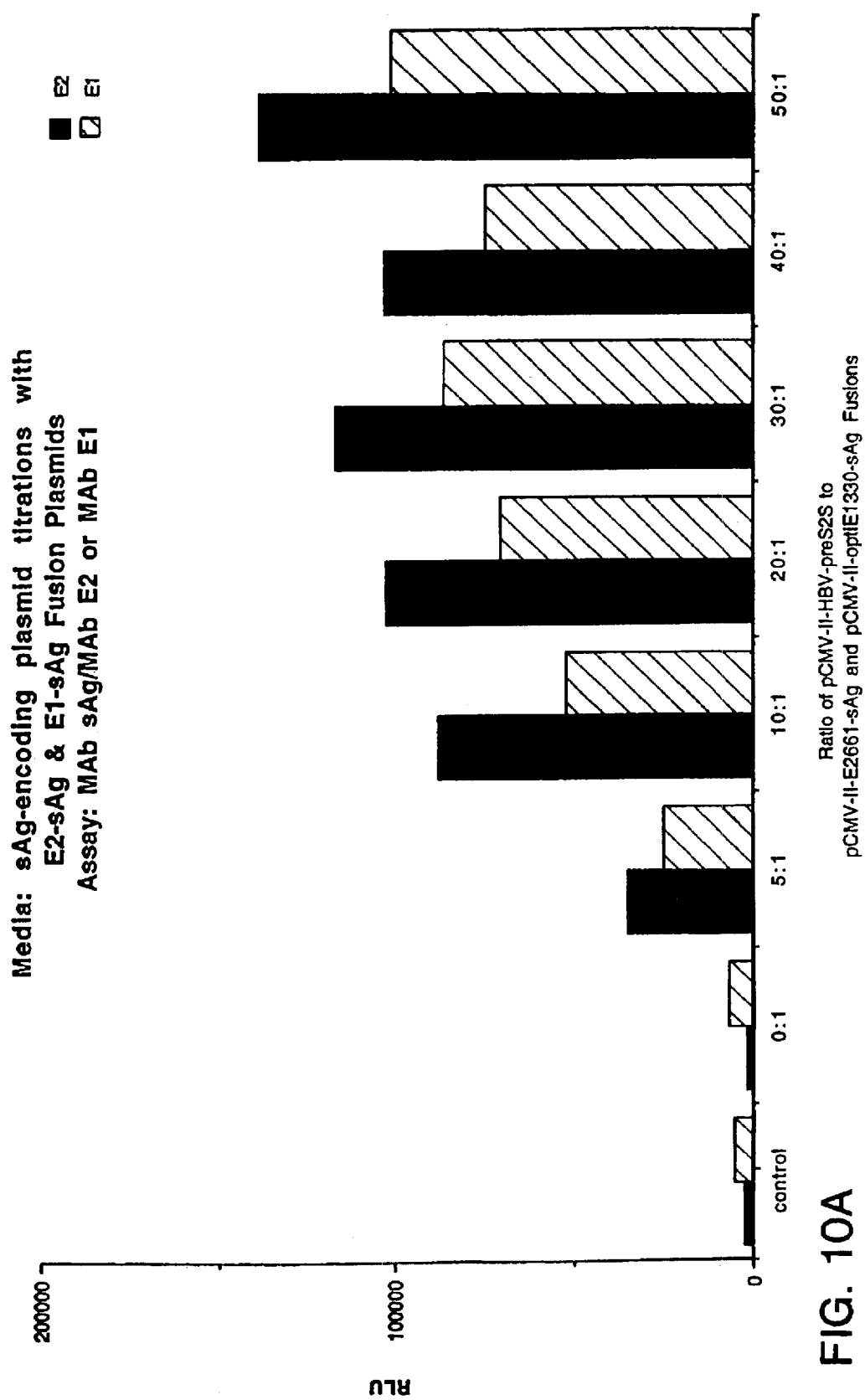

HBV/HCV VIRUS-LIKE PARTICLE

CROSS-REFERENCE TO RELATED APPLICATION

This application is related to provisional patent application serial No. 60/167,224, filed Nov. 24, 1999, from which priority is claimed under 35 USC §119(e)(1) and which is incorporated herein by reference in its entirety.

TECHNICAL FIELD OF THE INVENTION

The invention is related to the area of recombinant vaccines. It is particularly related to the field of chimeric antigens and virus-like particles for use in vaccines, especially combination vaccines for Hepatitis B virus (HBV) and Hepatitis C virus (HCV).

BACKGROUND OF THE INVENTION

Hepatitis C virus (HCV) infects approximately 1% of the world's population and causes serious health problems. Over 75% of acutely infected individuals eventually progress to a chronic carrier state that can result in cirrhosis, liver failure, and hepatocellular carcinoma. A very small fraction of chronically infected patients clear HCV naturally and resolve chronic hepatitis. See Alter et al. (1992) N. Engl. J. Med. 327:1899–1905; Resnick and Koff. (1993) Arch. Intern. Med. 153:1672–1677; Seeff (1995) Gastrointest. Dis. 6:20–27; Tong et al. (1995) N. Engl. J. Med. 332:1463–1466. Immunization against E2 glycoproteins of some flaviviruses (see e.g., Konishi et al., (1992) Virology 188: 714–720), including HCV (Ishii et al., (1998) Hepatology 28: 1117–1120), may protect against infection. However, attempts to express recombinant HCV E1 and E2 glyocoproteins have been frustrated by the fact that these proteins are not secreted from the host cell but are retained within the endoplasmic reticulum (Dubuisson et al. (1994) J. Virology 68: 6147–6160).

One approach to making vaccines for HCV and other viruses which has been attempted is to prepare chimeric antigens consisting of fusions of hepatitis B virus surface antigen (HBsAg) with a heterologous antigen, for example a portion of an HCV protein. See, e.g., Inchauspe et al. (1998) Dev. Biol. Stand. 92: 162–168; Nakano et al. (1997) J. Virol. (1997) 71: 7101–7109; and Inchauspe et al. (1997) Vaccine 15: 853–856. The use of HBsAg is attractive for the production of immunogenic compositions such as vaccines because HBsAg is highly immunogenic and is secreted from cultured cells in the form of virus-like particles (U.S. Pat. No. 5,098,704). Attempts to introduce small portions of viral proteins into HBsAg have succeeded in the production of virus-like particles (see e.g., Delpeyroux et al. (1990) J. Virology 64: 6090–6100, who inserted an 11 amino acid segment of polio virus capsid protein into HBsAg). However, in one study only two out of six fusion proteins containing HBsAg combined with different hydrophillic domains of HCV E2 were secreted into the culture medium as virus-like particles (Lee et al. (1996) J. Med. Virol. 50: 145–151), possibly because the E2 inserts were too large or hydrophilic. The insertion site of heterologous epitopes into HBsAg may be an important factor. A study which inserted an epitope of HBV nucleocapsid (HBcAg) at various positions into HBsAg found that insertion into an internal site in HBsAg resulted in a chimeric protein that was immunogenic for HBcAg, while insertion at the C-terminus was weakly immunogenic (Schodel et al. (1992) J. Virology 66: 106–114). Insertion at the N-terminus prevented surface access of the HBcAg epitope in the resultant particles and was non-immunogenic (Id.). Apparently, the molecular context in which an epitope is presented is important in determining immunogenicity, probably because of subtle alterations of protein secondary and tertiary structure. This principle was further illustrated by Eckhart et al. ((1996) J. Gen. Virol. 77: 2001–2008), who introduced a conserved, six amino acid epitope of HIV-1 gp41 protein into influenza hemagglutinin and obtained neutralizing antibodies, but could not generate neutralizing antibodies when the same epitope was inserted into HBsAg. Smaller isolated epitopes are more likely to be sensitive to such effects than larger portions of an immunogenic protein.

Currently there is no method available for expressing entire E1 or E2 glycoproteins of HCV in virus-like particles for use in immunization. Available methods limit chimeric proteins based on HBsAg to the insertion of only small isolated domains of E2, which may or may not have a native immunogenic structure. Thus, there remains a need in the art for methods and materials that can be used to express HCV antigens in an immunogenic form in virus-like particles.

SUMMARY OF THE INVENTION

It is an object of the invention to provide HBV/HCV chimeric antigens for use in immunogenic compositions. It is a further object of the invention to provide virus-like particles comprising HBV/HCV chimeric antigens and methods and materials for producing such virus-like particles. It is another object of the invention to provide HBV/HCV combination vaccines. These and other objects of the invention are provided by one or more of the embodiments described below.

One embodiment of the invention provides a virus-like particle for use as an immunogen or as a component of a vaccine. The virus-like particle comprises a first HBsAg (hepatitis B virus surface antigen) and a chimeric antigen. The chimeric antigen comprises a second HBsAg which is linked to an HCV immunogenic polypeptide. The first and the second HBsAg each comprise a substantially complete S domain.

Another embodiment of the invention provides another virus-like particle for use as an immunogen or as a component of a vaccine. The virus-like particle comprises a first HBsAg and first and second chimeric antigens. The first chimeric antigen comprises a second HBsAg which is linked to a first immunogenic polypeptide comprising an HCV E1 glycoprotein or a fragment thereof. The second chimeric antigen comprises a third HBsAg which is linked to a second immunogenic polypeptide comprising an HCV E2 glycoprotein or a fragment thereof. The first, second, and third HBsAg each comprise a substantially complete S domain.

Still another embodiment of the invention provides fusion proteins comprising a substantially complete S domain of HBsAg and a polypeptide. In one fusion protein, the polypeptide comprises (a) amino acid residues 192 to 330 of an HCV-1 polyprotein, or (b) the corresponding residues of other HCV isolates, or (c) an immunogenic sequence having at least about 80% sequence identity to (a) or (b). In another fusion protein, the polypeptide comprises (a) amino acid residues 384 to 661 of an HCV-1 polyprotein, or (b) the corresponding residues of other HCV isolates, or (c) an immunogenic sequence having at least about 80% sequence identity to (a) or (b).

Yet another embodiment of the invention provides nucleic acid molecules which encode fusion proteins comprising a substantially complete S domain of HBsAg and a polypeptide. In one fusion protein, the polypeptide comprises (a)

amino acid residues 192 to 330 of an HCV-1 polyprotein, or (b) the corresponding residues of other HCV isolates, or (c) an immunogenic sequence having at least about 80% sequence identity to (a) or (b). In another fusion protein, the polypeptide comprises (a) amino acid residues 384 to 661 of an HCV-1 polyprotein, or (b) the corresponding residues of other HCV isolates, or (c) an immunogenic sequence having at least about 80% sequence identity to (a) or (b). These nucleic acid molecules are employed as components of immunogenic compositions, which are additional embodiments.

Another embodiment of the invention provides vectors comprising nucleic acid molecules which encode fusion proteins. The fusion proteins comprise a substantially complete S domain of HBsAg and a polypeptide comprising an immunogenic fragment of an HCV-1 polyprotein.

A further embodiment of the invention provides a method of producing virus-like particles. A cell is cultured in a culture medium, whereby the cell expresses. virus-like particles comprising a first HBsAg and a chimeric antigen. The chimeric antigen comprises a second HBsAg which is linked to an HCV immunogenic polypeptide. The first and the second HBsAg each comprise a substantially complete S domain. The virus-like particles are then isolated from the culture medium.

Yet another embodiment is a method of producing a cell line that expresses virus-like particles. A cell is transfected with a vector that expresses virus-like particles comprising a first HBsAg and a chimeric antigen. The chimeric antigen comprises a second HBsAg which is linked to an HCV immunogenic polypeptide. The first and the second HBsAg each comprise a substantially complete S domain. The cell is cultured to produce a cell line that expresses the virus-like particles.

Still other embodiments of the invention are cell lines that express virus-like particles. In one cell line, the virus-like particles comprise a first HBsAg and a chimeric antigen. The chimeric antigen comprises a second HBsAg which is linked to an HCV immunogenic polypeptide. The first and the second HBsAg each comprise a substantially complete S domain. In another type of cell line, the virus-like particles comprise a first HBsAg and first and second chimeric antigens. The first chimeric antigen comprises a second HBsAg which is linked to a first immunogenic polypeptide comprising an HCV E1 glycoprotein or a fragment thereof, and the second chimeric antigen comprises a third HBsAg which is linked to a second immunogenic polypeptide comprising an HCV E2 glycoprotein or a fragment thereof. The first, second, and third HBsAg each comprise a substantially complete S domain.

The invention thus provides the art with novel methods and materials for the production of HBV/HCV combination vaccines.

BRIEF DESCRIPTION OF THE DRAWINGS

FIGS. 1A and 1B–1F show the expression vector pCMVII (FIG. 1A) and its nucleotide sequence (FIGS. 1B–1F; SEQ ID NO:1).

FIGS. 2A and 2B–2I show the expression vector pCMVII-pS2-sAg (FIG. 2A) and its nucleotide sequence (FIGS. 2B–2I and SEQ ID NO:2; preS2 coding sequence begins at nucleotide position 1988 and ends at nucleotide base 2152, and SAg coding sequence begins at base 2153 and ends at 2830). The amino acid sequence of the encoded preS2-S polypeptide is also displayed in FIGS. 2B–2I and in SEQ ID NO:3.

FIGS. 3A and 3B–3I show the expression vector pCMVII opti 330 E1/SAg (FIG. 3A) and its nucleotide sequence (FIGS. 3B–3I and SEQ ID NO:4; 330 E1 coding sequence begins at nucleotide position 1992 and ends at nucleotide base 2483 and SAg coding sequence begins at base 2484). The amino acid sequence of the encoded chimeric antigen polypeptide is also displayed in FIGS. 3B–3I and in SEQ ID NO:5.

Figure 4A:
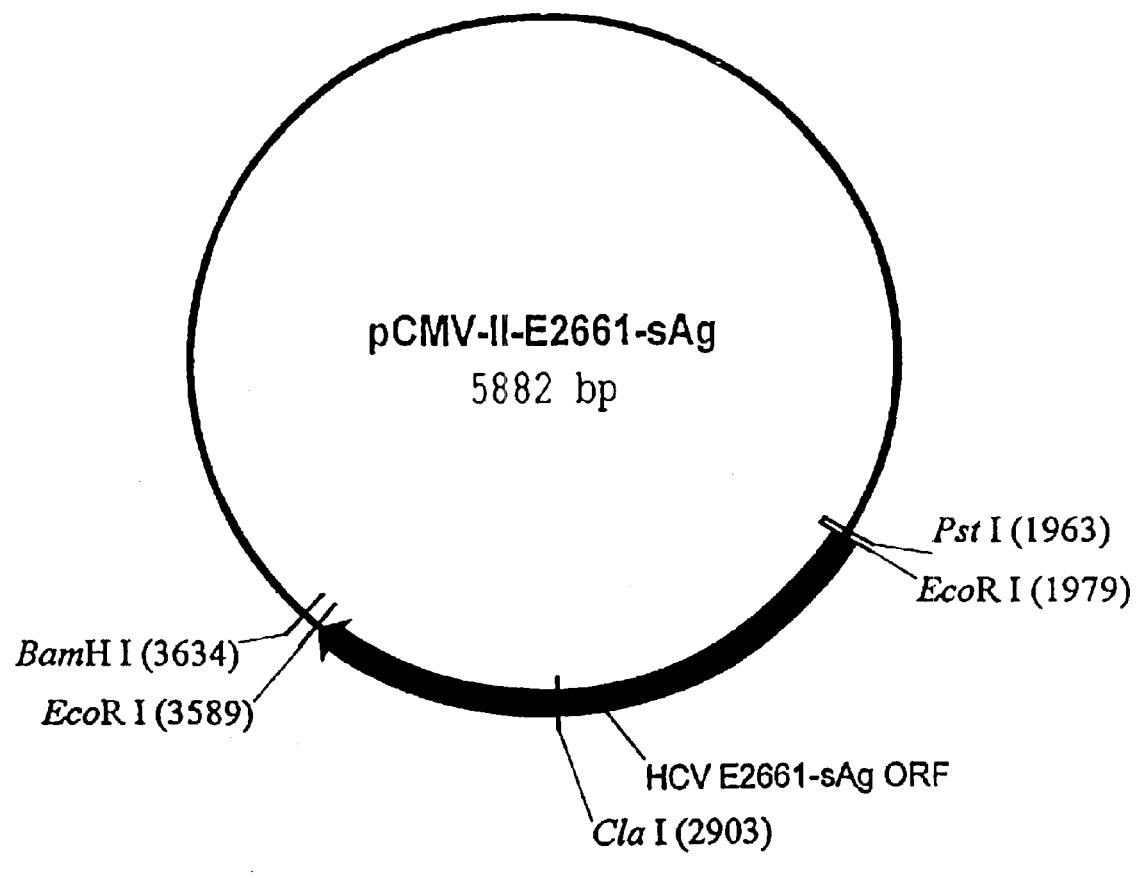

FIGS. 4A and 4B–4F show the expression vector pCMV-II-E2661-sAg (FIG. 4A) and its nucleotide sequence (FIGS. 4B–4F and SEQ ID NO:6; 661 E2 coding sequence begins at nucleotide position 1997 and ends at nucleotide base 2900, and sAg coding sequence begins at base 2907). The amino acid sequence of the encoded chimeric antigen polypeptide is also displayed in FIGS. 4B–4F and in SEQ ID NO:7.

Figure 1A:
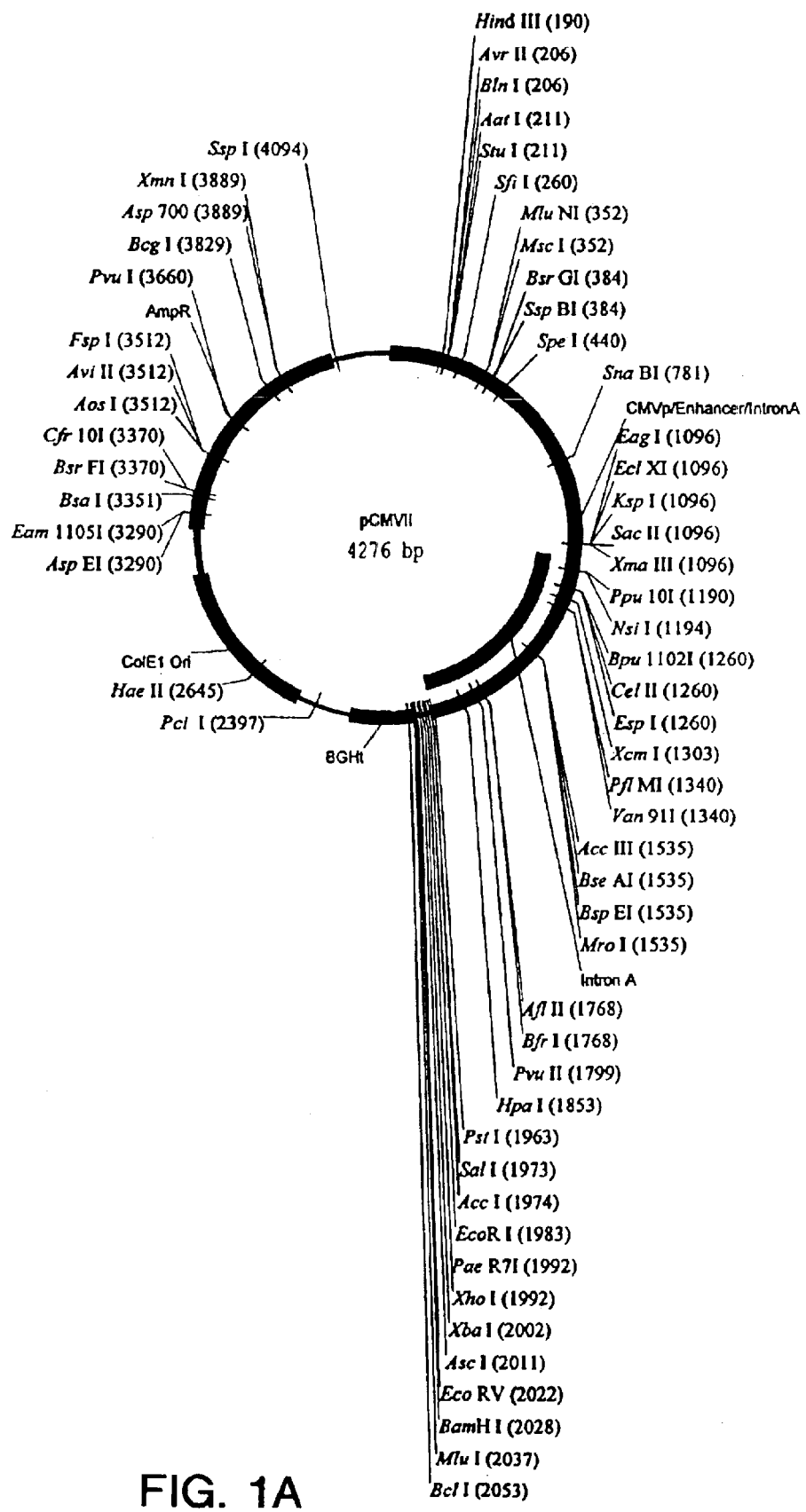
Figure 2A:
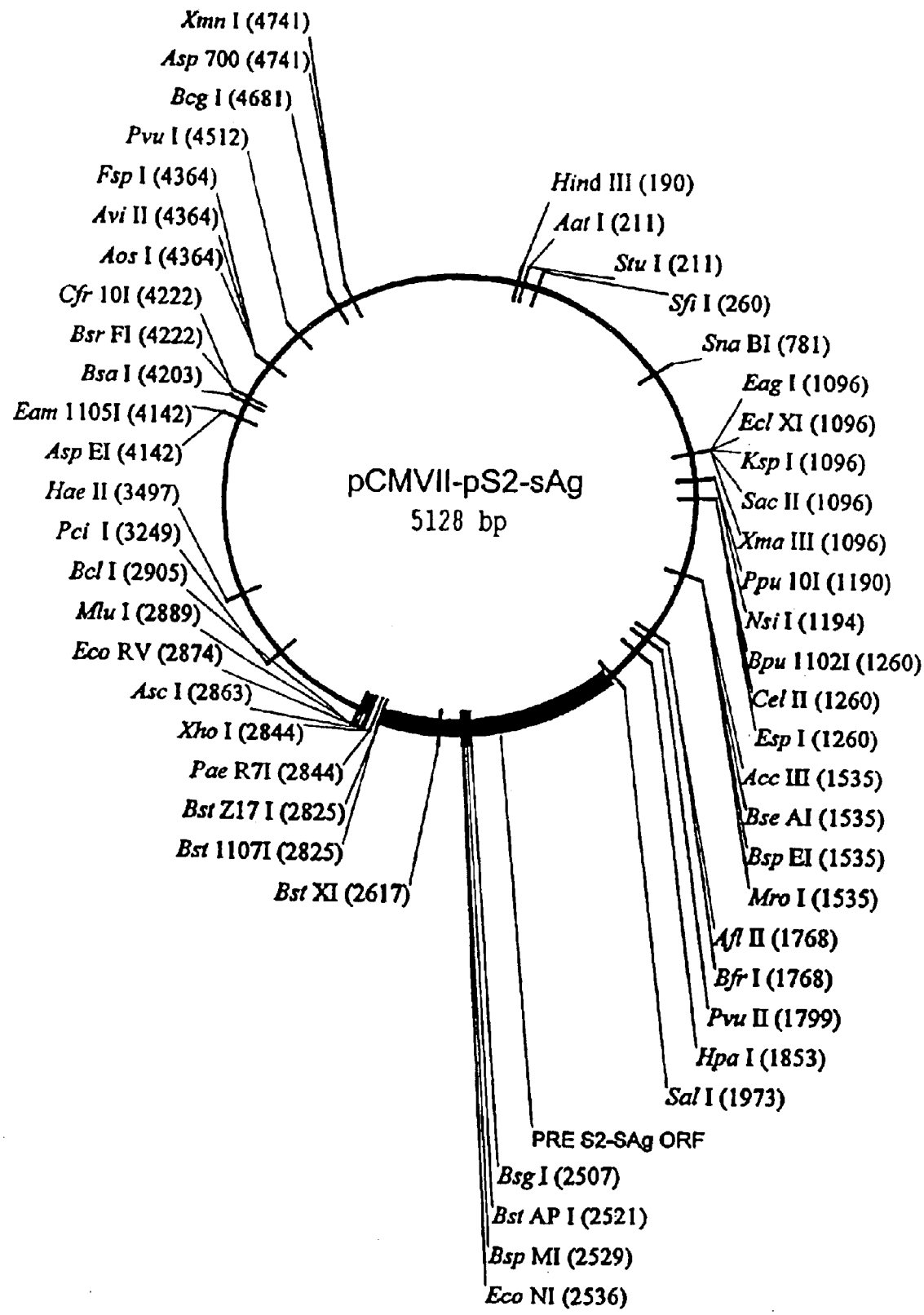
Figure 3A:
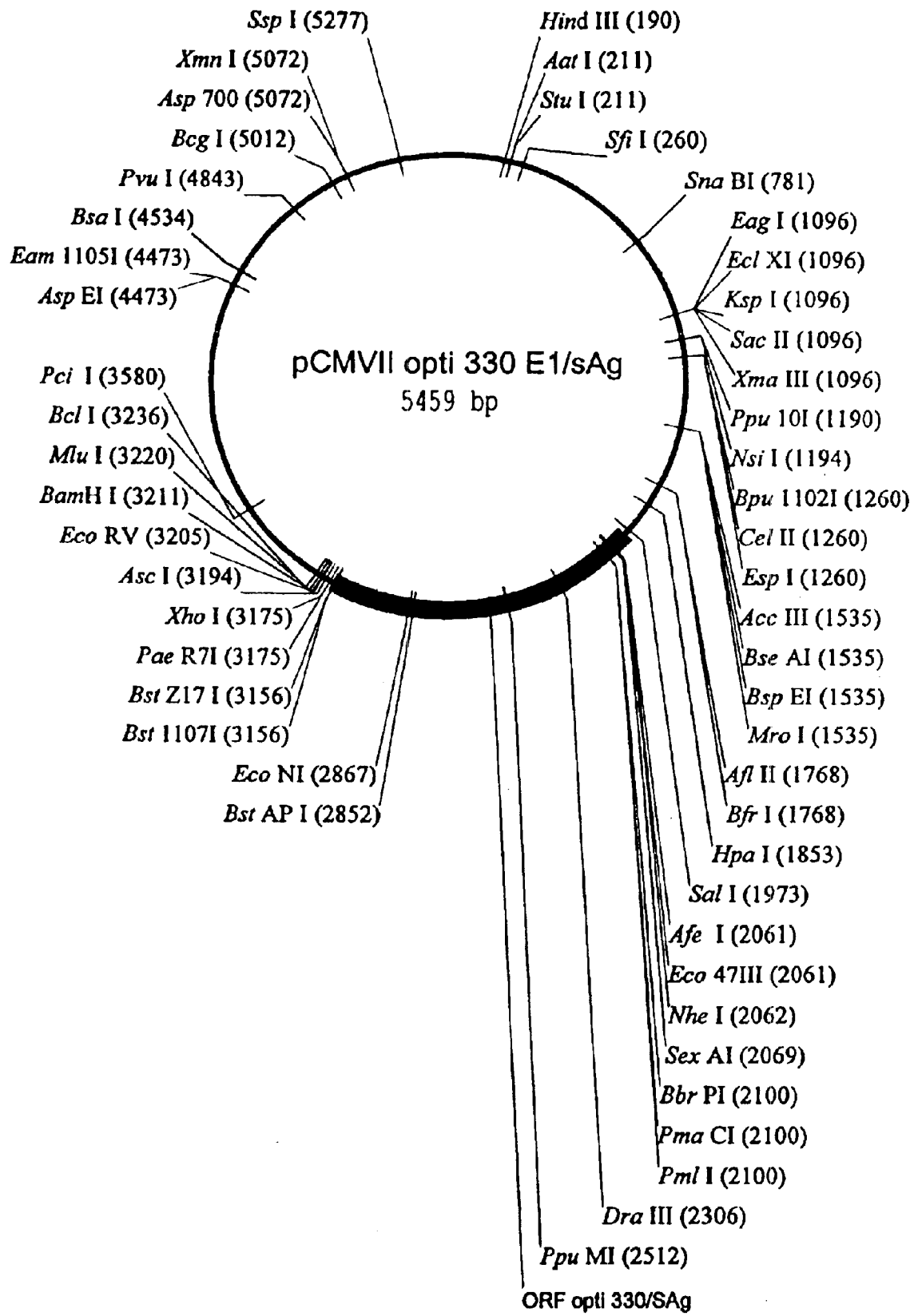

All publications, patents and patent applications cited herein, whether supra or infra, are hereby incorporated by reference in their entireties.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

Standard abbreviations for nucleotides and amino acids are used in this specification. For example, the following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The terms "polypeptide" and "protein" are used interchangeably herein and refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. HCV encodes a single polyprotein having more than 3000 amino acid residues (Choo et al. *Science* (1989) 244:359–362; Choo et al. *Proc. Natl. Acad. Sci. USA* (1991) 88:2451–2455; Han et al. *Proc. NatL Acad. Sci. USA* (1991) 88:1711–1715). The polyprotein is processed co- and post-translationally into both structural and non-structural (NS) proteins.

In particular, several proteins are encoded by the HCV genome. The order and nomenclature of the cleavage products of the HCV polyprotein is as follows: $NH_2$—C-E1-E2-NS2-NS3-NS4a-NS4b-NS5a-NS5b-COOH. Initial cleavage of the polyprotein is catalyzed by host proteases which liberate three structural proteins, the N-terminal nucleocapsid protein (termed "Core") and two envelope glycoproteins, "E1" (also known as E) and "E2" (also known as E2/NS1), as well as nonstructural (NS) proteins that contain the viral enzymes. The NS regions are termed NS2, NS3, NS4 and NS5. NS2 is an integral membrane protein with proteolytic activity. NS2, either alone or in combination with NS3, cleaves the NS2-NS3 sissle bond which in turn generates the NS3 N-terminus and releases a large polyprotein that includes both serine protease and RNA helicase activities. The NS3 protease serves to process the remaining polyprotein. Completion of polyprotein maturation is initiated by autocatalytic cleavage at the NS3-NS4a junction, catalyzed by the NS3 serine protease. Subsequent NS3-mediated cleavages of the HCV polyprotein appear to involve recognition of polyprotein cleavage junctions by an NS3 molecule of another polypeptide. In these reactions, NS3 liberates an NS3 cofactor (NS4a), two proteins with unknown function (NS4b and NS5a), and an RNA-dependent RNA polymerase (NS5b). Any one of these proteins, as well as immunogenic fragments thereof, will find use with the subject chimeric antigens.

The polypeptide for use in the chimeric antigens need not be physically derived from HCV, but may be synthetically or recombinantly produced. Moreover, the polypeptide may be derived from any of the various HCV strains, such as from strains 1, 2, 3 or 4 of HCV (described further below). A number of conserved and variable regions are known between these strains and, in general, the amino acid sequences of epitopes derived from these regions will have a high degree of sequence homology, e.g., amino acid sequence homology of more than 30%, preferably more than 40%, preferably more than 50%, preferably more than about 75%, more preferably more than about 80%–85%, preferably more than about 90%, and most preferably at least about 95%–98% sequence identity, or more, when the two sequences are aligned. Thus, for example, the term "E2" polypeptide refers to the native E2 protein from any of the various HCV strains, as well as E2 analogs, muteins and immunogenic fragments, as defined further below.

The terms "analog" and "mutein" refer to biologically active derivatives of the reference molecule, or fragments of such derivatives, that retain desired activity, such as immunological activity as described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publ. No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5–10 conservative or non-conservative amino acid substitutions, or even up to about 15–25 conservative or non-conservative amino acid substitutions, or any integer between 5–25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5–10 contiguous amino acid residues of the full-length molecule, preferably at least about 15–25 contiguous amino acid residues of the full-length molecule, and most preferably at least about 20–50 or more contiguous amino acid residues of the full-length molecule, that define an epitope, or any integer between 5 amino acids and the full-length sequence, provided that the fragment in question retains the ability to elicit an immune response as defined below. For example, preferred immunogenic fragments, include but are not limited to fragments of HCV Core that comprise, e.g., amino acids 10–45, 10–53, 67–88, 81–130, 86–100, 120–130, 121–135 and 121–170 of the polyprotein, numbered relative to the HCV-1 a sequence presented in Choo et al. (1991) *Proc Natl Acad Sci USA* 88:2451, as well as defined epitopes derived from the c33c region of the HCV polyprotein, as well as any of the other various epitopes identified from the HCV core, E1, E2, NS3 and NS4 regions. See, e.g., Chien et al. *Proc. Natl. Acad. Sci. USA* (1992) 89:10011–10015; Chien et al. *J. Gastroent. Hepatol.* (1993) 8:S33–39; Chien et al. International Publ. No. WO 93/00365; Chien, D. Y. International Publ. No. WO 94/01778; and U.S. Pat. No. 6,150,087, incorporated herein by reference in its entirety. Representative fragments of E1 and E2 polypeptides include C-terminally truncated variants of these molecules, such as E1 polypeptides terminating at, e.g., amino acids 369 and lower, such as e.g., E1 polypeptides ending in amino acids 351, 352, 353 and so on, and E2 polypeptides, terminating at about amino acids 730, such as E2 polypeptides ending in for example amino acids 716, 717, 718 and so on. These molecules are described in, e.g., U.S. Pat. No. 6,121,020, incorporated herein by reference in its entirety.

"Antigenic determinant" refers to the site on an antigen or hapten to which a specific antibody molecule or specific cell surface receptor binds.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, will stimulate a host's immune system to make a cellular antigen-specific immune response when the antigen is presented, or a humoral antibody response. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol.* 23:709–715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. Preferably, a conformnational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publ. Nos. WO 96/04301, WO 94/01778, WO 95/33053, WO 92/08734, which applications are herein incorporated by reference in their entireties.

As used herein the term "T-cell epitope" refers to a feature of a peptide structure which is capable of inducing T-cell immunity towards the peptide structure or an associated hapten. T-cell epitopes generally comprise linear peptide determninants that assume extended conformations within the peptide-binding cleft of MHC molecules, (Unanue et al., *Science* (1987) 236:551–557). Conversion of polypeptides to MHC class II-associated linear peptide determinants (generally between 5–14 amino acids in length) is termed "antigen processing" which is carried out by antigen presenting cells (APCs). More particularly, a T-cell epitope is defined by local features of a short peptide structure, such as primary amino acid sequence properties involving charge and hydrophobicity, and certain types of secondary structure, such as helicity, that do not depend on the folding of the entire polypeptide. Further, it is believed that short peptides capable of recognition by helper T-cells are generally amphipathic structures comprising a hydrophobic side (for interaction with the MHC molecule) and a hydrophilic side (for interacting with the T-cell receptor), (Margalit et al., Computer Prediction of T-cell Epitopes, *New Generation Vaccines* Marcel-Dekker, Inc, ed. G. C. Woodrow et al., (1990) pp. 109–116) and fuirther that the amphipathic structures have an α-helical configuration (see, e.g., Spouge et al. *J. Immunol.* (1987) 138:204–212; Berkower et al. *J. Immunol.* (1986) 136:2498–2503).

Hence, segments of proteins which include T-cell epitopes can be readily predicted using numerous computer programs. (See e.g., Margalit et al., Computer Prediction of T-cell Epitopes, *New Generation Vaccines* Marcel-Dekker, Inc, ed. G. C. Woodrow et al., (1990) pp. 109–116). Such programs generally compare the amino acid sequence of a peptide to sequences known to induce a T-cell response, and search for patterns of amino acids which are believed to be required for a T-cell epitope.

An "immunological response" to a polypeptide or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition, such as an immunogenic composition, or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189–4199; Doe et al., *Eur. J. Immunol.* (1994) 24:2369–2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic" polypeptide or composition is one which elicits an immunological response as defined above.

A "recombinant" protein is a protein which retains the desired activity and which has been prepared by recombinant DNA techniques as described herein. In general, the gene of interest is cloned and then expressed in transformed organisms, as described further below. The host organism expresses the foreign gene to produce the protein under expression conditions.

By "isolated" is meant, when referring to a polypeptide, that the indicated molecule is separate and discrete from the whole organism with which the molecule. is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%–85%, preferably at least about 90%, and most preferably at least about 95%–98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter= none; strand=both; cutoff=60; expect=10; Matrix= BLOSUM62; Descriptions=50 sequences; sort by=HIGH SCORE; Databases=non-redundant, GenBank+EMBL+ DDBJ+PDB+GenBank CDS translations+Swiss protein+ Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

By "nucleic acid immunization" is meant the introduction of a nucleic acid molecule encoding one or more selected antigens into a host cell, for the in vivo expression of the antigen or antigens. The nucleic acid molecule can be introduced directly into the recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, chimeric antigens which combine HBsAg with portions of HCV proteins enhance the presentation to the immune system of weakly immunogenic HCV proteins due to the strong antigenicity of HBsAg. Virus-like particles typically contain a membrane envelope in which are embedded one or more viral envelope proteins. Virus-like particles are secreted by a cell infected with a virus or a cell transfected with a nucleic acid molecule encoding one or more viral proteins.

Virus-like particles are an especially advantageous form of antigen presentation. Virus-like particles containing HBsAg chimeras combine the highly antigenic nature of HBsAg itself with the desirable presentation of other antigens at the surface of a particulate preparation.

The present invention provides methods and materials which enable the production of chimeric HBV/HCV antigens in the form of virus-like particles for the production of immunogenic compositions, such as vaccines. Utilizing co-expression of HBsAg together with the chimeric antigens, it is now possible to include large segments of HCV envelope glycoproteins fused to HBsAg in the form of virus-like particles. Such particles are especially well suited for use in immunogenic compositions.

The strategy for preparing HBV/HCV virus-like particles depends first on the production of one or more chimeric antigens for display in the particles. Such chimeric antigens are fusion proteins that comprise a substantially complete S domain of an HBsAg polypeptide (termed "sAg" herein) and an immunogenic HCV polypeptide or fragment thereof. An S domain of HBsAg, or any other polypeptide of the invention, is "substantially complete" if it contains the native sequence of the polypeptide with or without minor deletions of one or a few amino acids from either the N-terminal or C-terminal regions or within the polypeptide. For example the HBsAg S domain can be truncated by a few amino acids, i.e., up to about 3, 5, 7, or 10 amino acids, without greatly affecting either its antigenicity or ability to cause the formation of virus-like particles. Linker sequences of any desired length, preferably no more than a few amino acids, can be added between the polypeptides joined together to form the fusion protein. Either preS2 (formerly called preS) or both preS2 and preS1 domains of HBsAg can also be included at the amino terminus of the HBsAg polypeptide if desired.

Valenzuela, et al. (1982) *Nature* 298:347–350, describes the gene for HbsAg. See, also, Valenzuela, et al. (1979) *Nature* 280:815–819. Proteins derived from the HBV surface, such as the surface antigen, sAg, as well as the presurface sequences, preS1 and preS2, and any combination of these sequences, can spontaneously form particles upon expression in a suitable host cell, such as upon expression in mammalian, insect, yeast or Xenopus cells. Thus, as explained above, HCV/HBV virus-like particles for use in the present invention can include particle-forming polypeptides of sAg, preS1 and/or preS2, as well as particle-forming polypeptides from any combination of the above, such as sAg/preS1, sAg/preS2, and sAg/preS1/preS2. See, e.g., "HBV Vaccines—from the laboratory to license: a case study" in Mackett, M. and Williamson, J. D., *Human Vaccines and Vaccination*, pp. 159–176, for a discussion of HBV structure; and U.S. Pat. Nos. 4,722,840, 5,098,704, 5,324,513, 5,965,140, incorporated herein by reference in their entireties, Beames et al., *J. Virol.* (1995) 69:6833–6838, Birnbaum et al., *J. Virol.* (1990) 64:3319–3330, Zhou et al., *J. Virol.* (1991) 65:5457–5464, for descriptions of the recombinant production of various HBV particles.

HCV has a genome that contains a single open reading frame of approximately 9.5 kb, which is transcribed into a polyprotein. The HCV polyprotein is cleaved to form at least ten distinct products, which are $NH_2$-Core-E1-E2-p7-NS2-NS3-NS4a-NS4b-NS5a-NS5b-COOH. The HCV E1 and E2 proteins are postranslationally glycosylated. The full-length sequence of the polyprotein is disclosed in European Publ. No. 388,232 and U.S. Pat. No. 6,150,087, incorporated herein by reference in their entireties. Moreover, sequences for the above HCV polyprotein products, and immunogenic polypeptides derived therefrom, are known (see, e.g., U.S. Pat. No. 5,350,671, incorporated herein by reference in its entirety). For example, a number of general and specific immunogenic polypeptides, derived from the HCV polyprotein, have been described. See, e.g., Houghton et al., European Publ. Nos. 318,216 and 388,232; Choo et al. *Science* (1989) 244:359–362; Kuo et al. *Science* (1989) 244:362–364; Houghton et al. *Hepatology* (1991) 14:381–388; Chien et al. *Proc. Natl. Acad. Sci. USA* (1992) 89:10011–10015; Chien et al. *J. Gastroent. Hepatol.* (1993) 8:S33–39; Chien et al., International Publ. No. WO 93/00365; Chien, D. Y., International Publ. No. WO 94/01778. These publications provide an extensive background on HCV generally, as well as on the manufacture and uses of HCV polypeptide immunological reagents. For brevity, therefore, the disclosure of these publications is incorporated herein by reference.

Any desired HCV polypeptide can be utilized as part of the chimeric antigen, including, for example, the E1 and/or E2 envelope glycoproteins of HCV. The E1 glycoprotein corresponds to amino acid residues 192 to 383, and E2 extends from approximately amino acid 384 to amino acid 746 in most HCV strains. See Choo et al. (1991) Proc. Natl. Acad. Sci. USA 88:2451–2455. Preferred E1 polypeptides are those beginning at any amino acid residue from any of positions 192–360 of the HCV polyprotein and extending any desired length up to and including residue 383. Preferred E2 polypeptides are those beginning at any amino acid residue from positions 384–725 of the HCV polyprotein and extending any desired length up to and including residue 746. A fragment of the E1 or E2 glycoproteins which is utilized in the chimeric antigen should preferably comprise an epitope, domain, or other structural unit which is immunogenic.

An E1 or E2 glycoprotein or fragment thereof for use in a chimeric antigen, will preferably retain or resemble its native conformation. If a substantially native conformation is retained for the HCV polypeptide in the fusion protein containing HBsAg, then antibodies generated to the HCV polypeptide will recognize and bind to the corresponding polypeptide in HCV.

Other HCV polypeptides may also be used in the chimeric antigens of the invention. For example, HCV polypeptides derived from the Core region, such as polypeptides derived from the region found between amino acids 1–191; amino acids 10–53; amino acids 10–45; amino acids 67–88; amino acids 86–100; 81–130; amino acids 121–135; amino acids 120–130; amino acids 121–170; and any of the Core epitopes identified in, e.g., Houghton et al., U.S. Pat. No. 5,350,671; Chien et al. *Proc. Natl. Acad. Sci. USA* (1992) 89:10011–10015; Chien et al. *J. Gastroent. Hepatol.* (1993) 8:S33–39; Chien et al., International Publ. No. WO 93/00365; Chien, D. Y., International Publ. No. WO 94/01778; and U.S. Pat. No. 6,150,087, the disclosures of which are incorporated herein by reference in their entireties, will find use with the subject chimeric molecules.

Additionally, polypeptides derived from the nonstructural regions of the virus will also find use herein. The NS3/4a region of the HCV polyprotein has been described and the amino acid sequence and overall structure of the protein are disclosed in Yao et al. *Structure* (November 1999) 7:1353–1363. See, also, Dasmahapatra et al., U.S. Pat. No. 5,843,752, incorporated herein by reference in its entirety. As explained above, either the native sequence or immunogenic analogs can be used in the subject formulations. Dasmahapatra et al., U.S. Pat. No. 5,843,752 and Zhang et al., U.S. Pat. No. 5,990,276, both describe analogs of NS3/4a and methods of making the same.

Additionally, multiple epitope fusion antigens (termed "MEFAs"), as described in International Publ. No. WO 97/44469, may be used in the subject chimeras. Such MEFAs include multiple epitopes derived from two or more of the various viral regions. The epitopes are preferably from more than one HCV strain, thus providing the added ability to protect against multiple strains of HCV in a single vaccine.

Moreover, polypeptides for use in the subject chimeras may be derived from the NS3 region of the HCV polyprotein. A number of such polypeptides are known, including, but not limited to polypeptides derived from the c33c and c100 regions, as well as fusion proteins comprising an NS3 epitope, such as c25. These and other NS3 polypeptides are usefuil in the present compositions and are known in the art and described in, e.g., Houghton et al, U.S. Pat. No. 5,350,671; Chien et al. *Proc. Natl. Acad. Sci. USA* (1992) 89:10011–10015; Chien et al. *J. Gastroent. Hepatol.* (1993) 8:S33–39; Chien et al., International Publ. No. WO 93/00365; Chien, D. Y., International Publ. No. WO 94/01778; and U.S. Pat. No. 6,150,087, the disclosures of which are incorporated herein by reference in their entireties.

It is readily apparent that a multitude of HCV polypeptides may be used in the subject chimeric molecules or may be coadministered therewith, in order to provide an immune response against the HCV antigen in question.

As explained above, the HCV antigens may be used in their entireties or immunogenic fragments thereof, as well as immunogenic variants, can be combined with an HBsAg polypeptide to form the chimeric antigen by fusion of the gene sequences encoding the desired polypeptide sequences, in proper reading frame, using standard techniques available in the art. Thus, the HBV or HCV polypeptides described for use in the invention can be modified by deletions, insertions, or conservative amino acid substitutions, provided that a substantially native conformation is retained for the HCV epitope intended for use as an immunogen. Preferably, the HCV polypeptide or polypeptide fragment is chosen so that, when expressed in a fusion protein with HBsAg, it substantially retains the native conformation of the corresponding portion of the HCV protein from which it was derived, i.e., the approximate conformation existing in a mature HCV virion.

It should be noted that for convenience, the various HCV regions are generally defined with respect to the amino acid number relative to the polyprotein encoded by the genome of HCV-1a, as described in Choo et al. (1991) *Proc Natl Acad Sci USA* 88:2451, with the initiator methionine being designated position 1. However, the polypeptides for use with the present invention are not limited to those derived from the HCV-1a sequence. Any strain or isolate of HCV can serve as the basis for providing antigenic sequences for use with the invention. In this regard, the corresponding regions in another HCV isolate can be readily determined by aligning sequences from the two isolates in a manner that brings the sequences into maximum alignment.

Various strains and isolates of HCV are known in the art, which differ from one another by changes in nucleotide and amino acid sequence. For example, isolate HCV J1.1 is described in Kubo et al. (1989) Japan. Nucl. Acids Res. 17:10367–10372; Takeuchi et al. (1990) Gene 91:287–291; Takeuchi et al. (1990) J. Gen. Virol. 71:3027–3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524–9528 and Takamizawa et al., (1991) J. Virol. 65:1105–1113, respectively. HCV-1 isolates are described by Choo et al. (1990) Brit. Med. Bull. 46:423–441; Choo et al. (1991) Proc. Natl. Acad. Sci. USA 88:2451–2455 and Han et al. (1991) Proc. Natl. Acad. Sci. USA 88:1711–1715. HCV isolates HC-J1 and HC-J4 are described in Okamoto et al. (1991) Japan J. Exp. Med. 60:167–177. HCV isolates HCT 18~, HCT 23, Th, HCT 27, EC1 and EC10 are described in Weiner et al. (1991) Virol. 180:842–848. HCV isolates Pt-1, HCV-K1 and HCV-K2 are described in Enomoto et al. (1990) Biochem. Biophys. Res. Commun. 170:1021–1025. HCV isolates A, C, D & E are described in Tsukiyama-Kohara et al. (1991) Virus Genes 5:243–254.

Coding sequences for naturally occurring HCV polypeptides for use in the nucleic acid molecules or vectors of the invention can be obtained from any of the above cited strains of HCV or from newly discovered isolates isolated from tissues or fluids of infected patients. In choosing HCV polypeptides or their fragments from different HCV strains for use in a chimeric antigen of the invention, it is preferred that the nucleotide or amino acid sequences be aligned for maximum overlap between strains. This can be accomplished, for example, by compensating for insertions or deletions of amino acids so that the greatest possible overlap between strains is obtained prior to selecting a sequence for incorporation in the chimeric antigen. If a sequence disclosed herein is selected from another HCV strain, then preferably the corresponding sequence, i.e., the sequence which is aligned to be identical at the greatest possible number of residues to the disclosed sequence, will be selected. Modified sequences which do not occur in nature can also be used. A "nucleic acid molecule" according to the invention can be any nucleic acid such as DNA or RNA, either single or double stranded, or any analog or chemical derivative thereof which encodes a fusion protein of the invention or portion thereof or any HBsAg or portion thereof.

Nucleic acid molecules of the invention can be cloned into expression vectors and transformed into, for example, bacterial, yeast, plant, insect, or mammalian cells so that the chimeric antigens and virus-like particles of the invention can be expressed in and isolated from cell culture. Nucleic acid molecules can be contained within a plasmid, such as pBR322, pUC, ColE1, or related plasmids such as pCMV6a (see U.S. Pat. No. 5,688,688) or plasmids derived therefrom. Nucleic acid molecules can also be contained within a viral vector, such as any vector derived from adenovirus, Sindbis virus, simian virus 40, cytomegalovirus, and retroviruses such as murine sarcoma virus, mouse mammary tumor virus, Moloney murine leukemia virus, and Rous sarcoma virus. Bacterial vectors, such as Salmonella ssp., *Yersinia enterocolitica*, Shigella spp., *Vibrio cholerae*, Mycobacterium strain BCG, and *Listeria monocytogenes* can also be used. Minichromosomes such as MC and MC1, bacteriophages, cosmids, and replicons can be used as well.

Any suitable expression vector can be constructed or utilized to express any form of HBsAg or any chimeric antigen of the invention. A preferred vector is pCMVII, a pUC19-based cloning vector designed for expression in mammalian cells. pCMVII comprises the following elements: human CMV IE enhancer/promoter, human CMV intron A, a human tissue plasminogen activator (tPA) leader, a bovine growth hormone poly A terminator (BGHt), a ColE1 origin of replication, and an Amp R ampicillin resistance gene (FIGS. 1A and 1B–1F, SEQ ID NO:1). pCMVII-pS2-sAg can be used for expression of preS2-HBsAg (FIGS. 2A and 2B–2I, SEQ ID NOS:2 and 3). In pCMVII-pS2-sAg, the coding sequences for the preS2 and S domains of HBsAg have been inserted into pCMVII between CMV intron A and BGHt; this vector can also be modified by adding the coding sequences for the preS1 domain or removing the preS2 domain. Chimeric antigens containing HBsAg together with epitopes of HCV proteins can be constructed similar to pCMVII opti 330 E1/sAg (FIGS. 3A and 3B–3I, SEQ ID NOS:4 and 5) or pCMVII-E2661-sAg (FIGS. 4A and 4B–4F, SEQ ID NOS:6 and 7). These vectors are provided by way of example and are not intended to limit the scope of the invention. Isolated and purified pCMVII vectors containing an insert encoding HBsAg or a chimeric antigen can be dissolved in sterile 0.9% saline buffer or another suitable buffer prior to use.

The expression of chimeric antigens for use as immunogens requires transfection of eukaryotic cells with an expression vector. Any suitable eukaryotic cell line can be used, for example CHO cells or COS cells. A nucleic acid molecule that encodes a chimeric antigen can be incorporated into any vector suitable for transfection, for example a plasmid vector or a viral vector. If a viral vector is used, it will preferably produce defective, non-infectious viral particles so that the risk of contamination with infectious virus in a vaccine preparation is minimized.

Transfection can be performed by any known method and can result in either transient transfection or stable transfection. Stable transfection is preferred to establish a cell line producing HBV/HCV virus-like particles. Methods for obtaining stable transfection are well known and include, for example, selection for spontaneously stable transfectants, transfection with immortalizing genes (see, e.g., Katakura et al., Methods Cell Biol. (1998) 57:69–91), and selection for genes providing resistance to antibiotics such as hygromycin B and neomycin. A preferred method for CHO cells involves selection for cells transfected with dihydrofolate reductase followed by amplification of the transgene using methotrexate (see Wurm et al., Ann. N.Y. Acad. Sci. (1996) 782:70–78).

Co-expression of chimeric antigens with HBsAg results in formation and secretion of virus-like particles. Optimum secretion of virus-like particles requires a sufficient quantity of expression of HBsAg in relation to the expression of chimeric antigen, and higher quantities of HBsAg expression generally improve the efficiency of chimeric antigen secretion. Secretion of chimeric antigen as virus-like particles can be optimized by varying the ratio of the coding sequences for HBsAg to the coding sequences for the chimeric antigen. Generally, useful secretion of virus-like particles will be obtained at a ratio of HBsAg coding sequences to chimeric antigen coding sequences of about 1:1, 2:1, 3:1, 4:1, 5:1, 7:1, 10:1, 20:1, 30:1, 40:1, 50:1, or 100:1. Ratios less than 1:1 provide reduced yield of virus-like particles containing chimeric antigen, while high ratios greater than 100:1 dilute out the chimeric antigen and eventually will limit the utility of the particles because of dilution of the chimeric antigen with HBsAg.

One strategy for transfecting host cells with the vectors of the invention, either for in vitro production of virus-like particles or for immunization of a host organism using a nucleic acid vaccine, is to provide two or more separate vectors, one that encodes HBsAg and one or more that each encode a chimeric antigen. Another strategy is to include both HBsAg and one or more chimeric antigens in a single construct. For example, an expression vector having a single open reading frame could have a coding sequence for HBsAg under control of a promoter, followed by sequences encoding one or more chimeric antigens, each preceded by an internal ribosomal entry site (IRES, see, e.g., Martinez-Salas (1999) Curr. Op. Biotechnol. 10: 458–464). Thus, the invention encompasses the use either of a single immunogenic polypeptide or multiple distinct immunogenic polypeptides in a single virus-like particle. Optionally, expression of immunogenic polypeptides can be regulated by including promoter and/or enhancer sequences in the expression vector which respond to activators introduced into the transfected cells.

Cells that have been transfected with plasmid or viral vectors expressing chimeric HBV/HCV antigens together with HBsAg can be analyzed to determine whether each antigen is being expressed and secreted in the form of virus-like particles. Any standard immunological assay can be used to detect HBV and HCV antigens, including, for example, chemiluminescence assays (see, e.g., Magic Lite assay in Examples 1–4; Woodhead, J. S. and Weeks, I. (1989) J. Biolumin. Chemilumin. 4:611–14), ELISA, and radioimmunoassays. Where an antigen is produced by transfected cells in culture, the amount of secretion of the antigen into the culture medium can be ascertained by comparing the amount of antigen in the culture medium with the amount remaining in lysed cells. The presence of virus-like particles can be confirmed by sedimentation of such particles from the culture medium into a density gradient, for example a sucrose density gradient (see Examples 1–3).

While expression in a mammalian cell line is preferred, other systems may also be employed to express virus-like particles of the invention. For example, yeast cell culture may be used (see U.S. Pat. No. 5,098,704, incorporated herein by reference), in which case virus-like particles can be harvested by disrupting the cells using agitation with glass beads or another suitable method.

Generally, the proteins of the subject invention will naturally aggregate to form particles in the expression host. The particles may be enveloped having a lipid membrane coat, which may or may not include membrane proteins encoded by the virus. Alternatively, the particles may not include the lipid membrane or the membrane may be present initially or may be removed, in whole or in part. U.S. Pat. Nos. 4,722,840 and 5,965,140, incorporated herein by reference in their entireties, describe hybrid particles comprised of a particle-forming fragment of a structural protein from a virus, such as a particle-forming fragment of hepatitis B virus (HBV) surface antigen (HBsAg), fused to a heterologous polypeptide.

HBV/HCV virus-like particles can be purified after being harvested from a culture medium or cell suspension and before being used in an immunogenic composition. Any method can be used that is known to separate virus-like particles or viruses from surrounding proteins, lipids, nucleic acids, membranes, intact cells, and the like. Especially preferred are affinity chromatography methods; for example, an immobilized monoclonal antibody specific for HBsAg can be used. Additional suitable methods are gel filtration chromatography, ion exchange chromatography, and density gradient sedimentation. Methods for isolated chimeric virus-like particles are described in, e.g., U.S. Pat. Nos. 4,722,840 and 5,965,140, incorporated herein by reference in their entireties.

Any composition of the invention, such as a fusion protein, a virus-like particle, or a nucleic acid molecule, can be used as an "immunogenic composition." An immunogenic composition preferably generates an immune response, as defined above, such as an antibody or a T-cell response, in a mammal to whom it is administered. An immunogenic composition of the invention can be, but is not limited to, a vaccine or a combination vaccine, e.g., an immunogenic composition that produces an immune response to more than one immunogen. Moreover, the chimeric proteins of the invention may be formulated into "antigenic compositions," e.g., compositions that include epitopes to which a specific antibody molecule or specific cell surface receptor binds.

Immunogenic and antigenic compositions containing HBV/HCV virus-like particles or a nucleic acid molecule encoding proteins which form virus-like particles can be administered to a mammal, such as a mouse, rabbit, baboon, chimpanzee, or human, to elicit anti-HCV antibodies in vivo. Injection of an immunogenic composition of the invention preferably results in the synthesis of virus-like particles in the host. Therefore, Compositions comprising nucleic acids should include sequences encoding both HBsAg and chimeric antigens such as HBsAg-E1 and/or HBsAg-E2 fusion proteins, as well as fusions with other HCV polypeptides. The weight:weight ratio of nucleic acids encoding HBsAg to nucleic acids encoding chimeric antigens is preferably 1:1, 2:1, 5:1, 10:1, 20:1, 30:1, 50:1, or 100:1 and results in the formation of virus-like particles in the cells of the host and their secretion within the host. More preferably, the ratio is in the range of 5:1 to 20:1.

Virus-like particles or nucleic acid molecules of an antigenic or immunogenic composition can be combined with adjuvants, immunostimulatory molecules, or carriers, including but not limited to, MF59 (described below), poly(dl-lactide-co-glycolide) microparticles (PLG, see, e.g., Delgado et al. (1999) Vaccine 17: 2927–2938), LT toxins, immune stimulating complexes (ISCOMS, see, e.g., Mowat et al. (1999) Immunol. Lett. 65: 133–140), and QS21 (see Singh & O'Hagan (1999) Nat. Biotechnol. 17: 1075–1081).

For example, preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's, Adjuvant (CFA) and Incomplete Freund's Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; (6) detoxified mutants of a bacterial ADP-ribosylating toxin such as a cholera toxin (CT), a pertussis toxin (PT), or an *E. coli* heat-labile toxin (LT), particularly LT-K63, LT-R72, CT-S109, PT-K9/G129; see, e.g., WO 93/13302 and WO 92/19265; (7) other substances that act as immunostimulating agents to enhance the effectiveness of the composition; and (8) microparticles with adsorbed macromolecules, as described in copending U.S. patent application Ser. No. 09/285,855 (filed Apr. 2, 1999) and international Patent Application Serial No. PCT/US99/17308 (filed Jul. 29, 1999). Alum and MF59 are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

An immunogenic composition may also comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Liposomes, such as those described in U.S. Pat. No. 5,422,120, WO 95/13796, WO 91/14445, or EP 524,968 B1, as well as poly(dl-lactide-co-glycolide) microparticles (PLG, see, e.g., Delgado et al. (1999) Vaccine 17: 2927–2938), can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates.

Compositions of the invention generally contain pharmaceutically acceptable excipients, such as water, saline, glycerol, and ethanol, as well as substances such as wetting agents, emulsifying agents, or pH buffering agents.

The chimeric molecules of the present invention may be used for nucleic acid immunization, to generate an appropriate immune response, such as to activate HCV-specific T cells, using standard gene delivery protocols. Any method known in the art can be employed to package and deliver nucleic acid molecules of the invention, including nucleic acid molecules in an immunogenic composition. Methods for gene delivery are known in the art. See, e.g., U.S. Pat. Nos. 5,399,346, 5,580,859, 5,589,466, incorporated by reference herein in their entireties. For example, the coding sequences can be packaged in a viral vector, combined with lipid, peptoid excipients, PLG formulations, or gold particles. Preferably, an immunogenic composition is delivered as naked DNA or naked RNA. The expressed immunogenic polypeptide is preferably presented to the host immune system with native post-translational modifications, structure, and conformation.

For example, the constructs can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta*. (1991) 1097:1–17; Straubinger et al., in *Methods of Enzymology* (1983), Vol.101, pp.512–527.

Liposomal preparations for use with the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Feigner et al., *Proc. Natl. Acad. Sci. USA* (1987) 84:7413–7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes. The various liposome-nucleic acid complexes are prepared using methods known in the art. See, e.g., Straubinger et al., in METHODS OF IMMUNOLOGY (1983), Vol. 101, pp. 512–527; Szoka et al., *Proc. Natl. Acad. Sci. USA* (1978) 75:4194–4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.*(1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochem. Biophys. Acta*. (1975) 394:483–491. See, also, U.S. Pat. Nos. 4,663,161 and 4,871,488.

A number of viral based systems have been developed for gene transfer into mammalian cells. For example, retroviruses provide a convenient platform for gene delivery systems, such as murine sarcoma virus, mouse mammary tumor virus, Moloney murine leukemia virus, and Rous sarcoma virus. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980–990; Miller, A. D., *Human Gene Therapy* (1990) 1:5–14; Scarpa et al., *Virology* (1991) 180:849–852; Burns et al., *Proc. Natl. Acad. Sci. USA* (1993) 90:8033–8037; and Boris-Lawrie and Temin, *Cur. Opin. Genet. Develop.* (1993) 3:102–109. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110–2209), or isolated from known sources using commonly available techniques.

A number of adenovirus vectors have also been described, such as adenovirus Type 2 and Type 5 vectors. Unlike retroviruses which integrate into the host genome, adenoviruses persist extrachromosomally thus minimizing the risks associated with insertional mutagenesis (Haj-Ahmad and Graham, *J. Virol.* (1986) 57:267–274; Bett et al., *J. Virol.* (1993) 67:5911–5921; Mittereder et al., *Human Gene Therapy* (1994) 5:717–729; Seth et al., *J. Virol.* (1994) 68:933–940; Barr et al., *Gene Therapy* (1994) 1:51–58; Berkner, K. L. *BioTechniques* (1988) 6:616–629; and Rich et al., *Human Gene Therapy* (1993) 4:461–476).

Molecular conjugate vectors, such as the adenovirus chimeric vectors described in Michael et al., *J. Biol. Chem.* (1993) 268:6866–6869 and Wagner et al., *Proc. Natl. Acad. Sci. USA* (1992) 89:6099–6103, can also be used for gene delivery.

Members of the Alphavirus genus, such as but not limited to vectors derived from the Sindbis and Semliki Forest viruses, VEE, will also find use as viral vectors for delivering the gene of interest. For a description of Sindbis-virus derived vectors useful for the practice of the instant methods, see, Dubensky et al., *J. Virol.* (1996) 70:508–519; and International Publication Nos. WO 95/07995 and WO 96/17072.

Other vectors can be used, including but not limited to simian virus 40, cytomegalovirus. Bacterial vectors, such as Salmonella ssp. *Yersinia enterocolitica*, Shigella spp., *Vibrio cholerae*, Mycobacterium strain BCG, and *Listeria monocytogenes* can be used. Minichromosomes such as MC and MC1, bacteriophages, cosmids (plasmids into which phage lambda cos sites have been inserted) and replicons (genetic elements that are capable of replication under their own control in a cell) can also be used.

The chimeric constructs may also be encapsulated, adsorbed to, or associated with, particulate carriers. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly (lactides) and poly(lactide-co-glycolides), known as PLG. See, e.g., Jeffery et al., *Pharm. Res.* (1993) 10:362–368; and McGee et al., *J. Microencap.* (1996).

A wide variety of other methods can be used to deliver the constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fulsion, liposomes, peptoid delivery, or microinjection. See, e.g., Sambrook et al., supra, for a discussion of techniques for transforming cells of interest; and Felgner, P. L., *Advanced Drug Delivery Reviews* (1990) 5:163–187, for a review of delivery systems useful for gene transfer. One particularly effective method of delivering DNA using electroporation is described in International Publication No. WO/0045823.

Additionally, biolistic delivery systems employing particulate carriers such as gold and tungsten, are useful for delivering the constructs of the present invention. The particles are coated with the construct to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

The chimeric constructs can be delivered either directly to the vertebrate subject or, alternatively, delivered ex vivo, to cells derived from the subject and the cells reimplanted in the subject. For example, the constructs can be delivered as plasmid DNA, e.g., contained within a plasmid, such as pBR322, pUC, or ColE1.

An immunogenic composition of the invention is administered in a manner compatible with the particular composition used and in an amount which is effective to elicit an anti-HCV polypeptide antibody titer, such as an anti-E2 or anti-E1 antibody titer. Administration can be by any means known in the art, including intramuscular, intradermal, intraperitoneal, or subcutaneous injection, including injection using a biological ballistic gun ("gene gun"). Electroporation or iontophoresis can also be used. Administration may also be intranasal or oral. For oral administration of an immunogenic composition, a protein carrier is preferably included. An immunogenic composition, including compositions comprising naked DNA or RNA, is preferably injected intramuscularly to a large mammal, such as a baboon, chimpanzee, or human, at a dose of 0.5, 0.75, 1.0, 1.5, 2.0, 2.5, 5 or 10 mg/kg. A composition comprising virus-like particles is preferably injected intramuscularly to a large mammal, such as a human, at a dose of 0.01, 0.05, 0.5, 0.75, 1.0, 1.5, 2.0, 2.5, 5 or 10 mg protein/kg body weight.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral, intranasal, and pulmonary administration, suppositories, and transdermal or transcutaneous applications (e.g., see WO98/20734), needles, and gene guns or hyposprays. Dosage treatment may be a single dose schedule or a multiple dose schedule. The composition may be administered in conjunction with other immunoregulatory agents.

Methods for the ex vivo delivery and reimplantation of transformed cells into a subject are known in the art and described in e.g., WO93/14778. Examples of cells useful in ex vivo applications include, for example, stem cells, particularly hematopoetic, lymph cells, macrophages, dendritic cells, or tumor cells. Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Immunogenic compositions comprising either HBV/HCV virus-like particles or nucleic acids encoding and expressing such virus-like particles can be administered either to a mammal that is not infected with HCV or can be administered to an HCV-infected mammal. The particular dosages of virus-like particles or nucleic acids will depend on a number of factors including, but not limited to, the species, age, and general condition of the mammal to which the composition is administered and the mode of administration of the composition. An effective amount of the composition of the invention can be readily determined using routine experimentation. In vivo models are well known and can be employed to identify appropriate doses. If desired, co-stimulatory molecules or adjuvants can also be provided before, after, or together with the immunogenic compositions. Immunogenic compositions can be administered more than once, as required for effective immunization. Administration of immunogenic compositions containing virus-like particles can be performed either before or after administration of immunogenic compositions containing nucleic acids, such that one form (protein or nucleic acid) provides a primary immunization and the other form boosts the immune response.

III. Experimental

Below are examples of specific embodiments for carrying out the present invention. The examples are offered for illustrative purposes only, and are not intended to limit the scope of the present invention in any way. Those of skill in the art will readily appreciate that the invention may be practiced in a variety of ways given the teaching of this disclosure.

Efforts have been made to ensure accuracy with respect to numbers used (e.g., amounts, temperatures, etc.), but some experimental error and deviation should, of course, be allowed for.

EXAMPLE 1

Figure 5:
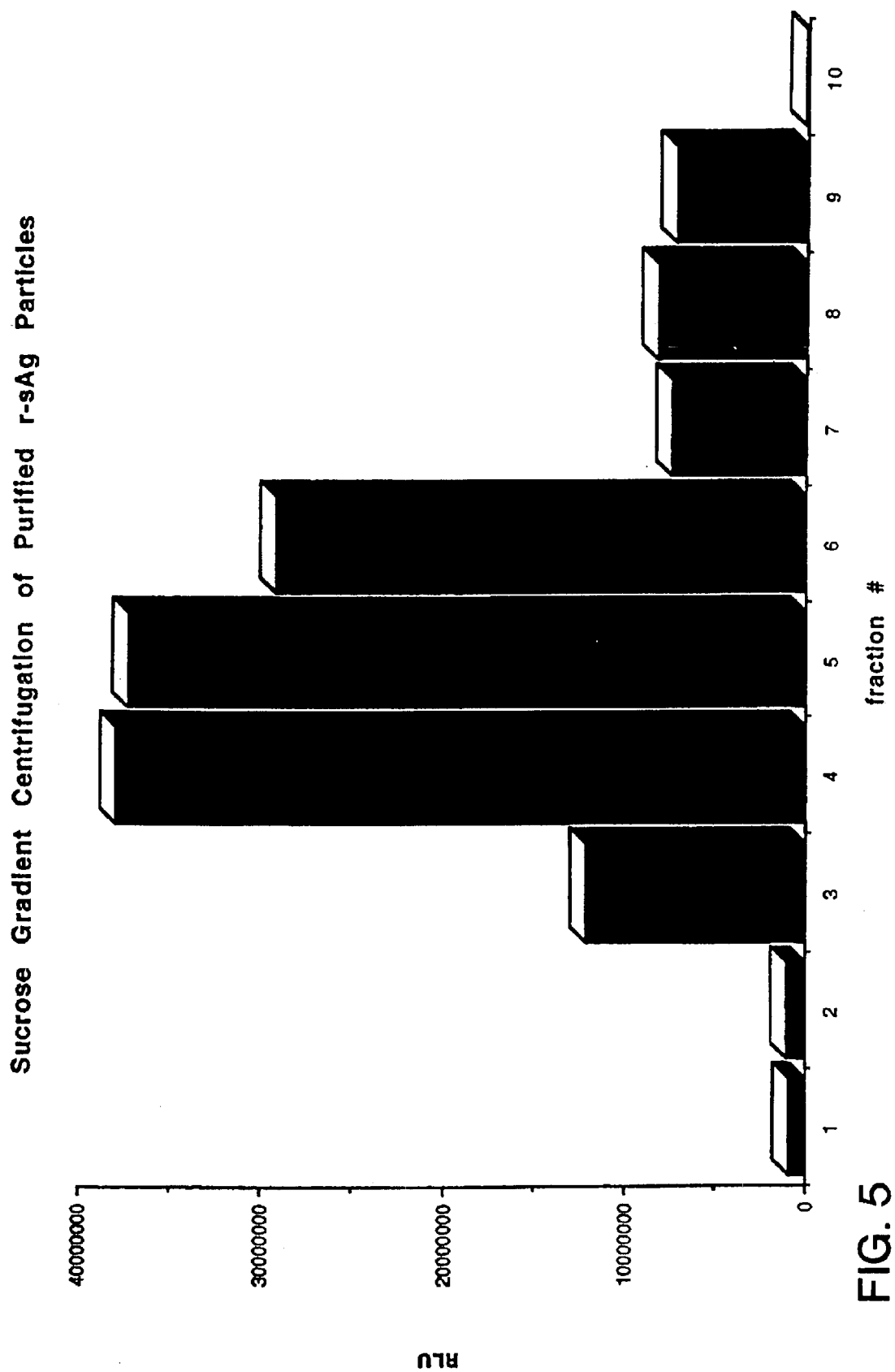
FIG. 5 shows the results of sucrose density gradient centrifugation of purified recombinant HBsAg virus-like particles. The experiment is described in Example 1.

Detection of HBV Virus-like Particles Using Sucrose Density Gradient Sedimentation Purified recombinant HBsAg particles were obtained in the form of a hepatitis B vaccine from Chiron Corp. Clinical Department. Two hundred fifty $\mu$L of a 37 $\mu$g/mL suspension in 0.03 M citrate, 0.26 M NaCl, 0.005% polysorbate 80 was loaded onto a 5–30% (wt-vol) sucrose gradient and centrifuged 4 hrs at 40,000 rpm in a Beckman SW41 rotor. Ten fractions were removed and assayed for HBsAg by the Magic Lite Assay. The results are shown in FIG. 5.

Magic Lite Assay

This describes a highly sensitive immunochemiluminescence assay used to detect HBV and HCV antigens. One hundred µL of sample was added to a 12×75 mm polystyrene tube. One hundred µL (30 µg) of a "capture" antibody was added to the sample. The capture antibody was covalently linked to paramagnetic particles by glutaraldehyde crosslinking a mixture of 6:1 paramagnetic particles:antibody. The tubes were vortexed and incubated in a 37° C. waterbath for 20 minutes. Next the tubes were placed on a magnetic rack where the paramagnetic particles (PMP) can aggregate. This allowed for washing and decanting. After the third wash, 100 µL of a "detecting" antibody, which was covalently linked to dimethylacridinium, was added and the tube was vortexed. The tubes were again incubated at 37° C. for 20 minutes and then placed on a magnetic rack for washing and decanting. After the third wash, the tubes were placed in a Ciba Corning Magic Lite chemiluminometer to measure the analyte bound. Results were expressed in arbitrary units of light intensity (relative light units, RLU).
Antibodies Anti-sAg was provided by Chiron Diagnostics (Walpole, Mass.) and was directed against serotypes AYW and ADW. MAb 5E5/H7 was obtained from mice using HeLa E1/E2 amino acids 1–967 as an immunogen and recognizes the E2 epitope 384–655. MAb 3D5/C3 was also obtained from mice immunized with HeLa El/E2 amino acids 1–967 and recognizes E1 epitope 211–217.

EXAMPLE 2

Figure 6A:
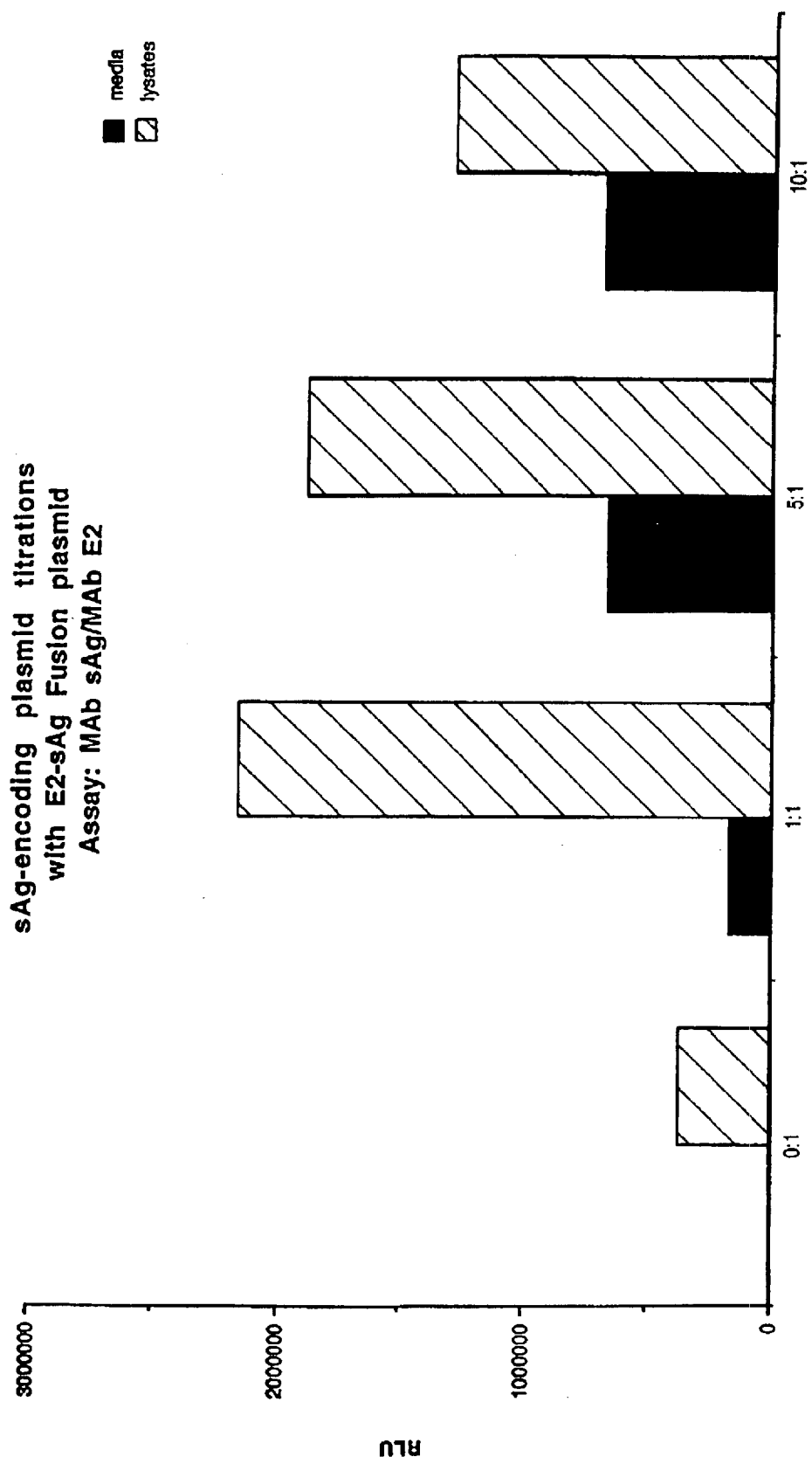
FIGS. 6A and 6B illustrate the expression of HCVE2-HBsAg fusion protein in COS7 cells. Increasing amounts of sAg-encoding plasmid were expressed together with HCVE2-sAg fusion plasmid. The experiment is described in Example 2. The capture antibody was MAb sAg, and the which are within the skill of the art. Such techniques are explained fully in the literature e.g., Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Animal Cell Culture* (R. I. Freshney ed. 1986); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London).
Figure 6B:
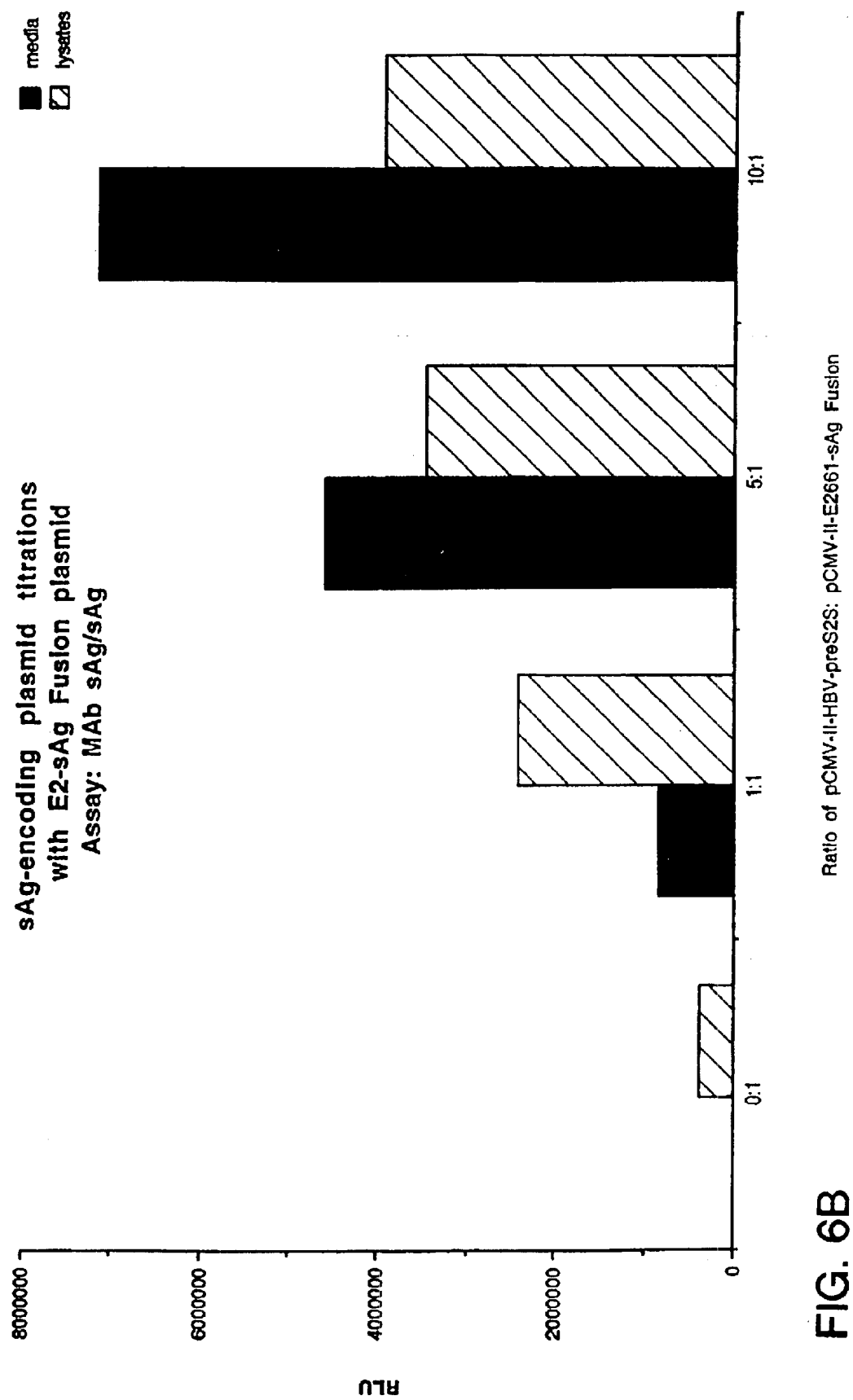

Expression of HBV/HCV Virus-like Particles Containing Chimeric HBsAg-E2-661 Antigen in COS7 Cells Five µg of pCMV-II-E2661-sAg (FIG. 4A) and increasing amounts of pCMV-II-pS2-sAg (FIG. 2A) were prepared. Expression from pCMV-II-pS2-sAg resulted in a mixture of about 5–20% preS2-S-polypeptide, with the remainder being S-polypeptide. Ratios of sAg to E2661-sAg plasmids used were 0:1, 1:1, 5:1, and 10:1 on a µg DNA basis. The total amount of DNA in each tube was normalized to 55 µg by the addition of pCMV-km-Bgal. This mixture was transfected into COS7 cells using the LT1 transfection reagent from Panvera, as described below. At 48 hours post-transfection, media and soluble lysates (obtained by incubating cell monolayers in PBS with 0.1% NP40 and centrifuging to remove insoluble debris) were removed and assayed by the Magic Lite Assay, with capture by anti-sAg followed by detection with a conjugated anti-E2 MAb (5E5/H7, see Example 1) (FIG. 6A) or MAb sAg (FIG. 6B). Both E2 and sAg were increasingly secreted into the medium as the ratio of sAg:E2661-sAg was increased, with an optimum secretion at ratios in the range of 5:1 to 10:1.

Figure 7A:
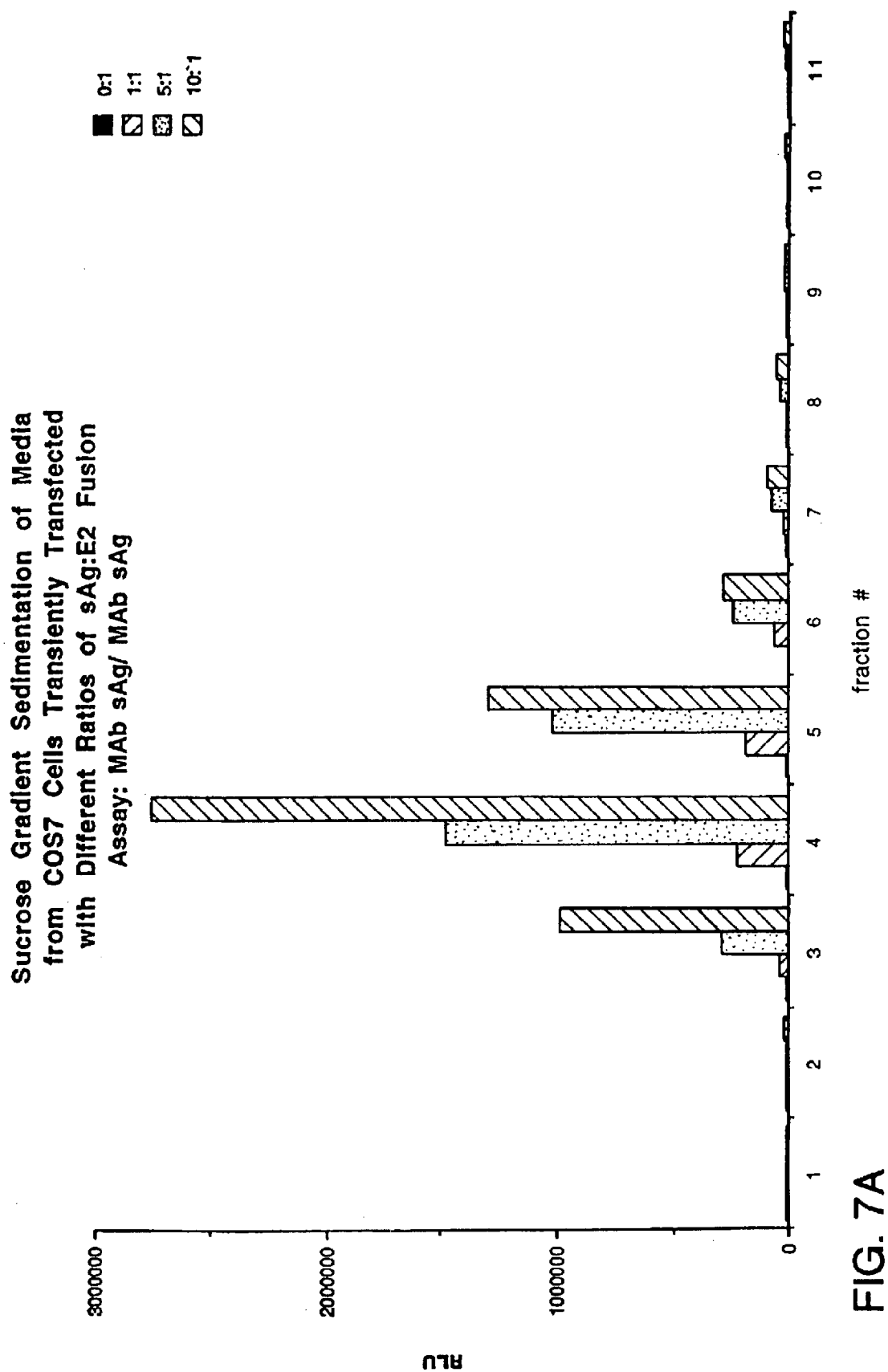
Figure 7B:
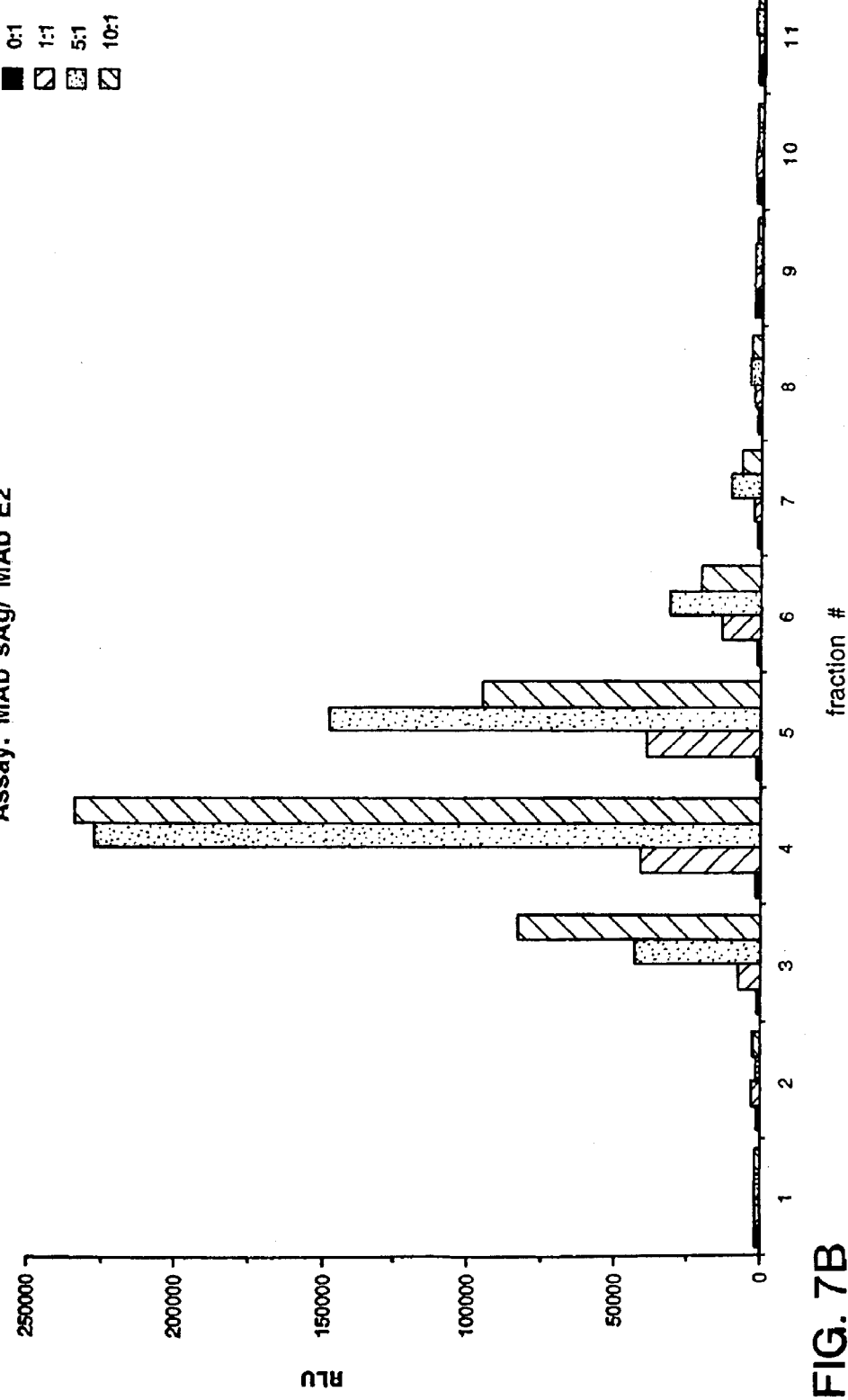

In order to characterize the virus-like particles, 1 mL of culture medium from each condition was loaded onto a 5–30% sucrose gradient. The samples were centrifuged 4 hrs at 40,000 rpm using a Beckman SW41 rotor. Eleven fractions were removed and assayed for E2 (FIG. 7A) or sAg (FIG. 7B) by the Magic Lite Assay. Both E2 and sAg were observed in highest amount in fraction 4, which is the same gradient position for the peak distribution of HBsAg-containing virus-like particles (FIG. 5).
Transfection Protocol Cells were seeded in 6-well plates the day prior to transfection so as to achieve 50–60% confluency at the time of transfection. Opti-mem (100 µL) and LT-1 transfection reagent (12 µL) were added to a sterile polypropylene tube and incubated at room temperature for five minutes. Three pg of DNA was then added to the tube, which was incubated another five minutes at room temperature. During this incubation period, the cells were washed with Opti-mem (2 mLs per well). Two mLs Opti-mem were added to each well, followed by 100 µL of the Opti-mem/LT-1/DNA mixture. The cells were then incubated for four hours at 37° C., followed by aspiration and addition of culture medium (1.5 mL/well of DMEM+10% FBS). At 48 hours post transfection, the medium was harvested and the cell monolayers were solubilized using PBS containing 0.1% NP-40. Both the harvested medium and the solubilized cells were centrifuged to remove debris.

EXAMPLE 3

Figure 8B:
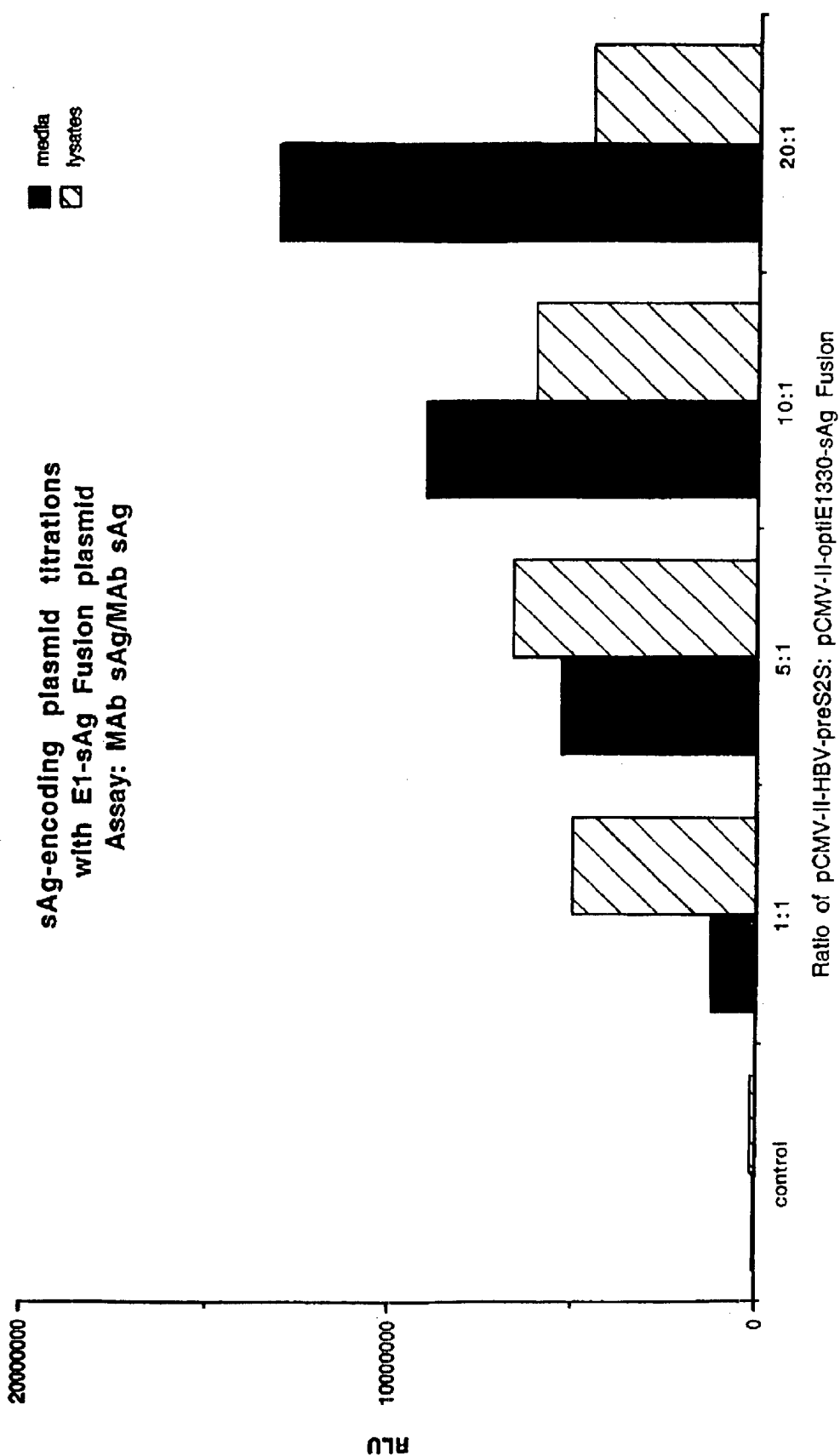

Expression of HBV/HCV Virus-like Particles Containing Chimeric HBsAg-E1-330 Antigen in COS7 Cells Mixtures ofpCMV-II-optiE1330-sAg (2.5 µg DNA) and various amounts of pCMV-II-pS2-sAg were prepared to provide ratios of sAg plasmid to E1-sAg plasmid of 0:1 (control); 1:1, 5:1, 10:1, and 20:1. Expression from pCMV-II-pS2-sAg resulted in a mixture of about 5–20% preS2-S-polypeptide, with the remainder being S-polypeptide. The total amount of DNA in each tube was normalized to 52.5 µg by the addition of pCMV-km-βgal. The mixtures were transfected into COS7 cells using the LT1 transfection reagent from Panvera. At 48 hours post-transfection, the media and soluble lysates were recovered and assayed by the Magic Lite Assay. Capture was with anti-sAg followed by detection with a conjugated anti-E1 MAb (eD5/C3) (FIG. 8A) or MAb sAg (FIG. 8B). Both E1 and sAg were increasingly secreted into the medium as the ratio of sAg:E2661-sAg was increased, with an optimum secretion at ratios in the range of 5:1 to 20:1.

Figure 9A:
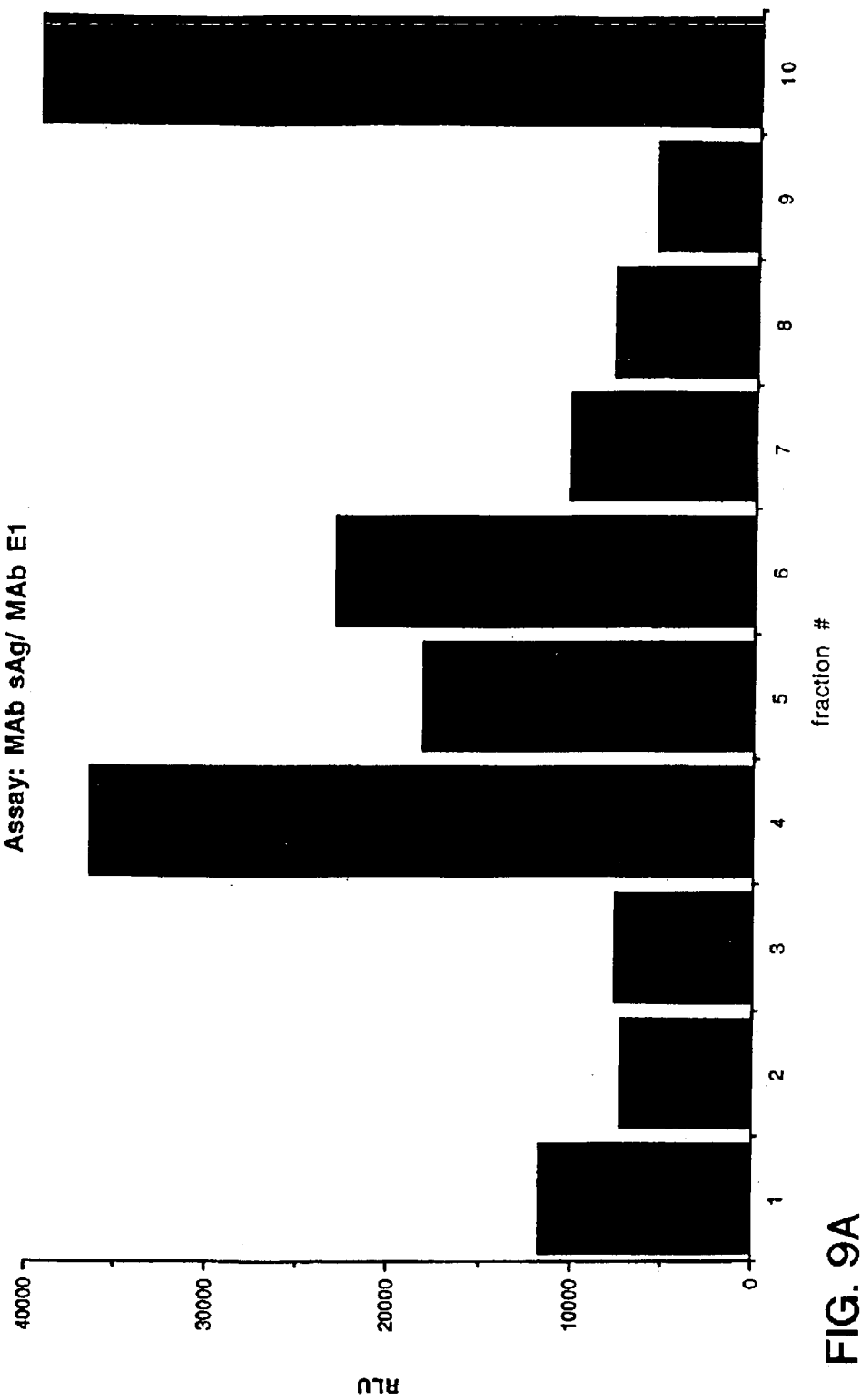

In order to characterize the virus-like particles, 1 mL of culture medium from each condition was loaded onto a 5–30% sucrose gradient. The samples were centrifuged 4 hrs at 40,000 rpm using a Beckman SW41 rotor. Eleven fractions were removed and assayed for E1 (FIG. 9A) or sAg (FIG. 9B) by the Magic Lite Assay. Both E1 and sAg were observed in highest amount in fractions 4–6, which is similar to the gradient position for the peak distribution of HBsAg-containing virus-like particles (FIG. 5).

EXAMPLE 4

Figure 10B:
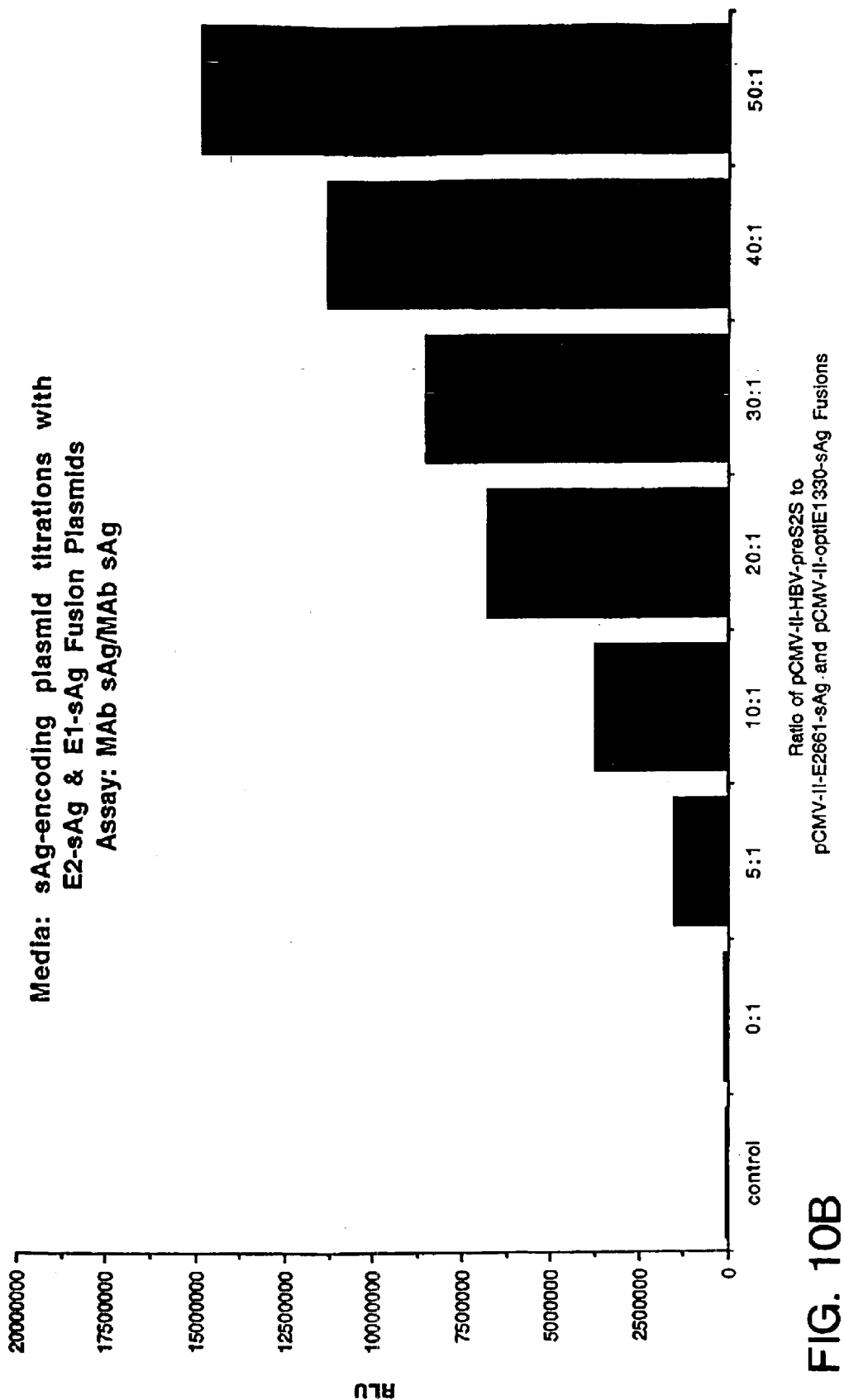

Expression of HBV/HCV Virus-like Particles Containing Both HBsAg-E2-661 and HBsAg-E1-330 Chimeric Antigens in COS7 Cells A mixture of pCMVII opti 330 E1-sAg and pCMV-II-E2661-sAg (0.5 µg DNA of each plasmid) was combined with increasing amounts of pCMV-11-pS2-sAg. The total amount of DNA in each tube was normalized to 26 µg by the addition of pCMV-kM-βgal. The mixture was transfected into COS7 cells using the LT1 transfection reagent from Panvera. At 48 hours post-transfection, media and soluble lysates were recovered and assayed by the Magic Lite Assay, with capture by anti-sAg followed by detection with a conjugated anti-E2 or anti-E1 MAb (FIG. 10A) or a conjugated anti-sAg (FIG. 10B).

EXAMPLE 5

Use of HBV/HCV Virus-like Particles to Generate an Immune Response

In order to test the ability of the subject HBV/HCV virus-like particles to generate an immune response in vivo, the following experiment was done. Four groups of 10 mice (Group 2 had 9 mice) were administered either DNA encoding HCV E2661 and pCMV-II, at a ratio of 5 times pCMV-II to E2661 (Group 1); pCMV-II-E2661-sAg (FIG. 4A) and pCMV-II, at a ratio of 5 times pCMV-II to pCMV-II-E2661-sAg (Group 2); pCMV-II-E2661-sAg and pCMV-II-pS2-sAg (FIG. 2A) at a ratio of 5 times pCMV-II-pS2-sAg to pCMV-II-E2661-sAg (Group 3); and pCMV-II and pCMV-II-pS2-sAg, at a ratio of 5 times pCMV-II-pS2-sAg to pCMV-II (Group 4).

All were immunized twice with 90 µg (45 µg/leg) per immunization, at day 0 and day 21, and blood was collected. Antibody titers were assessed by ELISA using a truncated E2 molecule, $E2_{715}$, which had been expressed in CHO cells, using the Magic Lite Assay described above. Results are shown in Table 1.

| Group # | Treatment | GM +/− SE |
|---|---|---|
| 1 | E2661 + 5x vector | 1300 +/− 85 |
| 2 | E2661-sAg + 5x vector | 1547 +/− 690 |
| 3 | E2661-sAg + 5x pS2sAg | 4175 +/− 603 |
| 4 | Vector + 5x pS2sAg | 0 |

A second experiment was run, again using 10 animals per group, except Group 5, which had 5 mice. The groups and results are shown in Table 2. Treatment protocol and antibody determination was as described above.

| Group # | Treatment | GM +/− SE |
|---|---|---|
| 1 | E2661 + 5x vector | 724 +/− 96 |
| 2 | E2661 + 5x pS2sAg | 222 +/− 90 |
| 3 | E2661-sAg+ 5x vector | 1018 +/− 305 |
| 4 | E2661-sAg + 5x pS2sAg | 1290 +/− 292 |
| 5 | mock | 0 |

As can be seen, titers to E2 in the $E2_{661}$-immunized mice were reduced in the presence of 5× sAg. This might have resulted from competition for docking to the endoplasmic reticulum. The E2 titers were higher when the E2 was fused to sAg. The addition of sAg in place of vector resulted in little change in titer. While this difference is small, comparison to the control with sAg is warranted. Since excess sAg caused a reduction in E2 titers in the unfused antigen, in the context of the fusion there was an apparent compensation. This presumably reflects the ability of sAg to promote secretion of the fusion.

Thus, chimeric HCV/HBV virus-like particles, as well as methods of making and using the same are disclosed. From the foregoing, it will be appreciated that, although specific embodiments of the invention have been described herein for purposes of illustration, various modifications may be made without deviating from the spirit and scope of the appended claims.

We claim:

1. A virus-like particle comprising a first hepatitis B virus surface antigen (HBsAg) and a chimeric antigen, wherein the chimeric antigen comprises a second HBsAg which is covalently linked to an HCV immunogenic polypeptide comprising at least 50 amino acids, and wherein the first and the second HBsAg each comprise a substantially complete S domain.

2. The virus-like particle of claim 1, wherein the first HBsAg consists of preS2 and S domains.

3. The virus-like particle of claim 1, wherein the first HBsAg consists of preS1, preS2, and S domains.

4. The virus-like particle of claim 1, wherein the carboxy terminus of the HCV immunogenic polypeptide is linked to the amino terminus of the second HBsAg.

5. The virus-like particle of claim 1, wherein the first HBsAg is present in excess relative to the chimeric antigen.

6. The virus-like particle of claim 5, wherein the first HBsAg is present in an amount that is between 1 and 100 times the amount of the chimeric antigen.

7. The virus-like particle of claim 1, wherein the HCV immunogenic polypeptide comprises an HCV E1 glycoprotein, a fragment of an HCV E1 glycoprotein, an HCV E2 glycoprotein, or a fragment of an HCV E2 glycoprotein.

8. The virus-like particle of claim 1, wherein the HCV immunogenic polypeptide consists of an HCV E1 glycoprotein, a fragment of an HCV E1 glycoprotein, an HCV E2 glycoprotein, or a fragment of an HCV E2 glycoprotein.

9. The virus-like particle of claim 7, wherein the HCV immunogenic polypeptide comprises (a) amino acid residues 192 to 330 of an HCV-1 polyprotein; or (b) the corresponding residues of other HCV isolates; or (c) an immunogenic sequence that elicits an immunological response against HCV, wherein the immunogenic sequence has at least 80% sequence identity to (a) or (b).

10. The virus-like particle of claim 7, wherein the HCV immunogenic polypeptide comprises (a) amino acid residues 384 to 661 of an HCV-1 polyprotein; or (b) the corresponding residues of other HCV isolates; or (c) an immunogenic sequence that elicits an immunological response against HCV, wherein the immunogenic sequence has at least 80% sequence identity to (a) or (b).

11. The virus-like particle of claim 10, wherein the HCV immunogenic polypeptide consists of amino acid residues 384 to 661 of an HCV polyprotein.

12. The virus-like particle of claim 1, wherein the HCV immunogenic polypeptide comprises (1) an HCV E1 glycoprotein or a fragment thereof and (2) an HCV E2 glycoprotein or a fragment thereof.

13. An immunogenic composition comprising:
a virus-like particle comprising a first HBsAg and a chimeric antigen, wherein the chimeric antigen comprises a second HBsAg which is linked to an HCV immunogenic polypeptide comprising at least 50 amino acids, and wherein the first and the second HBsAg each comprise a substantially complete S domain; and
a pharmaceutically acceptable carrier.

14. The immunogenic composition of claim 13, wherein the first HBsAg is present in excess compared to the chimeric antigen.

15. The immunogenic composition of claim 14, wherein the first HBsAg is present in an amount that is between 1 and 100 times the amount of the chimeric antigen.

16. The immunogenic composition of claim 13, wherein the HCV immunogenic polypeptide comprises an HCV E1 glycoprotein, a fragment of an HCV E1 glycoprotein, an HCV E2 glycoprotein, or a fragment of an HCV E2 glycoprotein.

17. The immunogenic composition of claim 13, wherein the HCV immunogenic polypeptide comprises (a) amino acid residues 192 to 330 of an HCV-1 polyprotein; or (b) the corresponding residues of other HCV isolates; or (c) an immunogenic sequence that elicits an immunological response against HCV, wherein the immunogenic sequence has at least 80% sequence identity to (a) or (b).

18. The immunogenic composition of claim 13, wherein the HCV immunogenic polypeptide consists of amino acid residues 192 to 330 of an HCV-1 polyprotein; or (b) the corresponding residues of other HCV isolates.

19. The immunogenic composition of claim 13, wherein the HCV immunogenic polypeptide comprises (a) amino acid residues 384 to 661 of an HCV-1 polyprotein; or (b) the corresponding residues of other HCV isolates; or (c) an immunogenic sequence that elicits an immunological response against HCV, wherein the immunogenic sequence has at least 80% sequence identity to (a) or (b).

20. The immunogenic composition of claim 13, wherein the HCV immunogenic polypeptide comprises (a) amino acid residues 384 to 661 of an HCV-1 polyprotein; or (b) the corresponding residues of other HCV isolates.

* * * * *

SEQUENCE LISTING

<160> NUMBER OF SEQ ID NOS: 7

<210> SEQ ID NO 1
<211> LENGTH: 4276
<212> TYPE: DNA
<213> ORGANISM: Artificial Sequence
<220> FEATURE:
<223> OTHER INFORMATION: Description of Artificial Sequence: plasmid
      pCMVII

<400> SEQUENCE: 1

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgaa gcttttttgca aaagcctagg cctccaaaaa agcctcctca ctacttctgg     240
aatagctcag aggccgaggc ggcctcggcc tctgcataaa taaaaaaaat tagtcagcca     300 tggggcgag aatgggcgga actgggcggg gagggaatta ttggctattg gccattgcat     360
acgttgtatc tatatcataa tatgtacatt tatattggct catgtccaat atgaccgcca     420
tgttgacatt gattattgac tagttattaa tagtaatcaa ttacggggtc attagttcat     480
agcccatata tggagttccg cgttacataa cttacggtaa atggcccgcc tggctgaccg     540
cccaacgacc cccgcccatt gacgtcaata atgacgtatg ttcccatagt aacgccaata     600
gggactttcc attgacgtca atgggtggag tatttacggt aaactgccca cttggcagta     660
catcaagtgt atcatatgcc aagtccgccc cctattgacg tcaatgacgg taaatggccc     720
gcctggcatt atgcccagta catgacctta cgggactttc ctacttggca gtacatctac     780
gtattagtca tcgctattac catggtgatg cggttttggc agtacaccaa tgggcgtgga     840
```

-continued

```
tagcggtttg actcacgggg atttccaagt ctccacccca ttgacgtcaa tgggagtttg      900
ttttggcacc aaaatcaacg ggactttcca aaatgtcgta ataacccgc cccgttgacg       960
caaatgggcg gtaggcgtgt acggtgggag gtctatataa gcagagctcg tttagtgaac     1020
cgtcagatcg cctggagacg ccatccacgc tgttttgacc tccatagaag acaccgggac     1080
cgatccagcc tccgcggccg ggaacggtgc attggaacgc ggattccccg tgccaagagt     1140
gacgtaagta ccgcctatag actctatagg cacacccctt tggctcttat gcatgctata     1200
ctgtttttgg cttggggcct atacaccccc gctcctatg ctataggtga tggtatagct      1260
tagcctatag gtgtgggtta ttgaccatta ttgaccactc ccctattggt gacgatactt     1320
tccattacta atccataaca tggctctttg ccacaactat ctctattggc tatatgccaa     1380
tactctgtcc ttcagagact gacacggact ctgtatttt acaggatggg gtccatttat      1440
tatttacaaa ttcacatata caacaacgcc gtccccgtg cccgcagttt ttattaaaca      1500
tagcgtggga tctccgacat ctcgggtacg tgttccggac atgggctctt ctccggtagc     1560
ggcggagctt ccacatccga gccctggtcc catccgtcca gcggctcatg gtcgctcggc     1620
agctccttgc tcctaacagt ggaggccaga cttaggcaca gcacaatgcc caccaccacc     1680
agtgtgccgc acaaggccgt ggcggtaggg tatgtgtctg aaaatgagct cggagattgg     1740
gctcgcacct ggacgcagat ggaagactta aggcagcggc agaagaagat gcaggcagct     1800
gagttgttgt attctgataa gagtcagagg taactcccgt tgcggtgctg ttaacggtgg     1860
agggcagtgt agtctgagca gtactcgttg ctgccgcgcg cgccaccaga cataatagct     1920
gacagactaa cagactgttc cttccatgg gtcttttctg cagtcaccgt cgtcgaccta      1980
agaattcaga ctcgagcaag tctagaaagg cgcgccaaga tatcaaggat ccactacgcg     2040
ttagagctcg ctgatcagcc tcgactgtgc cttctagttg ccagccatct gttgtttgcc     2100
cctcccccgt gccttccttg accctggaag gtgccactcc cactgtcctt tcctaataaa     2160
atgaggaaat tgcatcgcat tgtctgagta ggtgtcattc tattctgggg ggtgggggtgg   2220
ggcaggacag caaggggag gattgggaag acaatagcag gcatgctggg gagctcttcc      2280
gcttcctcgc tcactgactc gctgcgctcg gtcgttcggc tgcggcgagc ggtatcagct     2340
cactcaaagg cggtaatacg gttatccaca gaatcagggg ataacgcagg aaagaacatg     2400
tgagcaaaag gccagcaaaa ggccaggaac cgtaaaaagg ccgcgttgct ggcgtttttc     2460
cataggctcc gcccccctga cgagcatcac aaaaatcgac gctcaagtca gaggtggcga    2520
aacccgacag gactataaag ataccaggcg tttccccctg gaagctccct cgtgcgctct     2580
cctgttccga ccctgccgct taccggatac ctgtccgcct ttctcccttc gggaagcgtg     2640
gcgctttctc aatgctcacg ctgtaggtat ctcagttcgg tgtaggtcgt tcgctccaag     2700
ctgggctgtg tgcacgaacc cccgttcag cccgaccgct gcgccttatc cggtaactat      2760
cgtcttgagt ccaacccggt aagacacgac ttatcgccac tggcagcagc cactggtaac    2820
aggattagca gagcgaggta tgtaggcggt gctacagagt tcttgaagtg gtggcctaac     2880
tacggctaca ctagaaggac agtatttggt atctgcgctc tgctgaagcc agttaccttc     2940
ggaaaaagag ttggtagctc ttgatccggc aaacaaacca ccgctggtag cggtggtttt    3000
tttgtttgca agcagcagat tacgcgcaga aaaaaggat ctcaagaaga tcctttgatc      3060
ttttctacgg ggtctgacgc tcagtggaac gaaaactcac gttaagggat tttggtcatg     3120
agattatcaa aaaggatctt cacctagatc cttttaaatt aaaaatgaag ttttaaatca     3180
```

```
atctaaagta tatatgagta aacttggtct gacagttacc aatgcttaat cagtgaggca    3240
cctatctcag cgatctgtct atttcgttca tccatagttg cctgactccc cgtcgtgtag    3300
ataactacga tacgggaggg cttaccatct ggccccagtg ctgcaatgat accgcgagac    3360
ccacgctcac cggctccaga tttatcagca ataaaccagc cagccggaag ggccgagcgc    3420
agaagtggtc ctgcaacttt atccgcctcc atccagtcta ttaattgttg ccgggaagct    3480
agagtaagta gttcgccagt taatagtttg cgcaacgttg ttgccattgc tacaggcatc    3540
gtggtgtcac gctcgtcgtt tggtatggct tcattcagct ccggttccca acgatcaagg    3600
cgagttacat gatcccccat gttgtgcaaa aaagcggtta gctccttcgg tcctccgatc    3660
gttgtcagaa gtaagttggc cgcagtgtta tcactcatgg ttatggcagc actgcataat    3720
tctcttactg tcatgccatc cgtaagatgc ttttctgtga ctggtgagta ctcaaccaag    3780
tcattctgag aatagtgtat gcggcgaccg agttgctctt gcccggcgtc aatacgggat    3840
aataccgcgc cacatagcag aactttaaaa gtgctcatca ttggaaaacg ttcttcgggg    3900
cgaaaactct caaggatctt accgctgttg agatccagtt cgatgtaacc cactcgtgca    3960
cccaactgat cttcagcatc ttttactttc accagcgttt ctgggtgagc aaaaacagga    4020
aggcaaaatg ccgcaaaaaa gggaataagg gcgacacgga aatgttgaat actcatactc    4080
ttcctttttc aatattattg aagcatttat cagggttatt gtctcatgag cggatacata    4140
tttgaatgta tttagaaaaa taaacaaata ggggttccgc gcacatttcc ccgaaaagtg    4200
ccacctgacg tctaagaaac cattattatc atgacattaa cctataaaaa taggcgtatc    4260
acgaggccct ttcgtc                                                    4276
```

<210> SEQ ID NO 2
<211> LENGTH: 5128
<212> TYPE: DNA
<213> ORGANISM: Artificial Sequence
<220> FEATURE:
<223> OTHER INFORMATION: Description of Artificial Sequence: plasmid
      pCMVII-pS2-SAg
<221> NAME/KEY: CDS
<222> LOCATION: (1988)..(2830)

<400> SEQUENCE: 2

```
tcgcgcgttt cggtgatgac ggtgaaaacc tctgacacat gcagctcccg gagacggtca      60
cagcttgtct gtaagcggat gccgggagca gacaagcccg tcaggcgcgc tcagcgggtg     120
ttggcgggtg tcgggctgg cttaactatg cggcatcaga gcagattgta ctgagagtgc     180
accatatgaa gcttttgca aaagcctagg cctccaaaaa agcctcctca ctacttctgg     240
aatagctcag aggccgaggc ggcctcggcc tctgcataaa taaaaaaaat tagtcagcca     300
tggggcggag aatgggcgga actgggcggg agggaatta ttggctattg gccattgcat     360
acgttgtatc tatatcataa tatgtacatt tatattggct catgtccaat atgaccgcca     420
tgttgacatt gattattgac tagttattaa tagtaatcaa ttacggggtc attagttcat     480
agcccatata tggagttccg cgttacataa cttacggtaa atggcccgcc tggctgaccg     540
cccaacgacc cccgcccatt gacgtcaata atgacgtatg ttcccatagt aacgccaata     600
gggactttcc attgacgtca atgggtggag tatttacggt aaactgccca cttggcagta     660
catcaagtgt atcatatgcc aagtccgccc cctattgacg tcaatgacgg taaatggccc     720
gcctggcatt atgcccagta catgacctta cgggactttc ctacttggca gtacatctac     780
gtattagtca tcgctattac catggtgatg cggttttggc agtacaccaa tgggcgtgga     840
```

-continued

```
tagcggtttg actcacgggg atttccaagt ctccacccca ttgacgtcaa tgggagtttg    900
ttttggcacc aaaatcaacg ggactttcca aaatgtcgta ataacccgc cccgttgacg    960 caaatgggcg gtaggcgtgt acggtgggag gtctatataa gcagagctcg tttagtgaac   1020
cgtcagatcg cctggagacg ccatccacgc tgttttgacc tccatagaag acaccgggac   1080
cgatccagcc tccgcggccg ggaacggtgc attggaacgc ggattccccg tgccaagagt   1140
gacgtaagta ccgcctatag actctatagg cacaccccct tggctcttat gcatgctata   1200 ctgttttttgg cttggggcct atacaccccc gctccttatg ctataggtga tggtatagct   1260
tagcctatag gtgtgggtta ttgaccatta ttgaccactc ccctattggt gacgatactt   1320
tccattacta atccataaca tggctctttg ccacaactat ctctattggc tatatgccaa   1380
tactctgtcc ttcagagact gacacggact ctgtattttt acaggatggg gtccatttat   1440
tatttacaaa ttcacatata caacaacgcc gtcccccgtg cccgcagttt ttattaaaca   1500
tagcgtggga tctccgacat ctcgggtacg tgttccggac atgggctctt ctccggtagc   1560
ggcggagctt ccacatccga gccctggtcc catccgtcca gcggctcatg gtcgctcggc   1620
agctccttgc tcctaacagt ggaggccaga cttaggcaca gcacaatgcc caccaccacc   1680
agtgtgccgc acaaggccgt ggcggtaggg tatgtgtctg aaaatgagct cggagattgg   1740
gctcgcacct ggacgcagat ggaagactta aggcagcggc agaagaagat gcaggcagct   1800
gagttgttgt attctgataa gagtcagagg taactcccgt tgcggtgctg ttaacggtgg   1860
agggcagtgt agtctgagca gtactcgttg ctgccgcgcg cgccaccaga cataatagct   1920
gacagactaa cagactgttc ctttccatgg gtcttttctg cagtcaccgt cgtcgaccta   1980 agaattc atg cag tgg aac tcc act gcc ttc cac caa act ctg cag gat    2029
        Met Gln Trp Asn Ser Thr Ala Phe His Gln Thr Leu Gln Asp
         1               5                   10 ccc aga gtc agg ggt ctg tat ctt cct gct ggt ggc tcc agt tca gga    2077
Pro Arg Val Arg Gly Leu Tyr Leu Pro Ala Gly Gly Ser Ser Ser Gly
 15                  20                  25                  30 aca gta aac cct gct ccg aat att gcc tct cac atc tcg tca atc tcc    2125
Thr Val Asn Pro Ala Pro Asn Ile Ala Ser His Ile Ser Ser Ile Ser
                 35                  40                  45 gcg agg act ggg gac cct gtg acg aac atg gag aac atc aca tca gga    2173
Ala Arg Thr Gly Asp Pro Val Thr Asn Met Glu Asn Ile Thr Ser Gly
             50                  55                  60 ttc cta gga ccc ctg ctc gtg tta cag gcg ggg ttt ttc ttg ttg aca    2221
Phe Leu Gly Pro Leu Leu Val Leu Gln Ala Gly Phe Phe Leu Leu Thr
         65                  70                  75 aga atc ctc aca ata ccg cag agt cta gac tcg tgg tgg act tct ctc    2269
Arg Ile Leu Thr Ile Pro Gln Ser Leu Asp Ser Trp Trp Thr Ser Leu
     80                  85                  90 aat ttt cta ggg gga tct ccc gtg tgt ctt ggc caa aat tcg cag tcc    2317
Asn Phe Leu Gly Gly Ser Pro Val Cys Leu Gly Gln Asn Ser Gln Ser
 95                 100                 105                 110 cca acc tcc aat cac tca cca acc tcc tgt cct cca att tgt cct ggt    2365
Pro Thr Ser Asn His Ser Pro Thr Ser Cys Pro Pro Ile Cys Pro Gly
                115                 120                 125 tat cgc tgg atg tgt ctg cgg cgt ttt atc ata ttc ctc ttc atc ctg    2413
Tyr Arg Trp Met Cys Leu Arg Arg Phe Ile Ile Phe Leu Phe Ile Leu
            130                 135                 140 ctg cta tgc ctc atc ttc tta ttg gtt ctt ctg gat tat caa ggt atg    2461
Leu Leu Cys Leu Ile Phe Leu Leu Val Leu Leu Asp Tyr Gln Gly Met
        145                 150                 155 ttg ccc gtt tgt cct cta att cca gga tca aca aca acc agt acg gga    2509
```

```
                    -continued

Leu Pro Val Cys Pro Leu Ile Pro Gly Ser Thr Thr Thr Ser Thr Gly
    160                 165                 170 cca tgc aaa acc tgc acg act cct gct caa ggc aac tct atg ttt ccc     2557
Pro Cys Lys Thr Cys Thr Thr Pro Ala Gln Gly Asn Ser Met Phe Pro
175                 180                 185                 190 tca tgt tgc tgt aca aaa cct acg gat gga aat tgc acc tgt att ccc     2605
Ser Cys Cys Cys Thr Lys Pro Thr Asp Gly Asn Cys Thr Cys Ile Pro
                195                 200                 205 atc cca tcg tcc tgg gct ttc gca aaa tac cta tgg gag tgg gcc tca     2653
Ile Pro Ser Ser Trp Ala Phe Ala Lys Tyr Leu Trp Glu Trp Ala Ser
            210                 215                 220 gtc cgt ttc tct tgg ctc agt tta cta gtg cca ttt gtt cag tgg ttc     2701
Val Arg Phe Ser Trp Leu Ser Leu Leu Val Pro Phe Val Gln Trp Phe
        225                 230                 235 gta ggg ctt tcc ccc act gtt tgg ctt tca gct ata tgg atg atg tgg     2749
Val Gly Leu Ser Pro Thr Val Trp Leu Ser Ala Ile Trp Met Met Trp
    240                 245                 250 tat tgg ggg cca agt ctg tac agc atc gtg agt ccc ttt ata ccg ctg     2797
Tyr Trp Gly Pro Ser Leu Tyr Ser Ile Val Ser Pro Phe Ile Pro Leu
255                 260                 265                 270 tta cca att ttc ttt tgt ctc tgg gta tac att taagaattca gactcgagca   2850
Leu Pro Ile Phe Phe Cys Leu Trp Val Tyr Ile
                275                 280 agtctagaaa ggcgcgccaa gatatcaagg atccactacg cgttagagct cgctgatcag   2910
cctcgactgt gccttctagt tgccagccat ctgttgtttg cccctccccc gtgccttcct   2970
tgaccctgga aggtgccact cccactgtcc tttcctaata aaatgaggaa attgcatcgc   3030
attgtctgag taggtgtcat tctattctgg ggggtggggt ggggcaggac agcaagggggg  3090 aggattggga agacaatagc aggcatgctg gggagctctt ccgcttcctc gctcactgac   3150
tcgctgcgct cggtcgttcg gctgcggcga gcggtatcag ctcactcaaa ggcggtaata   3210
cggttatcca cagaatcagg ggataacgca ggaaagaaca tgtgagcaaa aggccagcaa   3270
aaggccagga accgtaaaaa ggccgcgttg ctggcgtttt tccataggct ccgcccccct   3330
gacgagcatc acaaaaatcg acgctcaagt cagaggtggc gaaacccgac aggactataa   3390
agataccagg cgtttccccc tggaagctcc ctcgtgcgct ctcctgttcc gaccctgccg   3450
cttaccggat acctgtccgc ctttctccct tcgggaagcg tggcgctttc tcaatgctca   3510
cgctgtaggt atctcagttc ggtgtaggtc gttcgctcca agctgggctg tgtgcacgaa   3570
ccccccgttc agcccgaccg ctgcgcctta tccggtaact atcgtcttga gtccaacccg   3630
gtaagacacg acttatcgcc actggcagca gccactggta acaggattag cagagcgagg   3690
tatgtaggcg gtgctacaga gttcttgaag tggtggccta actacggcta cactagaagg   3750
acagtatttg gtatctgcgc tctgctgaag ccagttacct tcggaaaaag agttggtagc   3810
tcttgatccg gcaaacaaac caccgctggt agcggtggtt ttttttgtttg caagcagcag   3870 attacgcgca gaaaaaaagg atctcaagaa gatcctttga tcttttctac ggggtctgac   3930
gctcagtgga acgaaaactc acgttaaggg attttggtca tgagattatc aaaaaggatc   3990
ttcacctaga tccttttaaa ttaaaaatga agttttaaat caatctaaag tatatatgag   4050
taaacttggt ctgacagtta ccaatgctta atcagtgagg cacctatctc agcgatctgt   4110
ctatttcgtt catccatagt tgcctgactc cccgtcgtgt agataactac gatacgggag   4170
ggcttaccat ctggccccag tgctgcaatg ataccgcgag acccacgctc accggctcca   4230
gatttatcag caataaacca gccagccgga agggccgagc gcagaagtgg tcctgcaact   4290
```

-continued

```
ttatccgcct ccatccagtc tattaattgt tgccgggaag ctagagtaag tagttcgcca      4350
gttaatagtt tgcgcaacgt tgttgccatt gctacaggca tcgtggtgtc acgctcgtcg      4410
tttggtatgg cttcattcag ctccggttcc caacgatcaa ggcgagttac atgatccccc      4470
atgttgtgca aaaaagcggt tagctccttc ggtcctccga tcgttgtcag aagtaagttg      4530
gccgcagtgt tatcactcat ggttatggca gcactgcata attctcttac tgtcatgcca      4590
tccgtaagat gcttttctgt gactggtgag tactcaacca agtcattctg agaatagtgt      4650
atgcggcgac cgagttgctc ttgcccggcg tcaatacggg ataataccgc gccacatagc      4710
agaactttaa aagtgctcat cattggaaaa cgttcttcgg ggcgaaaact ctcaaggatc      4770
ttaccgctgt tgagatccag ttcgatgtaa cccactcgtg cacccaactg atcttcagca      4830
tcttttactt tcaccagcgt ttctgggtga gcaaaaacag gaaggcaaaa tgccgcaaaa      4890
aagggaataa gggcgacacg gaaatgttga atactcatac tcttcctttt tcaatattat      4950
tgaagcattt atcagggtta ttgtctcatg agcggataca tatttgaatg tatttagaaa      5010
aataaacaaa tagggttcc gcgcacattt ccccgaaaag tgccacctga cgtctaagaa      5070
accattatta tcatgacatt aacctataaa aataggcgta tcacgaggcc ctttcgtc        5128
```

<210> SEQ ID NO 3
<211> LENGTH: 281
<212> TYPE: PRT
<213> ORGANISM: Artificial Sequence
<220> FEATURE:
<223> OTHER INFORMATION: Description of Artificial Sequence: plasmid pCMVII-pS2-SAg

<400> SEQUENCE: 3

```
Met Gln Trp Asn Ser Thr Ala Phe His Gln Thr Leu Gln Asp Pro Arg
  1               5                  10                  15

Val Arg Gly Leu Tyr Leu Pro Ala Gly Gly Ser Ser Ser Gly Thr Val
                 20                  25                  30

Asn Pro Ala Pro Asn Ile Ala Ser His Ile Ser Ser Ile Ser Ala Arg
             35                  40                  45

Thr Gly Asp Pro Val Thr Asn Met Glu Asn Ile Thr Ser Gly Phe Leu
         50                  55                  60

Gly Pro Leu Leu Val Leu Gln Ala Gly Phe Phe Leu Leu Thr Arg Ile
 65                  70                  75                  80

Leu Thr Ile Pro Gln Ser Leu Asp Ser Trp Trp Thr Ser Leu Asn Phe
                 85                  90                  95

Leu Gly Gly Ser Pro Val Cys Leu Gly Gln Asn Ser Gln Ser Pro Thr
                100                 105                 110

Ser Asn His Ser Pro Thr Ser Cys Pro Pro Ile Cys Pro Gly Tyr Arg
            115                 120                 125

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Thr Thr Thr Ser Thr Gly Pro Cys
                165                 170                 175

Lys Thr Cys Thr Thr Pro Ala Gln Gly Asn Ser Met Phe Pro Ser Cys
            180                 185                 190

Cys Cys Thr Lys Pro Thr Asp Gly Asn Cys Thr Cys Ile Pro Ile Pro
        195                 200                 205

Ser Ser Trp Ala Phe Ala Lys Tyr Leu Trp Glu Trp Ala Ser Val Arg
```

-continued

```
            210                 215                 220
Phe Ser Trp Leu Ser Leu Leu Val Pro Phe Val Gln Trp Phe Val Gly
225                 230                 235                 240

Leu Ser Pro Thr Val Trp Leu Ser Ala Ile Trp Met Met Trp Tyr Trp
                245                 250                 255

Gly Pro Ser Leu Tyr Ser Ile Val Ser Pro Phe Ile Pro Leu Leu Pro
            260                 265                 270

Ile Phe Phe Cys Leu Trp Val Tyr Ile
        275                 280

<210> SEQ ID NO 4
<211> LENGTH: 5459
<212> TYPE: DNA
<213> ORGANISM: Artificial Sequence
<220> FEATURE:
<223> OTHER INFORMATION: Description of Artificial Sequence: pCMVII opti
      330 E1/SAg
<221> NAME/KEY: CDS
<222> LOCATION: (1992)..(3161)

<400> SEQUENCE: 4
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120 ttggcgggtg tcgggctgg cttaactatg cggcatcaga gcagattgta ctgagagtgc      180
accatatgaa gctttttgca aaagcctagg cctccaaaaa agcctcctca ctacttctgg      240
aatagctcag aggccgaggc ggcctcggcc tctgcataaa taaaaaaaat tagtcagcca      300
tggggcggag aatgggcgga actgggcggg gagggaatta ttggctattg gccattgcat      360
acgttgtatc tatatcataa tatgtacatt tatattggct catgtccaat atgaccgcca      420
tgttgacatt gattattgac tagttattaa tagtaatcaa ttacgggtc attagttcat      480 agcccatata tggagttccg cgttacataa cttacggtaa atggcccgcc tggctgaccg      540
cccaacgacc cccgcccatt gacgtcaata atgacgtatg ttcccatagt aacgccaata      600
gggactttcc attgacgtca atgggtggag tatttacggt aaactgccca cttggcagta      660
catcaagtgt atcatatgcc aagtccgccc cctattgacg tcaatgacgg taaatggccc      720
gcctggcatt atgcccagta catgacctta cgggactttc ctacttggca gtacatctac      780
gtattagtca tcgctattac catggtgatg cggttttggc agtacaccaa tgggcgtgga      840
tagcggtttg actcacgggg atttccaagt ctccacccca ttgacgtcaa tgggagtttg      900
ttttggcacc aaaatcaacg ggactttcca aatgtcgta ataaccccgc ccgttgacg      960 caaatgggcg gtaggcgtgt acggtgggag gtctatataa gcagagctcg tttagtgaac     1020
cgtcagatcg cctggagacg ccatccacgc tgttttgacc tccatagaag acaccgggac     1080
cgatccagcc tccgcggccg ggaacggtgc attggaacgc ggattccccg tgccaagagt     1140
gacgtaagta ccgcctatag actctatagg cacacccctt ggctcttat gcatgctata     1200 ctgttttggg cttggggcct atacaccccc gctccttatg ctataggtga tggtatagct     1260
tagcctatag gtgtgggtta ttgaccatta ttgaccactc ccctattggt gacgatactt     1320
tccattacta atccataaca tggctctttg ccacaactat ctctattggc tatatgccaa     1380
tactctgtcc ttcagagact gacacggact ctgtattttt acaggatggg gtccatttat     1440
tatttacaaa ttcacatata caacaacgcc gtccccgtg cccgcagttt ttattaaaca     1500
tagcgtggga tctccgacat ctcgggtacg tgttccggac atgggctctt ctccggtagc     1560
```

-continued

```
ggcggagctt ccacatccga gccctggtcc catccgtcca gcggctcatg gtcgctcggc     1620
agctccttgc tcctaacagt ggaggccaga cttaggcaca gcacaatgcc caccaccacc     1680
agtgtgccgc acaaggccgt ggcggtaggg tatgtgtctg aaaatgagct cggagattgg     1740
gctcgcacct ggacgcagat ggaagactta aggcagcggc agaagaagat gcaggcagct     1800
gagttgttgt attctgataa gagtcagagg taactcccgt tgcggtgctg ttaacggtgg     1860
agggcagtgt agtctgagca gtactcgttg ctgccgcgcg cgccaccaga cataatagct     1920
gacagactaa cagactgttc ctttccatgg gtcttttctg cagtcaccgt cgtcgacgaa     1980
ttcaagcaat c atg gat gca atg aag aga ggg ctc tgc tgt gtg ctg ctg     2030
            Met Asp Ala Met Lys Arg Gly Leu Cys Cys Val Leu Leu
              1               5                  10 ctg tgt gga gca gtc ttc gtt tcg ccc agc gct agc tac cag gtg cgc     2078
Leu Cys Gly Ala Val Phe Val Ser Pro Ser Ala Ser Tyr Gln Val Arg
 15                  20                  25 aac agc acc ggc ctg tac cac gtg acc aac gac tgc ccc aac agc agc     2126
Asn Ser Thr Gly Leu Tyr His Val Thr Asn Asp Cys Pro Asn Ser Ser
 30              35                  40                  45 atc gtg tac gag gcc gcc gac gcc atc ctg cac acc ccc ggc tgc gtg     2174
Ile Val Tyr Glu Ala Ala Asp Ala Ile Leu His Thr Pro Gly Cys Val
                 50                  55                  60 ccc tgc gtg cgc gag ggc aac gcc agc cgc tgc tgg gtg gcc atg acc     2222
Pro Cys Val Arg Glu Gly Asn Ala Ser Arg Cys Trp Val Ala Met Thr
             65                  70                  75 ccc acc gtg gcc acc cgc gac ggc aag ctg ccc gcc acc cag ctg cgc     2270
Pro Thr Val Ala Thr Arg Asp Gly Lys Leu Pro Ala Thr Gln Leu Arg
         80                  85                  90 cgc cac atc gac ctg ctg gtg ggc agc gcc acc ctg tgc agc gcc ctg     2318
Arg His Ile Asp Leu Leu Val Gly Ser Ala Thr Leu Cys Ser Ala Leu
     95                  100                 105 tac gtg ggc gac ctg tgc ggc agc gtg ttc ctg gtg ggc cag ctg ttc     2366
Tyr Val Gly Asp Leu Cys Gly Ser Val Phe Leu Val Gly Gln Leu Phe
110                 115                 120                 125 acc ttc agc ccc cgc cgc cac tgg acc acc cag ggc tgc aac tgc agc     2414
Thr Phe Ser Pro Arg Arg His Trp Thr Thr Gln Gly Cys Asn Cys Ser
                 130                 135                 140 atc tac ccc ggc cac atc acc ggc cac cgc atg gcc tgg gac atg atg     2462
Ile Tyr Pro Gly His Ile Thr Gly His Arg Met Ala Trp Asp Met Met
             145                 150                 155 atg aac tgg agc ccc acc acc atg gag aac atc aca tca gga ttc cta     2510
Met Asn Trp Ser Pro Thr Thr Met Glu Asn Ile Thr Ser Gly Phe Leu
         160                 165                 170 gga ccc ctg ctc gtg tta cag gcg ggg ttt ttc ttg ttg aca aga atc     2558
Gly Pro Leu Leu Val Leu Gln Ala Gly Phe Phe Leu Leu Thr Arg Ile
     175                 180                 185 ctc aca ata ccg cag agt cta gac tcg tgg tgg act tct ctc aat ttt     2606
Leu Thr Ile Pro Gln Ser Leu Asp Ser Trp Trp Thr Ser Leu Asn Phe
190                 195                 200                 205 cta ggg gga tct ccc gtg tgt ctt ggc caa aat tcg cag tcc cca acc     2654
Leu Gly Gly Ser Pro Val Cys Leu Gly Gln Asn Ser Gln Ser Pro Thr
                 210                 215                 220 tcc aat cac tca cca acc tcc tgt cct cca att tgt cct ggt tat cgc     2702
Ser Asn His Ser Pro Thr Ser Cys Pro Pro Ile Cys Pro Gly Tyr Arg
             225                 230                 235 tgg atg tgt ctg cgg cgt ttt atc ata ttc ctc ttc atc ctg ctg cta     2750
Trp Met Cys Leu Arg Arg Phe Ile Ile Phe Leu Phe Ile Leu Leu Leu
         240                 245                 250 tgc ctc atc ttc tta ttg gtt ctt ctg gat tat caa ggt atg ttg ccc     2798
```

-continued

```
                 Cys Leu Ile Phe Leu Leu Val Leu Leu Asp Tyr Gln Gly Met Leu Pro
                     255                 260                 265 gtt tgt cct cta att cca gga tca aca aca acc agt acg gga cca tgc        2846
Val Cys Pro Leu Ile Pro Gly Ser Thr Thr Thr Ser Thr Gly Pro Cys
270                 275                 280                 285 aaa acc tgc acg act cct gct caa ggc aac tct atg ttt ccc tca tgt        2894
Lys Thr Cys Thr Thr Pro Ala Gln Gly Asn Ser Met Phe Pro Ser Cys
                290                 295                 300 tgc tgt aca aaa cct acg gat gga aat tgc acc tgt att ccc atc cca        2942
Cys Cys Thr Lys Pro Thr Asp Gly Asn Cys Thr Cys Ile Pro Ile Pro
            305                 310                 315 tcg tcc tgg gct ttc gca aaa tac cta tgg gag tgg gcc tca gtc cgt        2990
Ser Ser Trp Ala Phe Ala Lys Tyr Leu Trp Glu Trp Ala Ser Val Arg
        320                 325                 330 ttc tct tgg ctc agt tta cta gtg cca ttt gtt cag tgg ttc gta ggg        3038
Phe Ser Trp Leu Ser Leu Leu Val Pro Phe Val Gln Trp Phe Val Gly
    335                 340                 345 ctt tcc ccc act gtt tgg ctt tca gct ata tgg atg atg tgg tat tgg        3086
Leu Ser Pro Thr Val Trp Leu Ser Ala Ile Trp Met Met Trp Tyr Trp
350                 355                 360                 365 ggg cca agt ctg tac agc atc gtg agt ccc ttt ata ccg ctg tta cca        3134
Gly Pro Ser Leu Tyr Ser Ile Val Ser Pro Phe Ile Pro Leu Leu Pro
                370                 375                 380 att ttc ttt tgt ctc tgg gta tac att taagaattca gactcgagca              3181
Ile Phe Phe Cys Leu Trp Val Tyr Ile
                385                 390 agtctagaaa ggcgcgccaa gatatcaagg atccactacg cgttagagct cgctgatcag      3241
cctcgactgt gccttctagt tgccagccat ctgttgtttg cccctccccc gtgccttcct      3301
tgaccctgga aggtgccact cccactgtcc tttcctaata aaatgaggaa attgcatcgc      3361
attgtctgag taggtgtcat tctattctgg ggggtgggt ggggcaggac agcaaggggg       3421
aggattggga agacaatagc aggcatgctg gggagctctt ccgcttcctc gctcactgac      3481
tcgctgcgct cggtcgttcg gctgcggcga gcggtatcag ctcactcaaa ggcggtaata     3541
cggttatcca cagaatcagg ggataacgca ggaaagaaca tgtgagcaaa aggccagcaa     3601
aaggccagga accgtaaaaa ggccgcgttg ctggcgtttt tccataggct ccgcccccct     3661
gacgagcatc acaaaaatcg acgctcaagt cagaggtggc gaaacccgac aggactataa    3721
agataccagg cgtttccccc tggaagctcc ctcgtgcgct ctcctgttcc gaccctgccg    3781
cttaccggat acctgtccgc ctttctccct tcgggaagcg tggcgctttc tcaatgctca    3841
cgctgtaggt atctcagttc ggtgtaggtc gttcgctcca agctgggctg tgtgcacgaa    3901
ccccccgttc agcccgaccg ctgcgcctta tccggtaact atcgtcttga gtccaacccg    3961
gtaagacacg acttatcgcc actggcagca gccactggta acaggattag cagagcgagg    4021
tatgtaggcg gtgctacaga gttcttgaag tggtggccta actacggcta cactagaagg    4081
acagtatttg gtatctgcgc tctgctgaag ccagttacct tcggaaaaag agttggtagc    4141
tcttgatccg gcaaacaaac caccgctggt agcggtggtt ttttgtttg caagcagcag     4201 attacgcgca gaaaaaaagg atctcaagaa gatcctttga tcttttctac ggggtctgac    4261
gctcagtgga acgaaaactc acgttaaggg attttggtca tgagattatc aaaaaggatc    4321
ttcacctaga tccttttaaa ttaaaaatga agttttaaat caatctaaag tatatatgag    4381
taaacttggt ctgacagtta ccaatgctta atcagtgagg cacctatctc agcgatctgt    4441
ctatttcgtt catccatagt tgcctgactc cccgtcgtgt agataactac gatacgggag    4501
```

-continued

```
ggcttaccat ctggccccag tgctgcaatg ataccgcgag acccacgctc accggctcca   4561
gatttatcag caataaacca gccagccgga agggccgagc gcagaagtgg tcctgcaact   4621
ttatccgcct ccatccagtc tattaattgt tgccgggaag ctagagtaag tagttcgcca   4681
gttaatagtt tgcgcaacgt tgttgccatt gctacaggca tcgtggtgtc acgctcgtcg   4741
tttggtatgg cttcattcag ctccggttcc caacgatcaa ggcgagttac atgatccccc   4801
atgttgtgca aaaaagcggt tagctccttc ggtcctccga tcgttgtcag aagtaagttg   4861
gccgcagtgt tatcactcat ggttatggca gcactgcata attctcttac tgtcatgcca   4921
tccgtaagat gcttttctgt gactggtgag tactcaacca agtcattctg agaatagtgt   4981
atgcggcgac cgagttgctc ttgcccggcg tcaatacggg ataataccgc gccacatagc   5041
agaactttaa aagtgctcat cattggaaaa cgttcttcgg ggcgaaaact ctcaaggatc   5101
ttaccgctgt tgagatccag ttcgatgtaa cccactcgtg cacccaactg atcttcagca   5161
tcttttactt tcaccagcgt ttctgggtga gcaaaaacag gaaggcaaaa tgccgcaaaa   5221
aagggaataa gggcgacacg gaaatgttga atactcatac tcttcctttt tcaatattat   5281
tgaagcattt atcagggtta ttgtctcatg agcggataca tatttgaatg tatttagaaa   5341
aataaacaaa taggggttcc gcgcacattt ccccgaaaag tgccacctga cgtctaagaa   5401
accattatta tcatgacatt aacctataaa aataggcgta tcacgaggcc ctttcgtc     5459
```

```

<210> SEQ ID NO 5
<211> LENGTH: 390
<212> TYPE: PRT
<213> ORGANISM: Artificial Sequence
<220> FEATURE:
<223> OTHER INFORMATION: Description of Artificial Sequence: pCMVII opti
      330 E1/SAg

<400> SEQUENCE: 5

Met Asp Ala Met Lys Arg Gly Leu Cys Cys Val Leu Leu Leu Cys Gly
  1               5                  10                  15

Ala Val Phe Val Ser Pro Ser Ala Ser Tyr Gln Val Arg Asn Ser Thr
             20                  25                  30

Gly Leu Tyr His Val Thr Asn Asp Cys Pro Asn Ser Ser Ile Val Tyr
         35                  40                  45

Glu Ala Ala Asp Ala Ile Leu His Thr Pro Gly Cys Val Pro Cys Val
     50                  55                  60

Arg Glu Gly Asn Ala Ser Arg Cys Trp Val Ala Met Thr Pro Thr Val
 65                  70                  75                  80

Ala Thr Arg Asp Gly Lys Leu Pro Ala Thr Gln Leu Arg Arg His Ile
                 85                  90                  95

Asp Leu Leu Val Gly Ser Ala Thr Leu Cys Ser Ala Leu Tyr Val Gly
            100                 105                 110

Asp Leu Cys Gly Ser Val Phe Leu Val Gly Gln Leu Phe Thr Phe Ser
        115                 120                 125

Pro Arg Arg His Trp Thr Thr Gln Gly Cys Asn Cys Ser Ile Tyr Pro
    130                 135                 140

Gly His Ile Thr Gly His Arg Met Ala Trp Asp Met Met Met Asn Trp
145                 150                 155                 160

Ser Pro Thr Thr Met Glu Asn Ile Thr Ser Gly Phe Leu Gly Pro Leu
                165                 170                 175

Leu Val Leu Gln Ala Gly Phe Phe Leu Leu Thr Arg Ile Leu Thr Ile
            180                 185                 190
```

-continued

```
Pro Gln Ser Leu Asp Ser Trp Trp Thr Ser Leu Asn Phe Leu Gly Gly
        195                 200                 205

Ser Pro Val Cys Leu Gly Gln Asn Ser Gln Ser Pro Thr Ser Asn His
    210                 215                 220

Ser Pro Thr Ser Cys Pro Pro Ile Cys Pro Gly Tyr Arg Trp Met Cys
225                 230                 235                 240

Leu Arg Arg Phe Ile Ile Phe Leu Phe Ile Leu Leu Leu Cys Leu Ile
                245                 250                 255

Phe Leu Leu Val Leu Leu Asp Tyr Gln Gly Met Leu Pro Val Cys Pro
            260                 265                 270

Leu Ile Pro Gly Ser Thr Thr Thr Ser Thr Gly Pro Cys Lys Thr Cys
        275                 280                 285

Thr Thr Pro Ala Gln Gly Asn Ser Met Phe Pro Ser Cys Cys Cys Thr
    290                 295                 300

Lys Pro Thr Asp Gly Asn Cys Thr Cys Ile Pro Ile Pro Ser Ser Trp
305                 310                 315                 320

Ala Phe Ala Lys Tyr Leu Trp Glu Trp Ala Ser Val Arg Phe Ser Trp
                325                 330                 335

Leu Ser Leu Leu Val Pro Phe Val Gln Trp Phe Val Gly Leu Ser Pro
            340                 345                 350

Thr Val Trp Leu Ser Ala Ile Trp Met Met Trp Tyr Trp Gly Pro Ser
        355                 360                 365

Leu Tyr Ser Ile Val Ser Pro Phe Ile Pro Leu Leu Pro Ile Phe Phe
    370                 375                 380

Cys Leu Trp Val Tyr Ile
385                 390
```

<210> SEQ ID NO 6
<211> LENGTH: 5882
<212> TYPE: DNA
<213> ORGANISM: Artificial Sequence
<220> FEATURE:
<223> OTHER INFORMATION: Description of Artificial Sequence: plasmid
      pCMV-II-E2661-sAg
<221> NAME/KEY: CDS
<222> LOCATION: (1992)..(3584)

<400> SEQUENCE: 6

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgaa gcttttgca aaagcctagg cctccaaaaa agcctcctca ctacttctgg    240
aatagctcag aggccgaggc ggcctcggcc tctgcataaa taaaaaaat tagtcagcca    300 tgggcggag aatgggcgga actgggcggg gagggaatta ttggctattg gccattgcat    360
acgttgtatc tatatcataa tatgtacatt tatattggct catgtccaat atgaccgcca    420
tgttgacatt gattattgac tagttattaa tagtaatcaa ttacggggtc attagttcat    480
agcccatata tggagttccg cgttacataa cttacggtaa atggcccgcc tggctgaccg    540
cccaacgacc cccgcccatt gacgtcaata atgacgtatg ttcccatagt aacgccaata    600
gggactttcc attgacgtca atgggtggag tatttacggt aaactgccca cttggcagta    660
catcaagtgt atcatatgcc aagtccgccc cctattgacg tcaatgacgg taaatggccc    720
gcctggcatt atgcccagta catgacctta cgggactttc ctacttggca gtacatctac    780
gtattagtca tcgctattac catggtgatg cggttttggc agtacaccaa tgggcgtgga    840
```

-continued

```
tagcggtttg actcacgggg atttccaagt ctccacccca ttgacgtcaa tgggagtttg      900
ttttggcacc aaaatcaacg ggactttcca aaatgtcgta ataacccgc cccgttgacg       960 caaatgggcg gtaggcgtgt acggtgggag gtctatataa gcagagctcg tttagtgaac     1020
cgtcagatcg cctggagacg ccatccacgc tgttttgacc tccatagaag acaccgggac     1080
cgatccagcc tccgcggccg ggaacggtgc attggaacgc ggattccccg tgccaagagt     1140
gacgtaagta ccgcctatag actctatagg cacacccctt tggctcttat gcatgctata    1200 ctgttttttgg cttgggggcct atacaccccc gctccttatg ctataggtga tggtatagct   1260
tagcctatag gtgtgggtta ttgaccatta ttgaccactc ccctattggt gacgatactt    1320
tccattacta atccataaca tggctctttg ccacaactat ctctattggc tatatgccaa     1380
tactctgtcc ttcagagact gacacggact ctgtattttt acaggatggg gtccatttat    1440
tatttacaaa ttcacatata caacaacgcc gtccccgtg cccgcagttt ttattaaaca      1500
tagcgtggga tctccgacat ctcgggtacg tgttccggac atgggctctt ctccggtagc    1560
ggcggagctt ccacatccga gccctggtcc catccgtcca gcggctcatg gtcgctcggc    1620
agctccttgc tcctaacagt ggaggccaga cttaggcaca gcacaatgcc caccaccacc    1680
agtgtgccgc acaaggccgt ggcggtaggg tatgtgtctg aaaatgagct cggagattgg    1740
gctcgcacct ggacgcagat ggaagactta aggcagcggc agaagaagat gcaggcagct    1800
gagttgttgt attctgataa gagtcagagg taactcccgt tgcggtgctg ttaacggtgg    1860
agggcagtgt agtctgagca gtactcgttg ctgccgcgcg cgccaccaga cataatagct    1920
gacagactaa cagactgttc cttccatgg gtcttttctg cagtcaccgt cgtcgacgaa     1980
ttcaagcaat c atg gat gca atg aag aga ggg ctc tgc tgt gtg ctg ctg     2030
            Met Asp Ala Met Lys Arg Gly Leu Cys Cys Val Leu Leu
             1               5                  10 ctg tgt gga gca gtc ttc gtt tcg ccc agc gct agc gaa acc cac gtc      2078
Leu Cys Gly Ala Val Phe Val Ser Pro Ser Ala Ser Glu Thr His Val
 15                  20                  25 acc ggg gga agt gcc ggc cac act gtg tct gga ttt gtt agc ctc ctc      2126
Thr Gly Gly Ser Ala Gly His Thr Val Ser Gly Phe Val Ser Leu Leu
 30                  35                  40                  45 gca cca ggc gcc aag cag aac gtc cag ctg atc aac acc aac ggc agt      2174
Ala Pro Gly Ala Lys Gln Asn Val Gln Leu Ile Asn Thr Asn Gly Ser
                 50                  55                  60 tgg cac ctc aat agc acg gcc ctg aac tgc aat gat agc ctc aac acc      2222
Trp His Leu Asn Ser Thr Ala Leu Asn Cys Asn Asp Ser Leu Asn Thr
             65                  70                  75 ggc tgg ttg gca ggg ctt ttc tat cac cac aag ttc aac tct tca ggc      2270
Gly Trp Leu Ala Gly Leu Phe Tyr His His Lys Phe Asn Ser Ser Gly
         80                  85                  90 tgt cct gag agg cta gcc agc tgc cga ccc ctt acc gat ttt gac cag      2318
Cys Pro Glu Arg Leu Ala Ser Cys Arg Pro Leu Thr Asp Phe Asp Gln
     95                 100                 105 ggc tgg ggc cct atc agt tat gcc aac gga agc ggc ccc gac cag cgc      2366
Gly Trp Gly Pro Ile Ser Tyr Ala Asn Gly Ser Gly Pro Asp Gln Arg
110                 115                 120                 125 ccc tac tgc tgg cac tac ccc cca aaa cct tgc ggt att gtg ccc gcg      2414
Pro Tyr Cys Trp His Tyr Pro Pro Lys Pro Cys Gly Ile Val Pro Ala
                130                 135                 140 aag agt gtg tgt ggt ccg gta tgc ttc act ccc agc ccc gtg gtg           2462
Lys Ser Val Cys Gly Pro Val Cys Phe Thr Pro Ser Pro Val Val
            145                 150                 155
```

-continued

| | | |
|---|---|---|
| gtg gga acg acc gac agg tcg ggc gcg ccc acc tac agc tgg ggt gaa<br>Val Gly Thr Thr Asp Arg Ser Gly Ala Pro Thr Tyr Ser Trp Gly Glu<br>          160                         165                      170 | 2510 |
| aat gat acg gac gtc ttc gtc ctt aac aat acc agg cca ccg ctg ggc<br>Asn Asp Thr Asp Val Phe Val Leu Asn Asn Thr Arg Pro Pro Leu Gly<br>175                       180                       185 | 2558 |
| aat tgg ttc ggt tgt acc tgg atg aac tca act gga ttc acc aaa gtg<br>Asn Trp Phe Gly Cys Thr Trp Met Asn Ser Thr Gly Phe Thr Lys Val<br>190                       195                     200               205 | 2606 |
| tgc gga gcg cct cct tgt gtc atc gga ggg gcg ggc aac aac acc ctg<br>Cys Gly Ala Pro Pro Cys Val Ile Gly Gly Ala Gly Asn Asn Thr Leu<br>                      210                       215                     220 | 2654 |
| cac tgc ccc act gat tgc ttc cgc aag cat ccg gac gcc aca tac tct<br>His Cys Pro Thr Asp Cys Phe Arg Lys His Pro Asp Ala Thr Tyr Ser<br>                 225                       230                     235 | 2702 |
| cgg tgc ggc tcc ggt ccc tgg atc aca ccc agg tgc ctg gtc gac tac<br>Arg Cys Gly Ser Gly Pro Trp Ile Thr Pro Arg Cys Leu Val Asp Tyr<br>                 240                       245                     250 | 2750 |
| ccg tat agg ctt tgg cat tat cct tgt acc atc aac tac acc ata ttt<br>Pro Tyr Arg Leu Trp His Tyr Pro Cys Thr Ile Asn Tyr Thr Ile Phe<br>255                       260                     265 | 2798 |
| aaa atc agg atg tac gtg gga ggg gtc gaa cac agg ctg gaa gct gcc<br>Lys Ile Arg Met Tyr Val Gly Gly Val Glu His Arg Leu Glu Ala Ala<br>270                       275                     280               285 | 2846 |
| tgc aac tgg acg cgg ggc gaa cgt tgc gat ctg gaa gat agg gac agg<br>Cys Asn Trp Thr Arg Gly Glu Arg Cys Asp Leu Glu Asp Arg Asp Arg<br>                      290                       295                     300 | 2894 |
| tcc gag atc gat atg gag aac atc aca tca gga ttc cta gga ccc ctg<br>Ser Glu Ile Asp Met Glu Asn Ile Thr Ser Gly Phe Leu Gly Pro Leu<br>                 305                       310                     315 | 2942 |
| ctc gtg tta cag gcg ggg ttt ttc ttg ttg aca aga atc ctc aca ata<br>Leu Val Leu Gln Ala Gly Phe Phe Leu Leu Thr Arg Ile Leu Thr Ile<br>320                       325                     330 | 2990 |
| ccg cag agt cta gac tcg tgg tgg act tct ctc aat ttt cta ggg gga<br>Pro Gln Ser Leu Asp Ser Trp Trp Thr Ser Leu Asn Phe Leu Gly Gly<br>               335                       340                     345 | 3038 |
| tct ccc gtg tgt ctt ggc caa aat tcg cag tcc cca acc tcc aat cac<br>Ser Pro Val Cys Leu Gly Gln Asn Ser Gln Ser Pro Thr Ser Asn His<br>350                       355                     360               365 | 3086 |
| tca cca acc tcc tgt cct cca att tgt cct ggt tat cgc tgg atg tgt<br>Ser Pro Thr Ser Cys Pro Pro Ile Cys Pro Gly Tyr Arg Trp Met Cys<br>                      370                       375                     380 | 3134 |
| ctg cgg cgt ttt atc ata ttc ctc ttc atc ctg ctg cta tgc ctc atc<br>Leu Arg Arg Phe Ile Ile Phe Leu Phe Ile Leu Leu Leu Cys Leu Ile<br>                      385                       390                     395 | 3182 |
| ttc tta ttg gtt ctt ctg gat tat caa ggt atg ttg ccc gtt tgt cct<br>Phe Leu Leu Val Leu Leu Asp Tyr Gln Gly Met Leu Pro Val Cys Pro<br>               400                       405                     410 | 3230 |
| cta att cca gga tca aca aca acc agt acg gga cca tgc aaa acc tgc<br>Leu Ile Pro Gly Ser Thr Thr Thr Ser Thr Gly Pro Cys Lys Thr Cys<br>415                       420                     425 | 3278 |
| acg act cct gct caa ggc aac tct atg ttt ccc tca tgt tgc tgt aca<br>Thr Thr Pro Ala Gln Gly Asn Ser Met Phe Pro Ser Cys Cys Cys Thr<br>430                       435                     440               445 | 3326 |
| aaa cct acg gat gga aat tgc acc tgt att ccc atc cca tcg tcc tgg<br>Lys Pro Thr Asp Gly Asn Cys Thr Cys Ile Pro Ile Pro Ser Ser Trp<br>                      450                       455                     460 | 3374 |
| gct ttc gca aaa tac cta tgg gag tgg gcc tca gtc cgt ttc tct tgg<br>Ala Phe Ala Lys Tyr Leu Trp Glu Trp Ala Ser Val Arg Phe Ser Trp<br>               465                       470                     475 | 3422 |

-continued

| | |
|---|---|
| ctc agt tta cta gtg cca ttt gtt cag tgg ttc gta ggg ctt tcc ccc<br>Leu Ser Leu Leu Val Pro Phe Val Gln Trp Phe Val Gly Leu Ser Pro<br>   480        485        490 | 3470 |
| act gtt tgg ctt tca gct ata tgg atg atg tgg tat tgg ggg cca agt<br>Thr Val Trp Leu Ser Ala Ile Trp Met Met Trp Tyr Trp Gly Pro Ser<br>495        500        505 | 3518 |
| ctg tac agc atc gtg agt ccc ttt ata ccg ctg tta cca att ttc ttt<br>Leu Tyr Ser Ile Val Ser Pro Phe Ile Pro Leu Leu Pro Ile Phe Phe<br>510        515        520        525 | 3566 |
| tgt ctc tgg gta tac att taagaattca gactcgagca agtctagaaa<br>Cys Leu Trp Val Tyr Ile<br>       530 | 3614 |
| ggcgcgccaa gatatcaagg atccactacg cgttagagct cgctgatcag cctcgactgt | 3674 |
| gccttctagt tgccagccat ctgttgtttg cccctccccc gtgccttcct tgaccctgga | 3734 |
| aggtgccact cccactgtcc tttcctaata aaatgaggaa attgcatcgc attgtctgag | 3794 |
| taggtgtcat tctattctgg ggggtggggt gggcaggac agcaaggggg aggattggga | 3854 |
| agacaatagc aggcatgctg gggagctctt ccgcttcctc gctcactgac tcgctgcgct | 3914 |
| cggtcgttcg gctgcggcga gcggtatcag ctcactcaaa ggcggtaata cggttatcca | 3974 |
| cagaatcagg ggataacgca ggaaagaaca tgtgagcaaa aggccagcaa aaggccagga | 4034 |
| accgtaaaaa ggccgcgttg ctggcgtttt tccataggct ccgcccccct gacgagcatc | 4094 |
| acaaaaatcg acgctcaagt cagaggtggc gaaacccgac aggactataa agataccagg | 4154 |
| cgtttccccc tggaagctcc ctcgtgcgct ctcctgttcc gaccctgccg cttaccggat | 4214 |
| acctgtccgc ctttctccct tcgggaagcg tggcgctttc tcaatgctca cgctgtaggt | 4274 |
| atctcagttc ggtgtaggtc gttcgctcca agctgggctg tgtgcacgaa ccccccgttc | 4334 |
| agcccgaccg ctgcgcctta tccggtaact atcgtcttga gtccaacccg gtaagacacg | 4394 |
| acttatcgcc actggcagca gccactggta acaggattag cagagcgagg tatgtaggcg | 4454 |
| gtgctacaga gttcttgaag tggtggccta actacggcta cactagaagg acagtatttg | 4514 |
| gtatctgcgc tctgctgaag ccagttacct tcggaaaaag agttggtagc tcttgatccg | 4574 |
| gcaaacaaac caccgctggt agcggtggtt tttttgtttg caagcagcag attacgcgca | 4634 |
| gaaaaaaagg atctcaagaa gatcctttga tcttttctac ggggtctgac gctcagtgga | 4694 |
| acgaaaactc acgttaaggg attttggtca tgagattatc aaaaaggatc ttcacctaga | 4754 |
| tccttttaaa ttaaaaatga agttttaaat caatctaaag tatatatgag taaacttggt | 4814 |
| ctgacagtta ccaatgctta atcagtgagg cacctatctc agcgatctgt ctatttcgtt | 4874 |
| catccatagt tgcctgactc cccgtcgtgt agataactac gatacgggag ggcttaccat | 4934 |
| ctggccccag tgctgcaatg ataccgcgag acccacgctc accggctcca gatttatcag | 4994 |
| caataaacca gccagccgga agggccgagc gcagaagtgg tcctgcaact ttatccgcct | 5054 |
| ccatccagtc tattaattgt tgccgggaag ctagagtaag tagttcgcca gttaatagtt | 5114 |
| tgcgcaacgt tgttgccatt gctacaggca tcgtggtgtc acgctcgtcg tttggtatgg | 5174 |
| cttcattcag ctccggttcc caacgatcaa ggcgagttac atgatccccc atgttgtgca | 5234 |
| aaaaagcggt tagctccttc ggtcctccga tcgttgtcag aagtaagttg gccgcagtgt | 5294 |
| tatcactcat ggttatggca gcactgcata attctcttac tgtcatgcca tccgtaagat | 5354 |
| gcttttctgt gactggtgag tactcaacca agtcattctg agaatagtgt atgcggcgac | 5414 |
| cgagttgctc ttgcccggcg tcaatacggg ataataccgc gccacatagc agaactttaa | 5474 |

-continued

```
aagtgctcat cattggaaaa cgttcttcgg ggcgaaaact ctcaaggatc ttaccgctgt    5534
tgagatccag ttcgatgtaa cccactcgtg cacccaactg atcttcagca tcttttactt    5594
tcaccagcgt ttctgggtga gcaaaaacag gaaggcaaaa tgccgcaaaa aagggaataa    5654
gggcgacacg gaaatgttga atactcatac tcttcctttt tcaatattat tgaagcattt    5714
atcagggtta ttgtctcatg agcggataca tatttgaatg tatttagaaa aataaacaaa    5774 tagggggttcc gcgcacattt ccccgaaaag tgccacctga cgtctaagaa accattatta    5834
tcatgacatt aacctataaa aataggcgta tcacgaggcc ctttcgtc                 5882
```

<210> SEQ ID NO 7
<211> LENGTH: 531
<212> TYPE: PRT
<213> ORGANISM: Artificial Sequence
<220> FEATURE:
<223> OTHER INFORMATION: Description of Artificial Sequence: plasmid
      pCMV-II-E2661-sAg

<400> SEQUENCE: 7

```
Met Asp Ala Met Lys Arg Gly Leu Cys Cys Val Leu Leu Leu Cys Gly
  1               5                  10                  15

Ala Val Phe Val Ser Pro Ser Ala Ser Glu Thr His Val Thr Gly Gly
                 20                  25                  30

Ser Ala Gly His Thr Val Ser Gly Phe Val Ser Leu Leu Ala Pro Gly
             35                  40                  45

Ala Lys Gln Asn Val Gln Leu Ile Asn Thr Asn Gly Ser Trp His Leu
         50                  55                  60

Asn Ser Thr Ala Leu Asn Cys Asn Asp Ser Leu Asn Thr Gly Trp Leu
 65                  70                  75                  80

Ala Gly Leu Phe Tyr His His Lys Phe Asn Ser Ser Gly Cys Pro Glu
                 85                  90                  95

Arg Leu Ala Ser Cys Arg Pro Leu Thr Asp Phe Asp Gln Gly Trp Gly
            100                 105                 110

Pro Ile Ser Tyr Ala Asn Gly Ser Gly Pro Asp Gln Arg Pro Tyr Cys
        115                 120                 125

Trp His Tyr Pro Pro Lys Pro Cys Gly Ile Val Pro Ala Lys Ser Val
    130                 135                 140

Cys Gly Pro Val Tyr Cys Phe Thr Pro Ser Pro Val Val Val Gly Thr
145                 150                 155                 160

Thr Asp Arg Ser Gly Ala Pro Thr Tyr Ser Trp Gly Glu Asn Asp Thr
                165                 170                 175

Asp Val Phe Val Leu Asn Asn Thr Arg Pro Pro Leu Gly Asn Trp Phe
            180                 185                 190

Gly Cys Thr Trp Met Asn Ser Thr Gly Phe Thr Lys Val Cys Gly Ala
        195                 200                 205

Pro Pro Cys Val Ile Gly Gly Ala Gly Asn Asn Thr Leu His Cys Pro
    210                 215                 220

Thr Asp Cys Phe Arg Lys His Pro Asp Ala Thr Tyr Ser Arg Cys Gly
225                 230                 235                 240

Ser Gly Pro Trp Ile Thr Pro Arg Cys Leu Val Asp Tyr Pro Tyr Arg
                245                 250                 255

Leu Trp His Tyr Pro Cys Thr Ile Asn Tyr Thr Ile Phe Lys Ile Arg
            260                 265                 270

Met Tyr Val Gly Gly Val Glu His Arg Leu Glu Ala Ala Cys Asn Trp
        275                 280                 285
```

-continued

```
Thr Arg Gly Glu Arg Cys Asp Leu Glu Asp Arg Asp Arg Ser Glu Ile
    290             295             300

Asp Met Glu Asn Ile Thr Ser Gly Phe Leu Gly Pro Leu Leu Val Leu
305             310             315             320

Gln Ala Gly Phe Phe Leu Leu Thr Arg Ile Leu Thr Ile Pro Gln Ser
            325             330             335

Leu Asp Ser Trp Trp Thr Ser Leu Asn Phe Leu Gly Gly Ser Pro Val
            340             345             350

Cys Leu Gly Gln Asn Ser Gln Ser Pro Thr Ser Asn His Ser Pro Thr
            355             360             365

Ser Cys Pro Pro Ile Cys Pro Gly Tyr Arg Trp Met Cys Leu Arg Arg
    370             375             380

Phe Ile Ile Phe Leu Phe Ile Leu Leu Leu Cys Leu Ile Phe Leu Leu
385             390             395             400

Val Leu Leu Asp Tyr Gln Gly Met Leu Pro Val Cys Pro Leu Ile Pro
            405             410             415

Gly Ser Thr Thr Thr Ser Thr Gly Pro Cys Lys Thr Cys Thr Thr Pro
            420             425             430

Ala Gln Gly Asn Ser Met Phe Pro Ser Cys Cys Cys Thr Lys Pro Thr
    435             440             445

Asp Gly Asn Cys Thr Cys Ile Pro Ile Pro Ser Ser Trp Ala Phe Ala
    450             455             460

Lys Tyr Leu Trp Glu Trp Ala Ser Val Arg Phe Ser Trp Leu Ser Leu
465             470             475             480

Leu Val Pro Phe Val Gln Trp Phe Val Gly Leu Ser Pro Thr Val Trp
            485             490             495

Leu Ser Ala Ile Trp Met Met Trp Tyr Trp Gly Pro Ser Leu Tyr Ser
            500             505             510

Ile Val Ser Pro Phe Ile Pro Leu Leu Pro Ile Phe Phe Cys Leu Trp
            515             520             525

Val Tyr Ile
    530
```